US012708527B2

(12) United States Patent
Hunt et al.

(10) Patent No.: US 12,708,527 B2
(45) Date of Patent: Aug. 18, 2026

(54) APPARATUS, SYSTEM, AND METHOD FOR DETERMINING A POSITION OF A HIP PROSTHESIS IN A BONE OF A PATIENT

(71) Applicant: DePuy Ireland Unlimited Company, Ringaskiddy (IE)

(72) Inventors: Christopher Hunt, Leeds (GB); Brittany Marshall, Warsaw, IN (US); Patrick Cannon, Warsaw, IN (US); Zahra Ehteshami, Leeds (GB); Filip Leszko, Philadelphia, PA (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 0 days.

(21) Appl. No.: 18/823,359

(22) Filed: Sep. 3, 2024

(65) Prior Publication Data

US 2025/0107904 A1 Apr. 3, 2025

Related U.S. Application Data

(60) Provisional application No. 63/571,818, filed on Mar. 29, 2024, provisional application No. 63/541,603, filed on Sep. 29, 2023.

(51) Int. Cl.
*A61F 2/46* (2006.01)
*A61B 34/20* (2016.01)

(52) U.S. Cl.
CPC .... *A61F 2/4609* (2013.01); *A61B 2034/2046* (2016.02)

(58) Field of Classification Search
CPC .. A61F 2/32; A61F 2/4609; A61F 2002/4633; A61B 34/10; A61B 34/25;
(Continued)

(56) References Cited

U.S. PATENT DOCUMENTS 5,715,836 A 2/1998 Kliegis et al.
5,995,738 A 11/1999 Digioia, III et al.
(Continued)

FOREIGN PATENT DOCUMENTS

JP 2004105551 A 4/2004
JP 2005185767 A 7/2005
(Continued)

OTHER PUBLICATIONS

Alvarez et al., "Fluoroscopic Imaging of Acetabular Cup Position During THA Through a Direct Anterior Approach," Orthopedics, Oct. 2013, pp. 776-777, vol. 36, No. 10.
(Continued)

*Primary Examiner* — Anu Ramana
(74) *Attorney, Agent, or Firm* — Barnes & Thornburg LLP

(57) ABSTRACT

Apparatus, systems, and methods for determining a position of a hip prosthesis in a bone of a patient are disclosed. One method for planning an orthopaedic surgical procedure may comprise determining a first set of target orientations for an acetabular cup of the hip prosthesis when the femoral prosthesis of the hip prosthesis is oriented at a first version, determining a second set of target orientations for the acetabular cup when the femoral prosthesis is oriented at a second version different from the first version, displaying a first graphical user interface (GUI) that comprises a first graphic representing the first set of target orientations for the acetabular cup, receiving a user input, and, in response to the input, displaying a second GUI that comprises a second graphic representing the second set of target orientations for the acetabular cup.

20 Claims, 20 Drawing Sheets

(58) Field of Classification Search
CPC ........ A61B 2034/102; A61B 2034/105; A61B 2034/108; A61B 2034/2046
See application file for complete search history.

(56) References Cited

U.S. PATENT DOCUMENTS 6,205,411 B1 3/2001 Digioia et al.
6,597,818 B2 7/2003 Levienaise-Obadia et al.
8,160,345 B2 * 4/2012 Pavlovskaia ............ G06T 17/20 382/131
9,248,002 B2 2/2016 McCarthy
9,603,711 B2 3/2017 Bojarski et al.
9,662,228 B2 5/2017 McCarthy
9,687,259 B2 * 6/2017 Pavlovskaia ............. G06T 7/13
9,913,691 B2 3/2018 Brooks
10,182,871 B2 1/2019 Wollowick et al.
10,321,961 B2 6/2019 McCarthy et al.
10,433,914 B2 10/2019 Wollowick et al.
10,500,067 B2 12/2019 McCarthy
10,595,943 B2 3/2020 Barsoum et al.
10,610,305 B2 4/2020 Wollowick et al.
10,687,856 B2 * 6/2020 Park ....................... B33Y 80/00
10,758,198 B2 9/2020 Wollowick et al.
10,765,384 B2 9/2020 Wollowick et al.
10,959,782 B2 3/2021 Wollowick et al.
11,071,592 B2 7/2021 McGuan et al.
11,107,586 B1 8/2021 Decook et al.
11,147,626 B2 10/2021 Murphy et al.
11,241,287 B2 2/2022 Boettner
11,318,025 B2 5/2022 Schipper et al.
11,337,760 B2 5/2022 Veilleux et al.
11,337,762 B2 5/2022 Mckinnon et al.
11,439,467 B1 9/2022 Park
11,534,127 B2 12/2022 Wollowick et al.
11,642,174 B2 5/2023 Wollowick et al.
11,737,893 B2 * 8/2023 Schipper ............... G06T 19/006 345/419
11,887,306 B2 1/2024 Cooper et al.
12,198,812 B2 1/2025 Decook et al.
2002/0055692 A1 5/2002 Tanaka et al.
2003/0176860 A1 9/2003 Shimura
2004/0087852 A1 5/2004 Chen et al.
2004/0117028 A1 6/2004 Iversen
2004/0171924 A1 9/2004 Mire et al.
2005/0054917 A1 3/2005 Kitson
2005/0203384 A1 9/2005 Sati et al.
2006/0095047 A1 5/2006 De La Barrera
2006/0293614 A1 12/2006 Radinsky et al.
2008/0021299 A1 1/2008 Meulink
2008/0027312 A1 1/2008 Dick
2008/0056552 A1 3/2008 Muller
2008/0075348 A1 3/2008 Rappaport et al.
2008/0120262 A1 5/2008 Habets et al.
2008/0146969 A1 6/2008 Kurtz
2008/0255584 A1 10/2008 Beverland et al.
2009/0089034 A1 4/2009 Penney et al.
2009/0316967 A1 12/2009 Dardenne et al.
2010/0030231 A1 2/2010 Revie et al.
2010/0086181 A1 4/2010 Zug et al.
2010/0197639 A1 * 8/2010 Lang ..................... A61B 6/505 514/143
2011/0093087 A1 4/2011 Mcmahon et al.
2011/0313424 A1 12/2011 Bono et al.
2012/0016269 A1 1/2012 Moctezuma De La Barrera
2012/0116533 A1 5/2012 Forsell
2012/0157887 A1 6/2012 Fanson et al.
2012/0194505 A1 8/2012 Beck
2012/0209394 A1 8/2012 Bojarski et al.
2012/0230573 A1 9/2012 Ito et al.
2013/0046310 A1 2/2013 Ranawat et al.
2013/0053858 A1 2/2013 Penenberg
2013/0053859 A1 2/2013 Penenberg
2013/0072821 A1 3/2013 Odermatt et al.
2013/0304429 A1 11/2013 Haimerl
2014/0093154 A1 4/2014 Penenberg
2014/0378828 A1 12/2014 Penenberg et al.
2015/0088145 A1 3/2015 Mccarthy
2015/0088146 A1 3/2015 Mccarthy
2015/0117608 A1 4/2015 Lytle et al.
2015/0150523 A1 6/2015 Sirpad et al.
2015/0227679 A1 8/2015 Kamer et al.
2015/0238271 A1 8/2015 Wollowick et al.
2015/0257846 A1 9/2015 Kubiak et al.
2015/0272695 A1 10/2015 Kubiak et al.
2016/0100909 A1 4/2016 Wollowick et al.
2016/0128654 A1 5/2016 Wollowick et al.
2016/0203608 A1 7/2016 Izmirli et al.
2016/0225192 A1 8/2016 Yarin et al.
2017/0042619 A1 2/2017 Brooks
2017/0128135 A1 5/2017 Mccarthy et al.
2017/0143433 A1 5/2017 Fanson et al.
2017/0165008 A1 6/2017 Finley
2017/0202682 A1 7/2017 Mccarthy
2017/0215967 A1 8/2017 Spath
2017/0224418 A1 8/2017 Boettner et al.
2017/0258526 A1 9/2017 Lang
2017/0333137 A1 11/2017 Roessler
2018/0161101 A1 6/2018 Barsoum et al.
2018/0199995 A1 7/2018 Odermatt et al.
2018/0263697 A1 * 9/2018 Eskesen ................. G16H 30/40
2018/0263699 A1 9/2018 Murphy et al.
2019/0090962 A1 3/2019 Boettner
2019/0298452 A1 10/2019 Veilleux et al.
2019/0350728 A1 11/2019 Van Der Walt et al.
2019/0385303 A1 12/2019 Petersen et al.
2020/0205900 A1 7/2020 Buckland et al.
2020/0246079 A1 8/2020 Shevlev et al.
2020/0323648 A1 10/2020 Samuelson et al.
2020/0323649 A1 10/2020 Schipper et al.
2020/0405398 A1 12/2020 Amanatullah
2021/0220054 A1 7/2021 Parker et al.
2021/0322148 A1 10/2021 Mitra et al.
2022/0000562 A1 1/2022 Murphy et al.
2022/0008131 A1 1/2022 Sculco et al.
2022/0039869 A1 2/2022 Dees, Jr.
2022/0117663 A1 4/2022 McGuan et al.
2022/0125515 A1 4/2022 McGuan et al.
2022/0148454 A1 5/2022 Jaramaz et al.
2022/0148739 A1 5/2022 Farley et al.
2022/0202494 A1 6/2022 Dressler et al.
2022/0202503 A1 6/2022 Dressler et al.
2022/0249248 A1 8/2022 Schipper et al.
2022/0323159 A1 10/2022 Boettner et al.
2023/0000556 A1 1/2023 McKinnon et al.
2023/0181257 A1 6/2023 Mcguan et al.
2023/0277331 A1 9/2023 Beck et al.
2024/0261030 A1 * 8/2024 Long ..................... G16H 50/70
2025/0149183 A1 5/2025 DeCook et al.

FOREIGN PATENT DOCUMENTS

JP 2007151742 A 6/2007
JP 2009136384 A 6/2009
JP 2012532665 A 12/2012
WO 2007009263 A1 1/2007
WO 2009108683 A1 9/2009
WO 2013049534 A1 4/2013
WO 2013175471 A1 11/2013
WO 2014025305 A1 2/2014
WO 2014069553 A1 5/2014
WO 2016180438 A1 11/2016
WO 2017106858 A1 6/2017
WO 2018162322 A1 9/2018
WO 2019068194 A1 4/2019
WO 2019191722 A1 10/2019
WO 2019241516 A1 12/2019
WO 2020102886 A1 5/2020
WO 2020163314 A1 8/2020
WO 2020163316 A1 8/2020
WO 2020163317 A1 8/2020
WO 2020163318 A1 8/2020
WO 2020163324 A1 8/2020
WO 2020163328 A1 8/2020
WO 2020163330 A1 8/2020

(56) References Cited

FOREIGN PATENT DOCUMENTS

| | | | |
|---|---|---|---|
| WO | 2020163352 | A1 | 8/2020 |
| WO | 2020163355 | A1 | 8/2020 |
| WO | 2020163358 | A1 | 8/2020 |
| WO | 2021262539 | A1 | 12/2021 |
| WO | 2022144448 | A1 | 7/2022 |
| WO | 2023044138 | A1 | 3/2023 |
| WO | 2023059905 | A1 | 4/2023 |

OTHER PUBLICATIONS

Alvarez, "Fluoroscopic Imaging of Acetabular Cup Position During THA Through a Direct Anterior Approach," Orthopedics, Jan. 2014, p. 12, vol. 37, No. 1.

Babisch et al., "The Rationale for Tilt-Adjusted Acetabular Cup Navigation," The Journal of Bone & Joint Surgery, Feb. 2008, pp. 357-365, vol. 90-A, No. 2.

Bachhal et al., "A new method of measuring acetabular cup anteversion on simulated radiographs," International Orthopaedics (SICOT), May 31, 2012, pp. 1813-1818, vol. 36, Springer.

Bergmann et al., "Hip contact forces and gait patterns from routine activities," Journal of Biomechanics, Jul. 2001, pp. 859-871, vol. 34(7), Elsevier Science Ltd.

Bergmann et al., "Standardized Loads Acting in Hip Implants," PLoS ONE, May 19, 2016, 23 pages, vol. 11(5).

Blondel et al., "Sacro-femoral-pubic angle: a coronal parameter to estimate pelvic tilt," European Spine Journal, Nov. 24, 2011, pp. 719-724, vol. 21, Springer-Verlag.

Brown et al., "Impingement in total hip replacement: mechanisms and consequences," Current Orthopaedics, 2008, pp. 376-391, vol. 22, Elsevier, Inc.

Buckland et al., "Sagittal pelvic orientation: a comparison of two methods of measurement," Bulletin of the Hospital for Joint Diseases 2017, pp. 234-240, vol. 75(4).

Chevillotte et al., "Variability in Hip Range of Motion on Clinical Examination," The Journal of Arthroplasty, Aug. 2009, pp. 693-697, vol. 24(5), Elsevier, Inc.

Cuptimize, Inc., Traditional 510(k) Application for Cuptimize Software, submitted confidentially to the U.S. Food and Drug Administration on Dec. 14, 2020, 215 pages (partially redacted).

Depuy Orthopaedics, Inc., Excerpts from Traditional 510(k) Application for DePuy Cuptimize Advanced, submitted confidentially to the U.S. Food and Drug Administration on May 24, 2023, 22 pages.

Depuy Synthes Products, Inc., Corrected Request for Supplemental Examination of U.S. Pat. No. 11,107,586, assigned U.S. Appl. No. 96/050,073, Dec. 24, 2024, 106 pages.

Depuy Synthes Products, Inc., Request for Supplemental Examination of U.S. Pat. No. 11,107,586, assigned U.S. Appl. No. 96/050,073, Dec. 6, 2024, 81 pages.

Depuy Synthes, Cuptimize Hip-Spine Analysis User Guide, Sep. 27, 2022, 48 pages.

Depuy Synthes, Velys Hip Navigation User Guide (Version 4.1), Jul. 2021, 84 pages.

Eftekhary et al., "A systematic approach to the hip-spine relationship and its applications to total hip arthroplasty," The Bone & Joint Journal, Jul. 2019, pp. 808-816, vol. 101-B, No. 7.

Esposito et al., "Biplanar Low-Dose Radiography Is Accurate for Measuring Combined Anteversion After Total Hip Arthroplasty," HSS Journal, Feb. 5, 2019, pp. 23-29, vol. 16, No. 1, Springer Nature.

European Patent Office, Communication with Extended European Search Report for European Patent Application No. 21828607.8, Jul. 2, 2024, 12 pages.

European Patent Office, International Search Report and Written Opinion for International Application No. PCT/EP2021/087907, May 3, 2022, 16 pages.

European Patent Office, International Search Report and Written Opinion for International Application No. PCT/EP2024/076483, Feb. 24, 2025, 24 pages.

Gibbons et al., "Development Of A Statistical Shape-Function Model Of the Implanted Knee For Real-Time Prediction Of Joint Mechanics," Journal of Biomechanics, 2019; pp. 55-63, vol. 88.

Goodell et al., "Computer Navigation vs. Conventional Overlay Methods in Direct Anterior Total Hip Arthroplasty: A Single Surgeon Experience," Cureus, Oct. 4, 2022, 10 pages, vol. 14(10).

Heckmann et al., "Late Dislocation Following Total Hip Arthroplasty: Spinopelvic Imbalance as a Causative Factor," Journal of Bone and Joint Surgery, Nov. 7, 2018, pp. 1845-1853, vol. 100-A, The Journal of Bone and Joint Surgery, Incorporated.

Hofmann et al., "Minimizing Leg-Length Inequality in Total Hip Arthroplasty: Use of Preoperative Templating and an Intraoperative X-Ray," The American Journal of Orthopedics, Jan. 2008, pp. 18-23, vol. 37(1).

Imai et al., "Correlation of tilt of the anterior pelvic plane angle with anatomical pelvic tilt and morphological configuration of the acetabulum in patients with developmental dysplasia of the hip: a cross-sectional study," Journal of Orthopaedic Surgery and Research, Oct. 17, 2019, 7 pages, vol. 14, No. 323, Springer Nature.

Inaba et al., "Preoperative planning for implant placement with consideration of pelvic tilt in total hip arthroplasty: posoperative efficacy evaluation," BMC Musculoskeletal Disorders, Jul. 13, 2016, 7 pages, vol. 17, No. 280, CrossMark.

Jaramaz et al., "CupAlign: Computer-Assisted Postoperative Radiographic Measurement of Acetabular Components Following Total Hip Arthroplasty," Medical Image Computing and Computer Assisted Intervention (MICCAI), 1999, pp. 876-882, Springer-Verlag.

Jointpoint, Inc., JointPoint User Guide Version 3.4, Oct. 14, 2018, 92 pages.

Kleeman-Forsthuber et al., "Reliability of Spinopelvic Measurements That May Influence the Cup Position in Total Hip Arthroplasty," The Journal of Arthroplasty, Jun. 24, 2020, pp. 3758-3764, vol. 35, Elsevier Inc.

Labronici et al., "Positioning of the acetabular component in cemented prostheses—radiograph calculation," Revista Brasileira de Ortopedia (English Edition), 2013, pp. 62-68, vol. 48(1), Elsevier Editora Ltda.

Larose et al., "Post-Operative Measurement of Acetabular Cup Position Using X-ray/CT Registration," Medical Image Computing and Computer-Assisted Intervention (MICCAI), 2000, pp. 1104-1113, Springer-Verlag.

Lewinnek et al., "Dislocations after total hip-replacement arthroplasties," The Journal of Bone and Joint Surgery, Mar. 1978, pp. 217-220, vol. 60-A(2).

Liaw et al., "A New Tool for Measuring Cup Orientation in Total Hip Arthroplasties from Plain Radiographs," Clinical Orthopaedics and Related Research, Oct. 2006, pp. 134-139, vol. 451, Lippincott Wiliams & Wilkins.

Lo Re et al., "Sacro-Femoral-Pubic Angle and Acetabular Cup Anteversion in Total Hip Arthroplasty," EC Orthopaedics, May 31, 2019, pp. 429-437, vol. 10(6).

Lu et al., "Reliability and Validity of Measuring Acetabular Component Orientation by Plain Anteroposterior Radiographs," Clinical Orthopaedics and Related Research, May 4, 2013, pp. 2987-2994, vol. 471, Springer.

Luthringer et al., "A Preoperative Workup of a 'Hip-Spine' Total Hip Arthroplasty Patient: A Simplified Approach to a Complex Problem," The Journal of Arthroplasty, Jan. 18, 2019, pp. S57-S70, vol. 34, Elsevier Inc.

Maratt et al., "Pelvic tilt in patients undergoing total hip arthroplasty: when does it matter?" Author Manuscript, 2014, 15 pages, Elsevier Inc.

Matta et al., "Single-Incision Anterior Approach for Total Hip Arthroplasty on an Orthopaedic Table," Clinical Orthopaedics and Related Research, Dec. 2005, pp. 115-124, vol. 441, Lippincott Williams & Wilkins.

Mccarthy et al., "The Effect of Pelvic Tilt and Femoral Head Size on Hip Range-of-Motion to Impingement," The Journal of Arthroplasty, Jun. 15, 2017, pp. 3544-3549, vol. 32, Elsevier, Inc.

Miki et al., "Risk of edge loading and prosthesis impingement due to posterior pelvic tilting after total hip arthroplasty," Clinical Biomechanics, 2014, pp. 607-613, vol. 29, No. 4, Elsevier, Inc.

(56) References Cited

OTHER PUBLICATIONS

Murphy et al., "The Safe Zone Range for Cup Anteversion Is Narrower Than for Inclination in THA," Clinical Orthopaedics and Related Research, Jan. 17, 2018, pp. 325-335, vol. 476, No. 2, Wolters Kluwer.
Murray, "The definition and measurement of acetabular orientation," The Journal of Bone and Joint Surgery, 1993, pp. 228-232, vol. 75-B.
Myers et al., "Effect of intraoperative treatment options on hip joint stability following total hip arthroplasty," Journal of Orthopaedic Research, 2022, pp. 604-613, vol. 40, Wiley Periodicals LLC.
Myers et al., "Spinopelvic Mobility in THA and Lumbar Fusion Patients Across a Range of Common Functional X-ray Positions," Annual Meeting of Orthopaedic Research Society, Feb. 2022, Tampa Bay, FL.
Penney et al., "Postoperative Calculation of Acetabular Cop Position Using 2-D-3-D Registration," IEEE Transactions on Biomedical Engineering, Jul. 2007, pp. 1342-1348, vol. 54(7), IEEE.
Philippot et al., "Pelvic Balance in Sagittal and Lewinnek Reference Planes in the Standing, Supine and Sitting Positions," Orthopaedics & Traumatology: Surgery & Research, 2009, pp. 70-76, vol. 95, Elsevier Masson.
Pierrepont et al., "Patient-Specific Component Alignment in Total Hip Arthroplasty," Reconstructive Review, Dec. 2016, pp. 27-33, vol. 6(4), Joint Implant Surgery & Research Foundation.
Pierrepont et al., "Variation in functional pelvic tilt in patients undergoing total hip arthroplasty," The Bone & Joint Journal, Feb. 2017, pp. 184-191, vol. 99-B.
Pierrepont, Patient-Specific Component Alignment in Total Hip Arthroplasty, Jun. 2017, 321 pages.
Depuy Synthes Products, Inc., Response to Non-Final Office Action in U.S. Appl. No. 96/050,073, Jul. 9, 2025, 14 pages.
Ezquerra et al., "Range of Movement for Impingement and Dislocation Avoidance in Total Hip Replacement Predicted by Finite Element Model," J. Med. Biol. Eng., Jan. 21, 2017, pp. 26-34, vol. 37, Springer.
Henebry et al., "The Effect of Pelvic Tilt on Radiographic Markers of Acetabular Coverage," The American Journal of Sports Medicine, 2013, pp. 2599-2603, vol. 41(11), Sage.
Mahboba et al., "Improving of artificial hip joint design by studying multiple angles of articulation between femoral head and acetabular liner," International Journal of Energy and Environment, Jul. 31, 2019, pp. 195-210, vol. 10(4), International Energy & Environment Foundation.
Pedersen et al., "Temporal and Spatial Distributions of Directional Counterface Motion at the Acetabular Bearing Surface in Total Hip Arthroplasty," The lowa Orthopaedic Journal, 1998, pp. 43-53, vol. 18.
Pierrepont et al., "The effect of seated pelvic tilt on posterior edge-loading in total hip arthroplasty: A finite element investigation," Journal of Engineering in Medicine, 2018, pp. 241-248, vol. 232(3), Sage.
United States Patent & Trademark Office, Office Action in Ex Parte Reexamination U.S. Appl. No. 96/050,073, May 9, 2025, 43 pages.
Ragsdale et al., "Pelvic Tilt Evaluation From Frontal Radiographs: The Validity, Interobserver Reliability and Intraobserver Reproducibility of the Sacro-Femoral-Pubic Parameter," The Journal of Arthroplasty, Nov. 23, 2016, pp. 1665-1669, vol. 32, Elsevier Inc.
Tsukamoto et al., "Proposal of accurate cup placement procedure during total hip arthroplasty based on pelvic tilt discrepancies in the lateral position," Scientific Reports, Jul. 6, 2021, 9 pages, vol. 11, No. 13870, Springer Nature.
United States Patent & Trademark Office, International Search Report and Written Opinion for International Application No. PCT/US2021/038006, Sep. 29, 2021, 9 pages.
United States Patent & Trademark Office, Reasons for Substantial New Question of Patentability Determination in U.S. Appl. No. 96/050,073, Feb. 14, 2025, 37 pages.
Vigdorchik et al., "2021 Otto Aufranc Award: A simple Hip-Spine Classification for total hip arthroplasty," The Bone & Joint Journal, Jul. 2021, pp. 17-24, vol. 103-B, No. 7.
Vigdorchik et al., "Prevalence of Risk Factors for Adverse Spinopelvic Mobility Among Patients Undergoing Total Hip Arthroplasty," The Journal of Arthroplasty, Jul. 2021, pp. 2371-2378, vol. 36(7), Elsevier Inc.
Zhu et al., "Quantification of Pelvic Tilt in Total Hip Arthroplasty," Clinical Orthopaedics and Related Research, Aug. 28, 2009, pp. 571-575, vol. 468(2), Springer.
Ramkumar et al., "Patient-Specific Safe Zones for Acetabular Component Positioning in Total Hip Arthroplasty: Mathematically Accounting for Spinopevlic Biomechanics," The Journal of Arthroplasty, Mar. 16, 2023, pp. 1779-1786, vol. 38, Elsevier Inc.

* cited by examiner

Figure 6B:
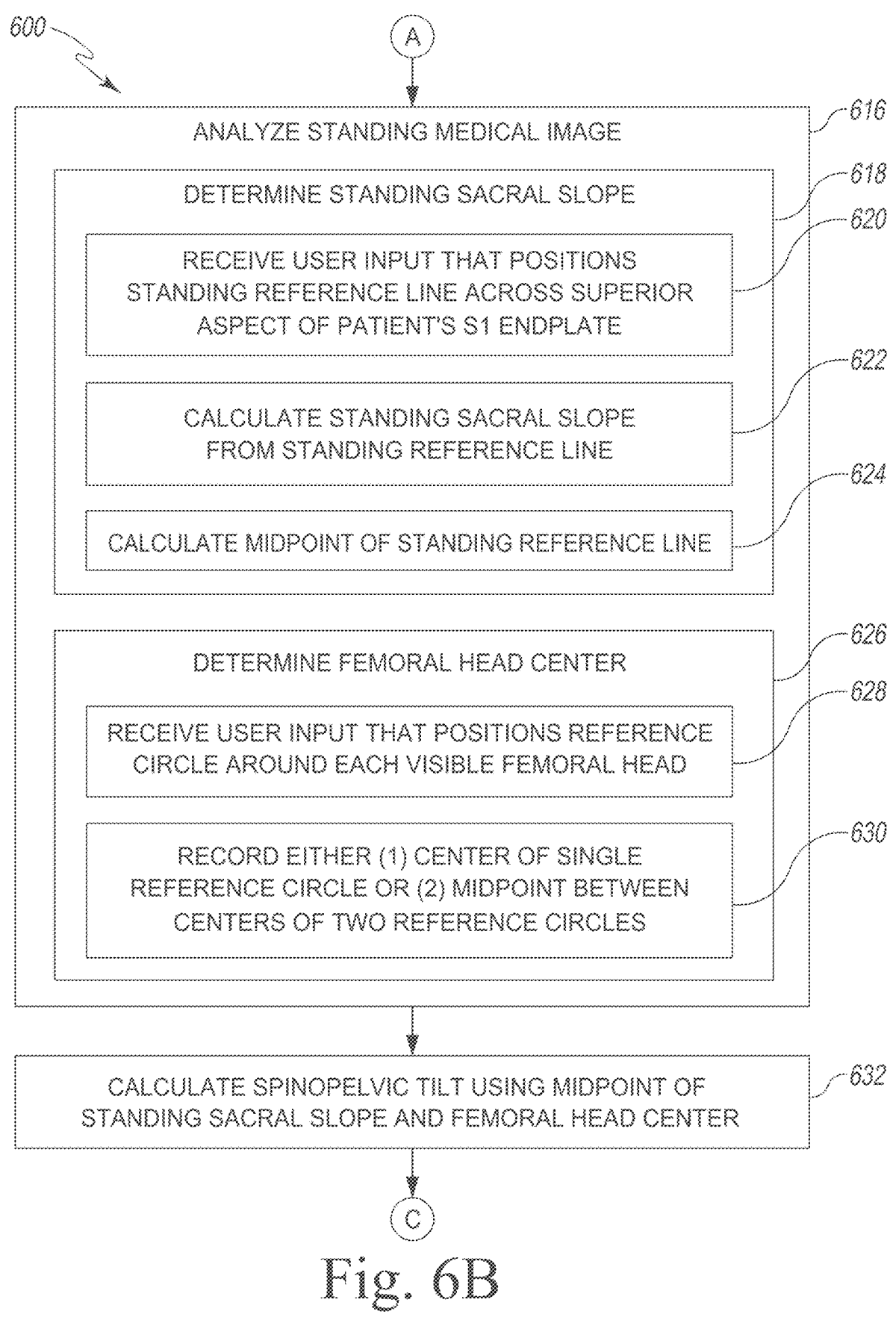

600

A

616 ANALYZE STANDING MEDICAL IMAGE

618 DETERMINE STANDING SACRAL SLOPE

620 RECEIVE USER INPUT THAT POSITIONS STANDING REFERENCE LINE ACROSS SUPERIOR ASPECT OF PATIENT'S S1 ENDPLATE

622 CALCULATE STANDING SACRAL SLOPE FROM STANDING REFERENCE LINE

624 CALCULATE MIDPOINT OF STANDING REFERENCE LINE

626 DETERMINE FEMORAL HEAD CENTER

628 RECEIVE USER INPUT THAT POSITIONS REFERENCE CIRCLE AROUND EACH VISIBLE FEMORAL HEAD

630 RECORD EITHER (1) CENTER OF SINGLE REFERENCE CIRCLE OR (2) MIDPOINT BETWEEN CENTERS OF TWO REFERENCE CIRCLES

632 CALCULATE SPINOPELVIC TILT USING MIDPOINT OF STANDING SACRAL SLOPE AND FEMORAL HEAD CENTER

APPARATUS, SYSTEM, AND METHOD FOR DETERMINING A POSITION OF A HIP PROSTHESIS IN A BONE OF A PATIENT

CROSS-REFERENCE TO RELATED APPLICATIONS

This application claims the benefit of U.S. Provisional Patent Application No. 63/541,603, filed Sep. 29, 2023, and of U.S. Provisional Patent Application No. 63/571,818, filed Mar. 29, 2024. Each of the foregoing applications is incorporated herein by reference in its entirety.

TECHNICAL FIELD

The present disclosure relates generally to computer-assisted surgery systems for use in planning and/or performing orthopaedic procedures and, more particularly, to technologies for determining a position of a hip prosthesis in a bone of a patient.

BACKGROUND

Joint arthroplasty is a well-known surgical procedure by which a diseased and/or damaged natural joint is replaced by a prosthetic joint. For example, in a hip arthroplasty surgical procedure, a patient's natural hip ball and socket joint is partially or totally replaced by a prosthetic hip joint. A typical prosthetic hip joint includes an acetabular cup and a femoral prosthesis. The acetabular cup is implanted into the patient's acetabulum and generally includes an outer shell configured to engage the acetabulum and an inner bearing or cup liner coupled to the shell. The femoral prosthesis is implanted into the patient's femur and generally includes a stem embedded into the medullary canal the femur and a femoral head. The femoral head is configured to engage the cup liner of the acetabular cup to form a ball and socket joint that approximates the natural hip joint.

Typically, an orthopaedic surgeon may perform some amount of pre-operative planning to, for example, determine a position of the hip prosthesis. Such pre-operative planning may be performed manually by the orthopaedic surgeon based on an examination of the patient and/or pre-operative medical images of the patient's bony anatomy. However, such pre-operative planning is typically unable to provide the orthopaedic surgeon with an understanding of the patient hip mechanics, and thereby performance of the hip prosthesis, that may result from the planned position of the hip prosthesis.

SUMMARY

According to one aspect, a method for planning an orthopaedic surgical procedure on a hip of a patient to implant a hip prosthesis having a femoral prosthesis and an acetabular cup may comprise: determining, with a computer system, a first set of target orientations for the acetabular cup when the femoral prosthesis is oriented at a first version; determining, with the computer system, a second set of target orientations for the acetabular cup when the femoral prosthesis is oriented at a second version different from the first version; displaying, with the computer system, a first graphical user interface (GUI) that comprises (i) a first graphic representing the first set of target orientations for the acetabular cup, (ii) a first interface element indicating that the first graphic corresponds to the femoral prosthesis being oriented at the first version, and (iii) a second interface element indicating that the second set of target orientations for the acetabular cup corresponding to the femoral prosthesis being oriented at the second version is available for review; receiving, with the computer system, a user input associated with the second interface element; and displaying, with the computer system and in response to receiving the user input associated with the second interface element, a second GUI that comprises (i) a second graphic representing the second set of target orientations for the acetabular cup, (ii) a third interface element indicating that the second graphic corresponds to the femoral prosthesis being oriented at the second version, and (iii) a fourth interface element indicating that the first set of target orientations for the acetabular cup corresponding to the femoral prosthesis being oriented at the first version is available for review.

In some embodiments, the computer system determines the second set of target orientations for the acetabular cup prior to receiving the user input associated with the second interface element of the first GUI.

In some embodiments, displaying the second GUI comprises updating the first GUI by (i) replacing the first graphic with the second graphic, (ii) replacing the first interface element with the fourth interface element, and (iii) replacing the second interface element with the third interface element.

In some embodiments, determining the first set of target orientations for the acetabular cup when the femoral prosthesis is oriented at the first version comprises determining target orientations for the acetabular cup when the femoral prosthesis is oriented at the same version as the patient's natural femur. In other embodiments, the first version is 15 degrees, and the second version is selected from the group consisting of −5 degrees, 5 degrees, 25 degrees, and 35 degrees.

In some embodiments, the method may further comprise receiving, with the computer system, a user input associated with the fourth interface element and displaying, with the computer system, the first GUI in response to receiving the user input associated with the fourth interface element.

In some embodiments, the method may further comprise: determining, with the computer system, a third set of target orientations for the acetabular cup when the femoral prosthesis is oriented at a third version different from the first version and from the second version; receiving, with the computer system, a user input associated with a fifth interface element included in both the first GUI and the second GUI, the fifth interface element indicating that the third set of target orientations for the acetabular cup corresponding to the femoral prosthesis being oriented at the third version is available for review; and displaying, with the computer system and in response to receiving the user input associated with the fifth interface element, a third GUI that comprises (i) a third graphic representing the third set of target orientations for the acetabular cup, (ii) a sixth interface element indicating that the third graphic corresponds to the femoral prosthesis being oriented at the third version, (iii) the fourth interface element indicating that the first set of target orientations for the acetabular cup corresponding to the femoral prosthesis being oriented at the first version is available for review, and (iv) the second interface element indicating that the second set of target orientations for the acetabular cup corresponding to the femoral prosthesis being oriented at the second version is available for review.

In some embodiments, the method may further comprise determining, with the computer system, that a number of target orientations for the acetabular cup when the femoral prosthesis is oriented at a third version is below an output threshold, the third version being different from the first version and from the second version. In such embodiments, the first GUI may further comprise a fifth interface element indicating that the computer system cannot generate a sufficient set of target orientations for the acetabular cup when the femoral prosthesis is oriented at the third version, and the second GUI may also comprise the fifth interface element.

In some embodiments, the first graphic comprises an inclination axis, a version axis, and a first closed shape surrounding the first set of target orientations for the acetabular cup when graphed relative to the inclination and version axes. In some embodiments, the second graphic comprises the inclination axis, the version axis, and a second closed shape surrounding the second set of target orientations for the acetabular cup when graphed relative to the inclination and version axes.

In some embodiments, the first graphic further comprises a marker indicating a centroid of the first closed shape. In some embodiments, the second graphic further comprises a marker indicating a centroid of the second closed shape.

In some embodiments, the first graphic further comprises a first line representing a first target boundary when graphed relative to the inclination and version axes. In some embodiments, the second graphic also comprises the first line. In some embodiments, the first line intersects at least one of (i) the first closed shape in the first graphic and (ii) the second closed shape in the second graphic. In some embodiments, portions of the first and second closed shapes that are inside of the first target boundary are visually distinct from portions of the first and second closed shapes that are outside of the first target boundary. In some embodiments, the first line is positioned in each of the first and second graphics based on patient-specific pelvic tilt measurements. In some embodiments, the first line is curved to reflect a non-linear relationship between pelvic tilt, acetabular cup inclination, and acetabular cup version. In other embodiments, the first line is straight but approximates the relationship between pelvic tilt, acetabular cup inclination, and acetabular cup version. In some embodiments, the first target boundary is based on a minimum or maximum allowable version for the acetabular cup in a particular functional position of the patient. In some embodiments, the minimum or maximum allowable version for the acetabular cup in a particular functional position of the patient is user-defined. In other embodiments, the minimum or maximum allowable version for the acetabular cup in a particular functional position of the patient is predefined using a value taken from medical literature.

In some embodiments, the first graphic further comprises a second line representing a second target boundary when graphed relative to the inclination and version axes. In some embodiments, the second graphic also comprises the second line. In some embodiments, the second line intersects at least one of (i) the first closed shape in the first graphic and (ii) the second closed shape in the second graphic. In some embodiments, portions of the first and second closed shapes that are inside of both the first target boundary and the second target boundary are visually distinct from portions of the first and second closed shapes that are outside of either the first target boundary or the second target boundary. In some embodiments, the second line is positioned in each of the first and second graphics based on patient-specific pelvic tilt measurements. In some embodiments, the first target boundary is based on a minimum allowable version for the acetabular cup in a first functional position of the patient, and the second target boundary is based on a maximum allowable version for the acetabular cup in a second functional position of the patient different than the first functional position. In some embodiments, the minimum allowable version for the acetabular cup is 10 degrees while the first functional position is a flexed seated position, and the maximum allowable version for the acetabular cup is 30 degrees while the second functional position is a standing position.

In some embodiments, determining the first set of target orientations for the acetabular cup comprises predicting a set of orientations for the acetabular cup that will not result in either edge loading of the acetabular cup by the femoral prosthesis or impingement of the femoral prosthesis and the acetabular cup when the femoral prosthesis is oriented at the first version. In some embodiments, determining the second set of target orientations for the acetabular cup comprises predicting a set of orientations for the acetabular cup that will not result in either edge loading of the acetabular cup by the femoral prosthesis or impingement of the femoral prosthesis and the acetabular cup when the femoral prosthesis is oriented at the second version.

In some embodiments, predicting a set of orientations for the acetabular cup that will not result in either edge loading of the acetabular cup by the femoral prosthesis or impingement of the femoral prosthesis and the acetabular cup when the femoral prosthesis is oriented at the first or second version comprises: operating a first mathematical model with a set of candidate orientations for the acetabular cup, patient-specific pelvic tilt measurements, and type and size data for the hip prosthesis as inputs to the first mathematical model to generate, for each candidate orientation for the acetabular cup, predicted distances between (i) an edge of a cup liner of the acetabular cup and (ii) contact between the cup liner and a femoral head of the femoral prosthesis in each of a plurality of different functional positions of the patient; selecting the candidate orientations for the acetabular cup for which each of the predicted distances is greater than a distance threshold; operating a second mathematical model with the selected candidate orientations for the acetabular cup, the patient-specific pelvic tilt measurements, the type and size data for the hip prosthesis, and a corresponding version of the femoral prosthesis as inputs to the second mathematical model to generate, for each selected candidate orientation for the acetabular cup, predicted amounts of femoral prosthesis rotation until impingement of the femoral prosthesis and the acetabular cup in each of the plurality of different functional positions of the patient; and identifying the selected candidate orientations for the acetabular cup for which each of the predicted amounts of femoral prosthesis rotation is greater than a rotation threshold as the set of orientations for the acetabular cup predicted to not result in either edge loading of the acetabular cup by the femoral prosthesis or impingement of the femoral prosthesis and the acetabular cup when the femoral prosthesis is oriented at the corresponding version.

In some embodiments, determining the first set of target orientations for the acetabular cup further comprises removing orientations for the acetabular cup that do not satisfy one or more target boundaries from the set of orientations for the acetabular cup predicted to not result in either edge loading of the acetabular cup by the femoral prosthesis or impingement of the femoral prosthesis and the acetabular cup when the femoral prosthesis is oriented at the first version, such that the orientations for the acetabular cup that do not satisfy the one or more target boundaries are not included in the first set of target orientations for the acetabular cup.

In some embodiments, determining the second set of target orientations for the acetabular cup further comprises removing orientations for the acetabular cup that do not satisfy the one or more target boundaries from the set of orientations for the acetabular cup predicted to not result in either edge loading of the acetabular cup by the femoral prosthesis or impingement of the femoral prosthesis and the acetabular cup when the femoral prosthesis is oriented at the second version, such that the orientations for the acetabular cup that do not satisfy the one or more target boundaries are not included in the second set of target orientations for the acetabular cup.

In some embodiments, each of the one or more target boundaries is based on a corresponding minimum or maximum allowable version for the acetabular cup in a corresponding functional position of the patient that has been converted into a frame of reference of the first and second sets of target orientations for the acetabular cup using patient-specific pelvic tilt measurements. In some embodiments, the one or more target boundaries comprise a first target boundary based on a minimum allowable version for the acetabular cup in a first functional position of the patient. In some embodiments, the one or more target boundaries comprise a second target boundary based on a maximum allowable version for the acetabular cup in a second functional position of the patient different than the first functional position. In some embodiments, the first target boundary requires the acetabular cup to have at least 10 degrees of version when the patient is in a flexed seated position. In some embodiments, the second target boundary requires the acetabular cup to have no more than 30 degrees of version when the patient is in a standing position. In some embodiments, the one or more target boundaries each reflect a non-linear relationship between pelvic tilt, acetabular cup inclination, and acetabular cup version.

According to another aspect, a method for planning an orthopaedic surgical procedure on a hip of a patient to implant a hip prosthesis having a femoral prosthesis and an acetabular cup may comprise: predicting, with a computer system, a set of target orientations for the acetabular cup that will not result in either edge loading of the acetabular cup by the femoral prosthesis or impingement of the femoral prosthesis and the acetabular cup; determining, with the computer system, a target boundary by converting a minimum or maximum allowable version for the acetabular cup in a functional position of the patient into a frame of reference of the set of target orientations for the acetabular cup using patient-specific pelvic tilt measurements; and displaying, with the computer system, a graphic comprising an inclination axis, a version axis, a closed shape surrounding the set of target orientations for the acetabular cup when graphed relative to the inclination and version axes, and a line representing the target boundary when graphed relative to the inclination and version axes.

In some embodiments, the line intersects the closed shape in the graphic, and a portion of the closed shape that is inside of the target boundary is visually distinct from a portion of the closed shape that is outside of the target boundary. In some embodiments, the line is curved to reflect a non-linear relationship between pelvic tilt, acetabular cup inclination, and acetabular cup version.

According to yet another aspect, a method for planning an orthopaedic surgical procedure on a hip of a patient to implant a hip prosthesis having a femoral prosthesis and an acetabular cup may comprise: predicting, with a computer system, a set of target orientations for the acetabular cup that will not result in either edge loading of the acetabular cup by the femoral prosthesis or impingement of the femoral prosthesis and the acetabular cup; determining, with the computer system, a first target boundary by converting a minimum allowable version for the acetabular cup in a first functional position of the patient into a frame of reference of the set of target orientations for the acetabular cup using patient-specific pelvic tilt measurements; determining, with the computer system, a second target boundary by converting a maximum allowable version for the acetabular cup in a second functional position of the patient into the frame of reference of the set of target orientations for the acetabular cup using the patient-specific pelvic tilt measurements; and displaying, with the computer system, a graphic comprising an inclination axis, a version axis, a closed shape surrounding the set of target orientations for the acetabular cup when graphed relative to the inclination and version axes, a first line representing the first target boundary when graphed relative to the inclination and version axes, and a second line representing the first target boundary when graphed relative to the inclination and version axes.

In some embodiments, at least one of the first line and the second line intersects the closed shape in the graphic, and a portion of the closed shape that is inside of both the first target boundary and the second target boundary is visually distinct from each portion of the closed shape that is outside of either the first target boundary or the second target boundary. In some embodiments, the first and second lines are each curved to reflect a non-linear relationship between pelvic tilt, acetabular cup inclination, and acetabular cup version. In some embodiments, the first target boundary reflects a minimum allowable version for the acetabular cup of 10 degrees while the first functional position is a flexed seated position. In some embodiments, the second target boundary reflects a maximum allowable version for the acetabular cup of 30 degrees while the second functional position is a standing position. In some embodiments, the graphic further comprises a marker indicating a centroid of the closed shape.

In some embodiments, predicting the set of target orientations for the acetabular cup that will not result in either edge loading of the acetabular cup by the femoral prosthesis or impingement of the femoral prosthesis and the acetabular cup comprises: operating a first mathematical model with a set of candidate orientations for the acetabular cup, patient-specific pelvic tilt measurements, and type and size data for the hip prosthesis as inputs to the first mathematical model to generate, for each candidate orientation for the acetabular cup, predicted distances between (i) an edge of a cup liner of the acetabular cup and (ii) contact between the cup liner and a femoral head of the femoral prosthesis in each of a plurality of different functional positions of the patient; selecting the candidate orientations for the acetabular cup for which each of the predicted distances is greater than a distance threshold; operating a second mathematical model with the selected candidate orientations for the acetabular cup, the patient-specific pelvic tilt measurements, and the type and size data for the hip prosthesis as inputs to the second mathematical model to generate, for each selected candidate orientation for the acetabular cup, predicted amounts of femoral prosthesis rotation until impingement of the femoral prosthesis and the acetabular cup in each of the plurality of different functional positions of the patient; and identifying the selected candidate orientations for the acetabular cup for which each of the predicted amounts of femoral prosthesis rotation is greater than a rotation threshold as the set of target orientations for the acetabular cup.

According to still another aspect, a method for planning an orthopaedic surgical procedure on a hip of a patient to implant a hip prosthesis having a femoral prosthesis and an acetabular cup may comprise: predicting, with a computer system, a first set of orientations for the acetabular cup that will not result in either edge loading of the acetabular cup by the femoral prosthesis or impingement of the femoral prosthesis and the acetabular cup; determining, with the computer system, a second set of target orientations for the acetabular cup by removing orientations that do not satisfy one or more target boundaries from the first set of orientations; and displaying, with the computer system, a graphic that comprises an inclination axis, a version axis, and a closed shape surrounding the second set of orientations for the acetabular cup when graphed relative to the inclination and version axes.

In some embodiments, predicting the first set of orientations for the acetabular cup that will not result in either edge loading of the acetabular cup by the femoral prosthesis or impingement of the femoral prosthesis and the acetabular cup comprises: operating a first mathematical model with a set of candidate orientations for the acetabular cup, patient-specific pelvic tilt measurements, and type and size data for the hip prosthesis as inputs to the first mathematical model to generate, for each candidate orientation for the acetabular cup, predicted distances between (i) an edge of a cup liner of the acetabular cup and (ii) contact between the cup liner and a femoral head of the femoral prosthesis in each of a plurality of different functional positions of the patient; selecting the candidate orientations for the acetabular cup for which each of the predicted distances is greater than a distance threshold; operating a second mathematical model with the selected candidate orientations for the acetabular cup, the patient-specific pelvic tilt measurements, and the type and size data for the hip prosthesis as inputs to the second mathematical model to generate, for each selected candidate orientation for the acetabular cup, predicted amounts of femoral prosthesis rotation until impingement of the femoral prosthesis and the acetabular cup in each of the plurality of different functional positions of the patient; and identifying the selected candidate orientations for the acetabular cup for which each of the predicted amounts of femoral prosthesis rotation is greater than a rotation threshold as the first set of orientations for the acetabular cup.

In some embodiments, the graphic further comprises a marker indicating a centroid of the closed shape. In some embodiments, each of the one or more target boundaries is based on a corresponding minimum or maximum allowable version for the acetabular cup in a corresponding functional position of the patient that has been converted into a frame of reference of the first and second sets of orientations for the acetabular cup using patient-specific pelvic tilt measurements. In some embodiments, the one or more target boundaries comprise a first target boundary based on a minimum allowable version for the acetabular cup in a first functional position of the patient. In some embodiments, the one or more target boundaries comprise a second target boundary based on a maximum allowable version for the acetabular cup in a second functional position of the patient different than the first functional position. In some embodiments, the first target boundary requires the acetabular cup to have at least 10 degrees of version when the patient is in a flexed seated position. In some embodiments, the second target boundary requires the acetabular cup to have no more than 30 degrees of version when the patient is in a standing position. In some embodiments, the one or more target boundaries each reflect a non-linear relationship between pelvic tilt, acetabular cup inclination, and acetabular cup version.

In some embodiments, when the second set of target orientations for the acetabular cup is a null set, the graphic further comprises at least one of (i) a closed shape surrounding the first set of orientations for the acetabular cup when graphed relative to the inclination and version axes and (ii) one or more lines representing the one or more target boundaries when graphed relative to the inclination and version axes, according to a user-defined preference.

According to another aspect, a method for planning an orthopaedic surgical procedure on a hip of a patient to implant a hip prosthesis having a femoral prosthesis and an acetabular cup may comprise: operating, with a computer system, a first mathematical model with a set of candidate orientations for the acetabular cup, patient-specific pelvic tilt measurements, and type and size data for the hip prosthesis as inputs to the first mathematical model to generate, for each candidate orientation for the acetabular cup, predicted distances between (i) an edge of a cup liner of the acetabular cup and (ii) contact between the cup liner and a femoral head of the femoral prosthesis in each of a plurality of different functional positions of the patient; selecting, with the computer system, the candidate orientations for the acetabular cup for which each of the predicted distances is greater than a distance threshold; operating, with the computer system, a second mathematical model with the selected candidate orientations for the acetabular cup, the patient-specific pelvic tilt measurements, the type and size data for the hip prosthesis, and a planned version for the femoral prosthesis as inputs to the second mathematical model to generate, for each selected candidate orientation for the acetabular cup, predicted amounts of femoral prosthesis rotation until impingement of the femoral prosthesis and the acetabular cup in each of the plurality of different functional positions of the patient; identifying, with the computer system, the selected candidate orientations for the acetabular cup for which each of the predicted amounts of femoral prosthesis rotation is greater than a rotation threshold as a set of target orientations for the acetabular cup predicted to not result in either edge loading of the acetabular cup by the femoral prosthesis or impingement of the femoral prosthesis and the acetabular cup when the femoral prosthesis is oriented at the planned version; and providing, with the computer system, a user interface that presents the set of target orientations for the acetabular cup to an orthopaedic surgeon.

In some embodiments, the method may further comprise measuring, with the computer system, a pre-operative version of the patient's natural femur from one or more medical images, and using the measured pre-operative version as the planned version for the femoral prosthesis when operating the second mathematical model.

In some embodiments, identifying the selected candidate orientations for the acetabular cup for which each of the predicted amounts of femoral prosthesis rotation is greater than a rotation threshold comprises: determining a first number of selected candidate orientations for the acetabular cup for which each of the predicted amounts of femoral prosthesis rotation is greater than a first rotation threshold; and, in response to the first number being less than a size threshold for the set of target orientations for the acetabular cup, determining a second number of selected candidate orientations for the acetabular cup for which each of the predicted amounts of femoral prosthesis rotation is greater than a second rotation threshold, the second rotation threshold being less than the first rotation threshold.

In some embodiments, the user interface comprises a graphic including an inclination axis, a version axis, and a closed shape surrounding the set of target orientations for the acetabular cup when graphed relative to the inclination and version axes. In some embodiments, the graphic further includes a marker indicating a centroid of the closed shape. In some embodiments, the method further comprises receiving, via the user interface, an input indicating a planned orientation for the acetabular cup selected by the orthopaedic surgeon, and the graphic further includes a marker representing the planned orientation for the acetabular cup when graphed relative to the inclination and version axes.

In some embodiments, the method may further comprise: detecting, with the computer system, during the orthopaedic surgical procedure, an actual orientation of the acetabular cup relative to an acetabulum of the patient; and presenting, via the user interface, during the orthopaedic surgical procedure, a comparison of the actual orientation of the acetabular cup to the set of target orientations for the acetabular cup. In some embodiments, the user interface comprises a graphic including an inclination axis, a version axis, a closed shape surrounding the set of target orientations for the acetabular cup when graphed relative to the inclination and version axes, and a marker representing the actual orientation of the acetabular cup when graphed relative to the inclination and version axes.

According to yet another aspect, a method for planning an orthopaedic surgical procedure involving a patient's pelvis may comprise: acquiring, by a computer system, a standing medical image showing a sagittal profile of the patient's pelvis in a standing position; acquiring, by the computer system, a seated medical image showing a sagittal profile of the patient's pelvis in a seated position; determining, with the computer system, a standing sacral slope value from the standing medical image; determining, with the computer system, a seated sacral slope value from the seated medical image; calculating, with the computer system, a pelvic mobility value as a difference between the standing sacral slope value and the seated sacral slope value; and generating, with the computer system, a user alert in response to the calculated pelvic mobility value being outside of a predetermined range.

In some embodiments, generating the user alert comprises displaying a message on the computer system that indicates the patient has a stiff spine in response to the calculated pelvic mobility value being less than a lower end of the predetermined range. In some embodiments, generating the user alert comprises displaying a message on the computer system that indicates the patient has a hypermobile spine in response to the calculated pelvic mobility value being greater than an upper end of the predetermined range. In some embodiments, each of the standing sacral slope value, the seated sacral slope value, and the pelvic mobility value is an angle expressed in degrees. In some embodiments, the lower end of the predetermined range is 10 degrees. In some embodiments, the upper end of the predetermined range is 35 degrees.

In some embodiments, determining the standing sacral slope value from the standing medical image comprises receiving one or more user inputs that position a standing reference line across a superior aspect of the patient's S1 endplate shown in the standing medical image and calculating the standing sacral slope value as the inverse tangent of a slope of the standing reference line positioned by the user. In some embodiments, determining the seated sacral slope value from the seated medical image comprises receiving one or more user inputs that position a seated reference line across the superior aspect of the patient's S1 endplate shown in the seated medical image and calculating the seated sacral slope value as the inverse tangent of a slope of the seated reference line positioned by the user.

According to still another aspect, a method for planning an orthopaedic surgical procedure involving a patient's pelvis may comprise: acquiring, by a computer system, a standing medical image showing a sagittal profile of the patient's pelvis in a standing position; determining, with the computer system, a sacral slope value, a sacral slope midpoint, and a femoral head center from the standing medical image; calculating, with the computer system, a spinopelvic tilt value using the sacral slope midpoint and the femoral head center; calculating, with the computer system, a pelvic incidence value as a sum of the sacral slope value and the spinopelvic tilt value; and generating, with the computer system, a user alert in response to the calculated pelvic incidence value being outside of a predetermined range.

In some embodiments, generating the user alert comprises displaying a message on the computer system that suggests a surgeon intra-operatively assess the patient's risk of bone-on-bone impingement. In some embodiments, the message is displayed on the computer system during the orthopaedic surgical procedure. In some embodiments, each of the sacral slope value, the spinopelvic tilt value, and the pelvic incidence value is an angle expressed in degrees. In some embodiments, the predetermined range is 45-65 degrees.

In some embodiments, determining the sacral slope value and the sacral slope midpoint from the standing medical image comprises: receiving one or more user inputs that position a reference line across a superior aspect of the patient's S1 endplate shown in the standing medical image; calculating the sacral slope value as the inverse tangent of a slope of the reference line positioned by the user; and calculating the sacral slope midpoint as the midpoint of the reference line positioned by the user.

In some embodiments, calculating the spinopelvic tilt value using the sacral slope midpoint and the femoral head center comprises calculating the inverse tangent of a slope of a derived line defined by the sacral slope midpoint and the femoral head center.

In some embodiments, determining the femoral head center from the standing medical image comprises receiving one or more user inputs that position a reference circle around a femoral head of the patient shown in the standing medical image and recording a center of the reference circle positioned by the user as the femoral head center. In other embodiments, determining the femoral head center from the standing medical image comprises: receiving one or more user inputs that position (i) a first reference circle around a first femoral head of the patient shown in the standing medical image and (ii) a second reference circle around a second femoral head of the patient shown in the standing medical image; determining a femoral head midpoint between (i) a center of the first reference circle positioned by the user and (i) a center of the second reference circle positioned by the user; and recording the femoral head midpoint as the femoral head center.

BRIEF DESCRIPTION OF THE DRAWINGS

The detailed description particularly refers to the following figures, in which:

FIGS. 6A-6C are a flow chart diagram of a method for determining patient-specific pelvic tilt measurements, which may be executed by the computer system of FIG. 4 or the computer system of FIG. 5;

DETAILED DESCRIPTION OF THE DRAWINGS

Figure 1:
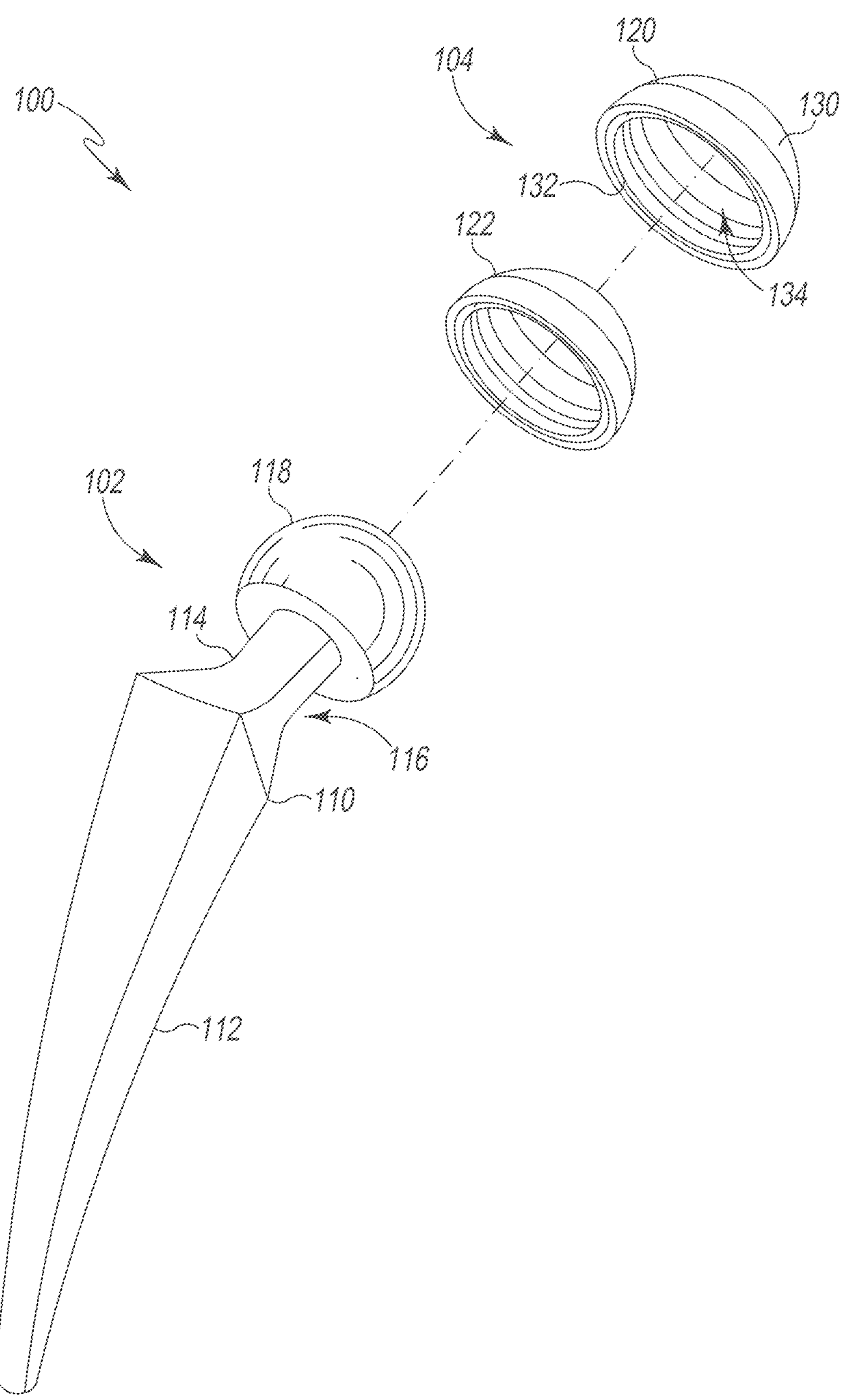
FIG. 1 is an exploded, perspective view of an embodiment of a hip prosthesis including a femoral prosthesis and an acetabular cup.

While the concepts of the present disclosure are susceptible to various modifications and alternative forms, specific illustrative embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopaedics. Use of such anatomical reference terms in the written description and claims is intended to be consistent with their well-understood meanings unless noted otherwise.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, an illustrative hip orthopaedic prosthesis 100 includes a femoral prosthesis 102 and an acetabular cup 104. In use, as discussed in more detail below, the hip orthopaedic prosthesis 100 is configured to replace a natural hip joint of the patient. To do so, the femoral prosthesis 102 is configured to be implanted in the proximal end of a surgically-prepared femur of a patient, and the acetabular cup 104 is configured to be implanted into a surgically-prepared acetabulum of the patient's pelvis. Once so implanted, the femoral prosthesis 102 is supported by the acetabular cup 104, and the femoral prosthesis 102 and the acetabular cup 104 cooperate to form a prosthetic hip joint for the patient.

The illustrative femoral prosthesis 102 includes a stem 110 having an elongated distal end 112 and a neck 114 located at a proximal end 116. The elongated distal end 112 is sized and shaped to be implanted into a medullary canal of the patient's femur to secure the femoral prosthesis 102 thereto. The femoral prosthesis 102 also includes a femoral head 118 secured to the neck 114 of the stem 110. The femoral head 118 is substantially spherical in shape and is configured to be received in the acetabular cup 104 to form an artificial ball-and-socket joint of the patient's hip. The stem 110 and the femoral head 118 may be separately formed from implant-grade metallic materials such as, for example, cobalt chromium. In some embodiments, the stem 110 may also include an outer coating, such as a Porocoat® outer coating, that facilitates bone ingrowth to permit the patient's bone to affix biologically to the stem 110 after implantation.

The acetabular cup 104 includes an acetabular shell 120 and an acetabular cup liner 122 configured to be received in the acetabular shell 120. The acetabular shell 120 has a generally hemispherical shape and includes a convex outer wall 130 and a concave inner wall 132 opposite the convex outer wall 130. The inner wall 132 defines a hemispherical recess 134 that is shaped and sized to receive the acetabular cup liner 122 to form the assembled acetabular cup 104. The acetabular shell 120 may be formed from any suitable implant-grade metallic material such as, for example, a titanium alloy. Similar to the stem 110 of the femoral prosthesis 102, the outer wall 130 of the acetabular shell 120 may include an outer coating, such as a Porocoat® outer coating, that facilitates bone ingrowth to permit the patient's bone to affix biologically to the acetabular shell 120 after implantation. As discussed above, the acetabular cup liner 122 is configured to be received in the hemispherical recess 134 of the acetabular shell 120 and is illustratively formed from a polymeric material such as, for example, polyethylene. Of course, in other embodiments, the acetabular cup liner 122 may be formed from other materials, such as a ceramic material or the like. While the illustrative acetabular cup 104 includes a single liner 122, it is contemplated that other embodiments may include multiple liners 122 (sometimes referred to as "dual mobility implants").

Figure 2:
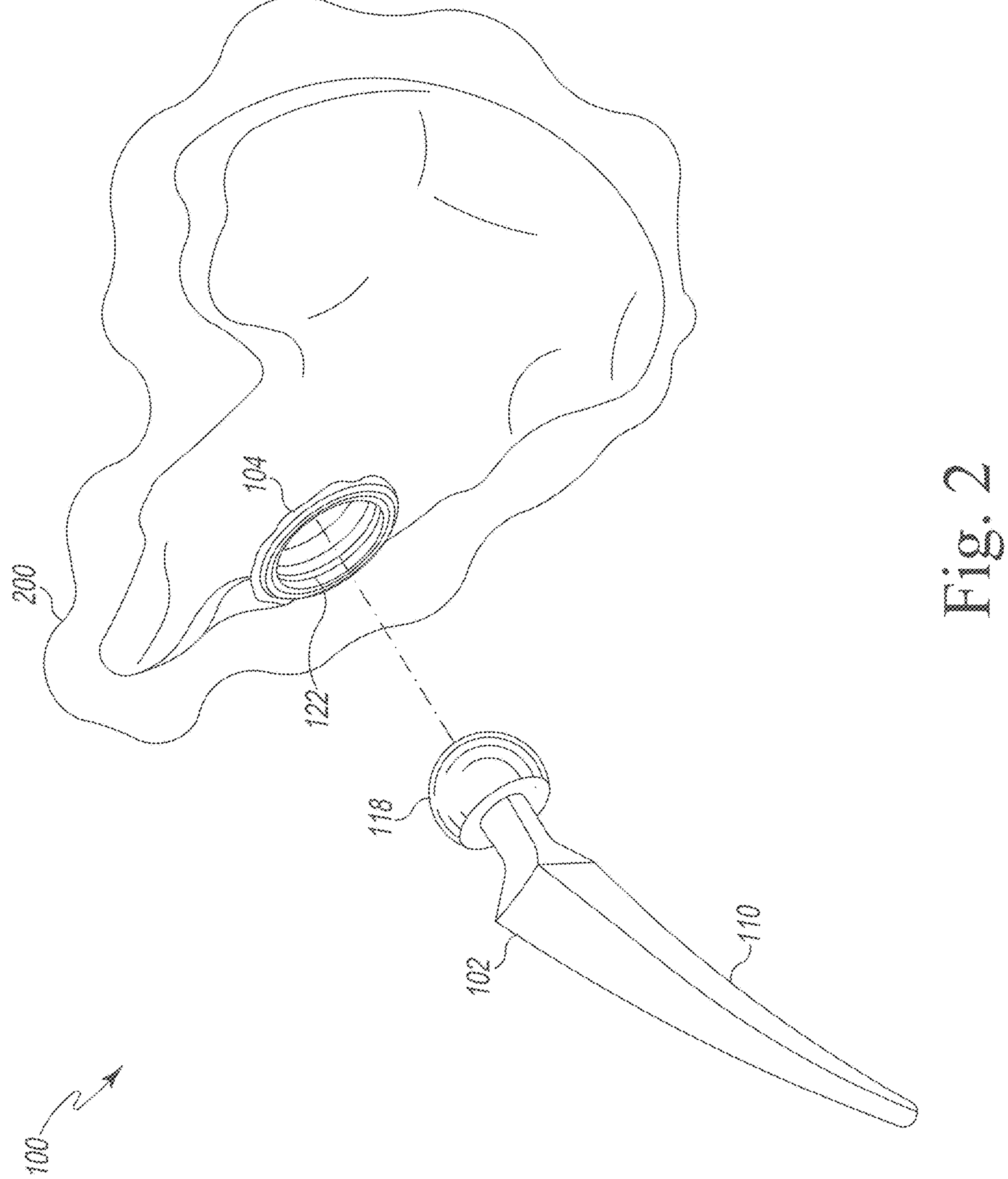
FIG. 2 is another perspective view of the hip prosthesis of FIG. 1 having the acetabular cup implanted into an acetabulum of a patient.

As shown in FIG. 2, during performance of the orthopaedic surgical procedure, an orthopaedic surgeon implants the acetabular cup 104 into an acetabulum 200 of the patient to replace the patient's natural "socket" of the patient's corresponding hip joint. In doing so, the orthopaedic surgeon may prepare the patent's acetabulum 200 (e.g., by reaming the acetabulum) and implant the acetabular shell 120 of the acetabular cup 104 into the surgically-prepared acetabulum 200 based on a pre-operative or intra-operative plan as discussed in more detail below. In doing so, the outer wall 130 of the acetabular shell 120 contacts or confronts the prepared bone of the patient's acetabulum 200. The orthopaedic surgeon may then insert the acetabular cup liner 122 into the hemispherical recess 134 of the acetabular shell 120 to form the implanted, assembled acetabular cup 104.

The orthopaedic surgeon also prepares the proximal end of the patient's femur (not shown) for implantation of the femoral prosthesis 102. Such surgical preparation may include resecting a portion of proximal end of the patient's femur (e.g., removing the natural femoral head of the patient's femur) and preparing the medullary canal of the patient's femur to receive the stem 110 of the femoral prosthesis 102.

Figure 3:
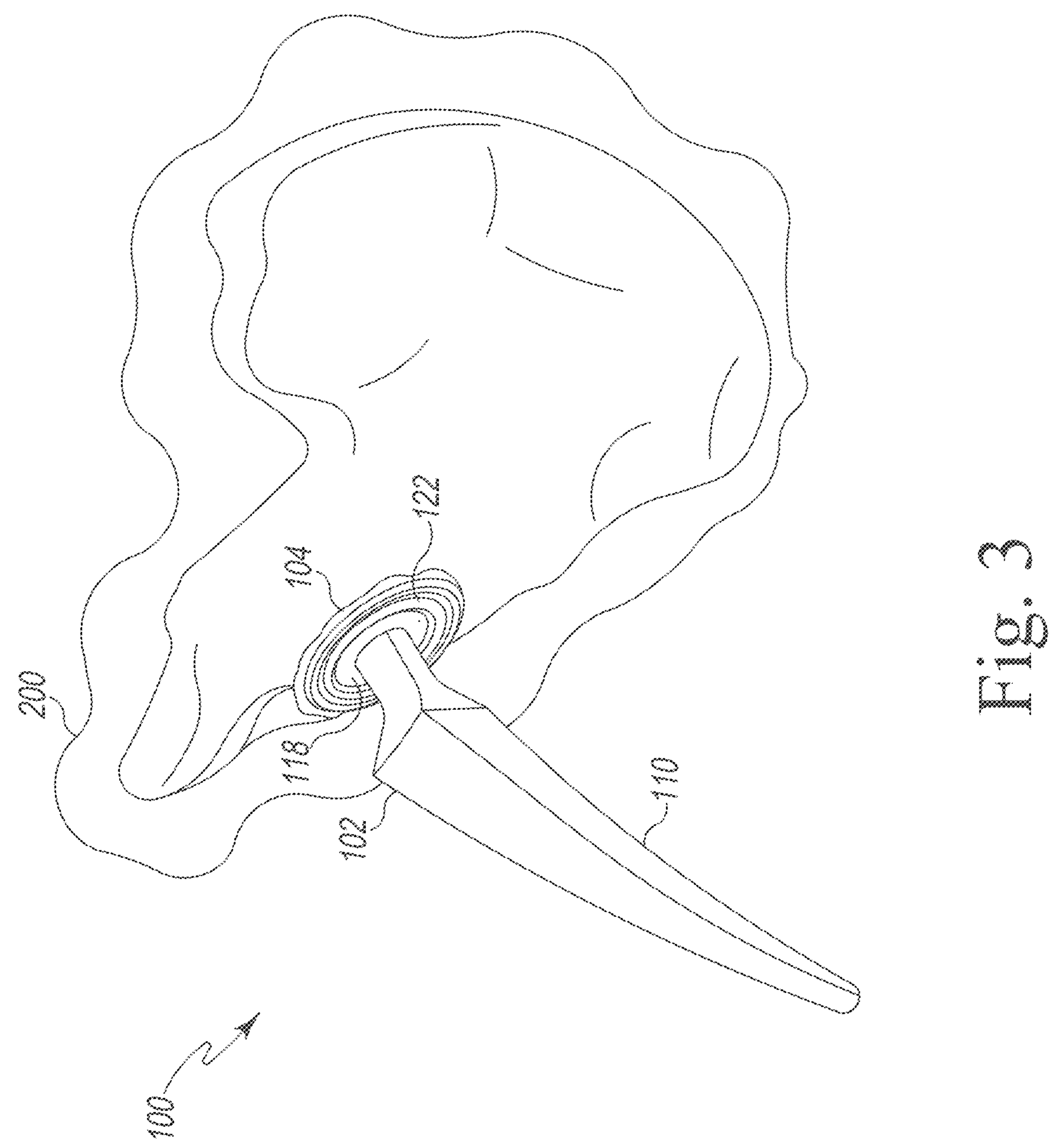
FIG. 3 is another perspective view of the hip prosthesis of FIG. 2 showing the femoral prosthesis engaged with the acetabular cup.

After the femoral prosthesis 102 and the acetabular cup 104 have been implanted into the corresponding bony anatomy of the patient, the orthopaedic surgeon may insert the femoral head 118 of the femoral prosthesis 102 into the acetabular cup liner 122 as shown in FIG. 3. In this way, the femoral prosthesis 102 and the acetabular cup 104 form a prosthetic hip joint for the patient. However, the functionally of the hip prosthesis 100 is dependent, at least in part, on the proper positioning of the acetabular cup 104 into the patient's acetabulum 200. That is, the orientation of the acetabular cup 104 relative to the patient's acetabulum 200 (i.e., the degrees of anteversion and inclination) impacts the performance the hip prosthesis 100. For example, if the orientation of the acetabular cup 104 relative to the patient's acetabulum 200 is not properly chosen and subsequently achieved, the femoral prosthesis 102 may exhibit an amount of edge loading on the acetabular cup liner 122 of the acetabular cup 104. Such edge loading of the acetabular cup 104 can be associated with a higher risk of dislocation of the femoral prosthesis 102 from the acetabular cup 104 during normal activities of the patient. Additionally, the risk of dislocation may be increased if a portion of the femoral prosthesis 102 other than the bearing surface of the femoral head 118 (such as the stem 116) impinges on or comes into contact with any portion of the acetabular cup 102 (including the shell 120 and/or the liner 122). Accordingly, determination of a suitable orientation of the acetabular cup 104 having a reduced risk of such impingement and/or reduced or minimal edge loading may improve the performance of the hip prosthesis 100 and reduce the likelihood of dislocation of the femoral prosthesis 102 from the acetabular cup 104.

Figure 4:
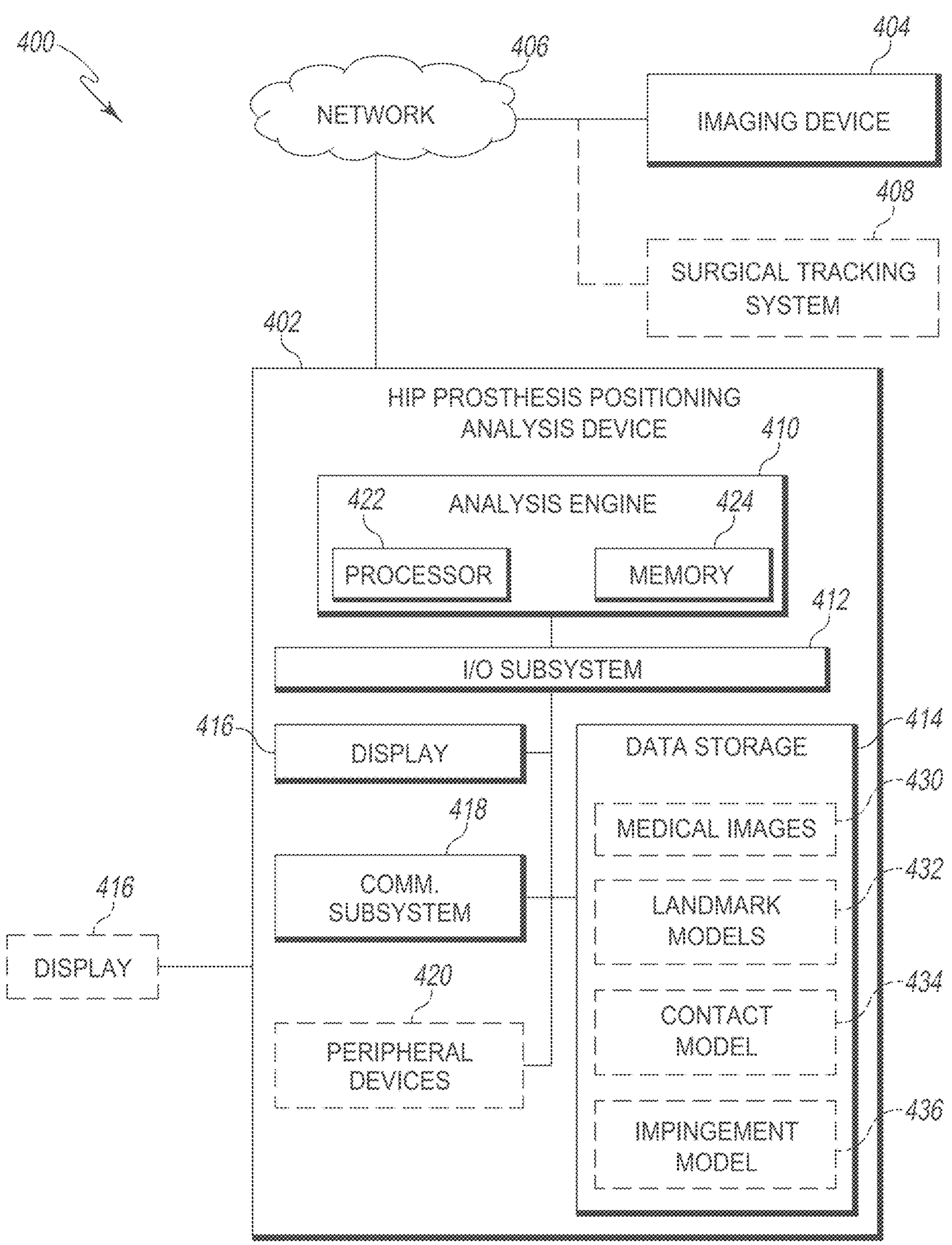
FIG. 4 is a block diagram of an embodiment of a computer system for determining a position of a hip prosthesis (such as the hip prosthesis of FIG. 1) in a bone of a patient.

Referring now to FIG. 4, an illustrative computer system 400 for determining a position of a hip prosthesis, such as the hip prosthesis 100, includes a hip prosthesis positioning analysis device 402 and an imaging device 404 communicatively coupled to the analysis device 402 over a network 406. In use, as discussed in more detail below, an orthopedic surgeon may operate the analysis device 402 to plan an orientation for the acetabular cup 104 relative to the patient's acetabulum 200. In addition to the features and functionality described below, the computer system 400 may also include any of the features and functionality described in U.S. Patent Application Publication Nos. 2022/0202494 and 2022/0202503, both published on Jun. 30, 2022, and in PCT International Publication No. WO 2022/144448, published on Jul. 7, 2022, the entire disclosures of which are incorporated herein by reference.

The hip prosthesis positioning analysis device 402 may be embodied as any type of computer or computation device capable of performing the functions described herein. For example, the analysis device 402 may be embodied as a desktop computer, a surgical navigation computer, a laptop computer, a tablet computer, a smartphone, a mobile computer, a smart device, a wearable computer system, or other computer or computer device. As shown in FIG. 4, the illustrative analysis device 402 includes an analysis engine 410, an input/output ("I/O") subsystem 412, a data storage 414, a display 416, a communication system 418 and, in some embodiments, one or more peripheral devices 420. Of course, the analysis device 402 may include additional or other components, such as those commonly found in a typical computer device, in other embodiments. Additionally, in some embodiments, one or more of the illustrative components may be incorporated in, or otherwise form a portion of, another component.

The analysis engine 410 may be embodied as any type of controller, functional block, digital logic, or other component, device, circuitry, or collection thereof capable of performing the functions described herein. In illustrative embodiment, the analysis engine 410 includes a processor 422 and a memory 424. The processor 422 may be embodied as any type of processor capable of performing the functions described herein. For example, the processor 422 may be embodied as a single or multi-core processor(s), digital signal processor, microcontroller, or other processor or processing/controlling circuit. Similarly, the memory 424 may be embodied as any type of volatile and/or non-volatile memory or data storage capable of performing the functions described herein. In operation, the memory 424 may store various data and software used during operation of the analysis device 402 such as operating systems, applications, executable software, programs, libraries, and drivers, which may be executed or otherwise used by the processor 422.

The analysis engine 410 is communicatively coupled to other components of the analysis device 402 via the I/O subsystem 412, which may be embodied as circuitry and/or components to facilitate input/output operations between the analysis engine 410 (e.g., the processor 422 and the memory 424) and the other components of the analysis device 402. For example, the I/O subsystem 412 may be embodied as, or otherwise include, memory controller hubs, input/output control hubs, firmware devices, communication links (i.e., point-to-point links, bus links, wires, cables, light guides, printed circuit board traces, etc.) and/or other components and subsystems to facilitate the input/output operations. In some embodiments, the I/O subsystem 412 may form a portion of a system-on-a-chip (SoC) and be incorporated, along with the analysis engine 410 (e.g., the processor 422 and the memory 424) and other components of the analysis engine 410, on a single integrated circuit chip. Additionally, in some embodiments, the memory 424, or portions of the memory 424, may be incorporated into the processor 422.

The data storage 414 may be embodied as any type of device or devices configured for short-term and/or long-term storage of data such as, for example, solid-state drives, hard disk drives, memory devices and circuits, memory cards, non-volatile flash memory, or other data storage devices. In the illustrative embodiment, the data storage 414 stores various data used by the analysis device 402 to perform the functions described herein. For example, the data storage 414 may store one or more medical images 430 of the patient. The medical images 430 may be generated by the imaging device 404 and transmitted to the analysis device 402 over the network 406 for local storage in the data storage 414. As discussed in more detail below, the medical images may be embodied as X-ray images, computed tomography (CT) images, magnetic resonance imaging (MRI) images, or other medical images of the patient's bony anatomy in various functional positions.

The data storage 414 may also store one or more landmark models 432, which may be embodied as one or more models or algorithms (e.g., a machine learning algorithm) capable of analyzing the medical images 404 and determining associated anatomical landmarks. As discussed in more detail below, the analysis device 402 may determine the anatomical landmarks in an automated fashion using the landmark models 432 and/or determine the anatomical landmarks in a manual fashion based on annotations of the medical images received from the orthopaedic surgeon.

Additionally, the data storage 414 may store a contact model 434 and/or an impingement model 436. As discussed in more detail below, the contact model 434 is illustratively embodied as a mathematical model (specifically, a regression model) that takes a set of candidate orientations for the acetabular cup 104, patient-specific pelvic tilt measurements, and type and size data for the hip prosthesis 100 as inputs. Using these inputs, the contact model 434 generates a predicted distance between (i) the edge of the cup liner 122 of the acetabular cup 104 and (ii) contact between the cup liner 122 and the femoral head 118 of the femoral prosthesis 102, for both standing and seated positions of the patient, associated with each candidate orientation for the acetabular cup 102 supplied as an input to the contact model 434. The impingement model 436 is illustratively embodied as a mathematical model (specifically, a regression model) that takes a set of candidate orientations for the acetabular cup 104, patient-specific pelvic tilt measurements, type and size data for the hip prosthesis 100, and a version at which the femoral prosthesis 102 is to be oriented as inputs. Using these inputs, the impingement model 436 generates a predicted amount of femoral prosthesis rotation until impingement of the femoral prosthesis 102 and the acetabular cup 104, for both standing and seated positions of the patient, associated with each candidate orientation for the acetabular cup supplied as an input to the impingement model 436. As discussed further below, in the illustrative embodiment, the analysis device 402 uses the contact model 434 and the impingement model 436 together to predict sets of orientations for the acetabular cup 104 that will not result in either edge loading of the acetabular cup 104 by the femoral prosthesis 102 or impingement of the femoral prosthesis 102 and the acetabular cup 104 when the femoral prosthesis 102 is oriented at the various versions.

The display 416 may be embodied as any type of display capable of displaying information to a user (e.g., the orthopaedic surgeon) of analysis device 402. For example, the display 416 may be embodied as a liquid crystal display (LCD), a light emitting diode (LED) display, an organic light emitting diode (OLED), a cathode ray tube (CRT) display, a plasma display, an augmented or virtual reality headset, and/or other display device. In some embodiments, the display 416 may include a touchscreen, which may be configured to receive input from the orthopaedic surgeon based on a tactile interaction. Additionally, in some embodiments, the display 416 or a duplicate display 416 may be separate from the analysis device 402, but communicatively coupled thereto, as shown in FIG. 4 in dashed lines.

The communication subsystem 418 may be embodied as any type of communication circuit, device, or collection thereof, capable of enabling communications between the analysis device 402 and the imaging device 404 and/or other devices of the computer system 400. To do so, the communication subsystem 418 may be configured to use any one or more communication technologies (e.g., wireless or wired communications) and associated protocols (e.g., Ethernet, Bluetooth®, Wi-Fi®, WiMAX, LTE, 5G, etc.) to effect such communication.

The one or more peripheral device(s) 420 may include any number of additional peripheral or interface devices, such as other input/output devices, storage devices, and so forth. The particular devices included in the peripheral device(s) 420 may depend on, for example, the type and/or intended use of the analysis device 402.

The imaging device 404 may be embodied as any type of device or collection of devices capable of pre-operatively and/or intra-operatively generating medical images of the bony anatomy of the patient. In some embodiments, the imaging device 404 is embodied as (or includes) an X-Ray imaging machine capable of generating two-dimensional medical images. In other embodiments, the imaging device 404 may be embodied as (or include) an imaging device capable of generating three-dimensional medical images, such as an MRI or CT machine. In the illustrative embodiment, the imaging device 404 generates images of the patient's hip joint while the hip joint is positioned in several functional positions, including one or more anterior-posterior and/or sagittal (lateral) medical images while the patient is standing, seated, and/or supine. Of course, in other embodiments, the imaging device 404 may be configured to produce additional or different medical images of the patient's bony anatomy. For instance, in some embodiments, the medical images may include the patient's full femur, the patient's full pelvis, and/or some or all of the patient's spine.

The network 406 may be embodied as any type of communication network capable of facilitating communication between the hip prosthesis positioning analysis device 402 and the imaging device 404 (and other components of the computer system 400). As such, the network 406 may include one or more networks, routers, switches, gateways, computers, and/or other intervening devices. For example, the network 406 may be embodied as or otherwise include one or more local or wide area networks, cellular networks, publicly available global networks (e.g., the Internet), an ad hoc network, a short-range communication network or link, or any combination thereof.

In some embodiments, the computer system 400 may also include a surgical tracking system 408. The surgical tracking system 408 may be embodied as any type of surgical tracking system, surgical navigation system, digital surgery system, or the like. For example, the surgical tracking system 408 may be embodied as a computer assisted orthopaedic surgery (CAOS) system in some embodiments. As discussed in more detail below, the surgical tracking system 408 is configured to intra-operatively detect the actual orientation of an acetabular cup 104 (either a trial or final component) relative to the patient's bony anatomy (e.g., relative to the patient's acetabulum 200). For example, the computer system 400 may be configured to optically track markers attached to the patient's acetabulum 200 and the acetabular cup 104 to facilitate this detection. In some embodiments, the tracking provided by the surgical tracking system 408 may replace intra-operative images produced by the imaging device 404, discussed in more detail below.

Figure 5:
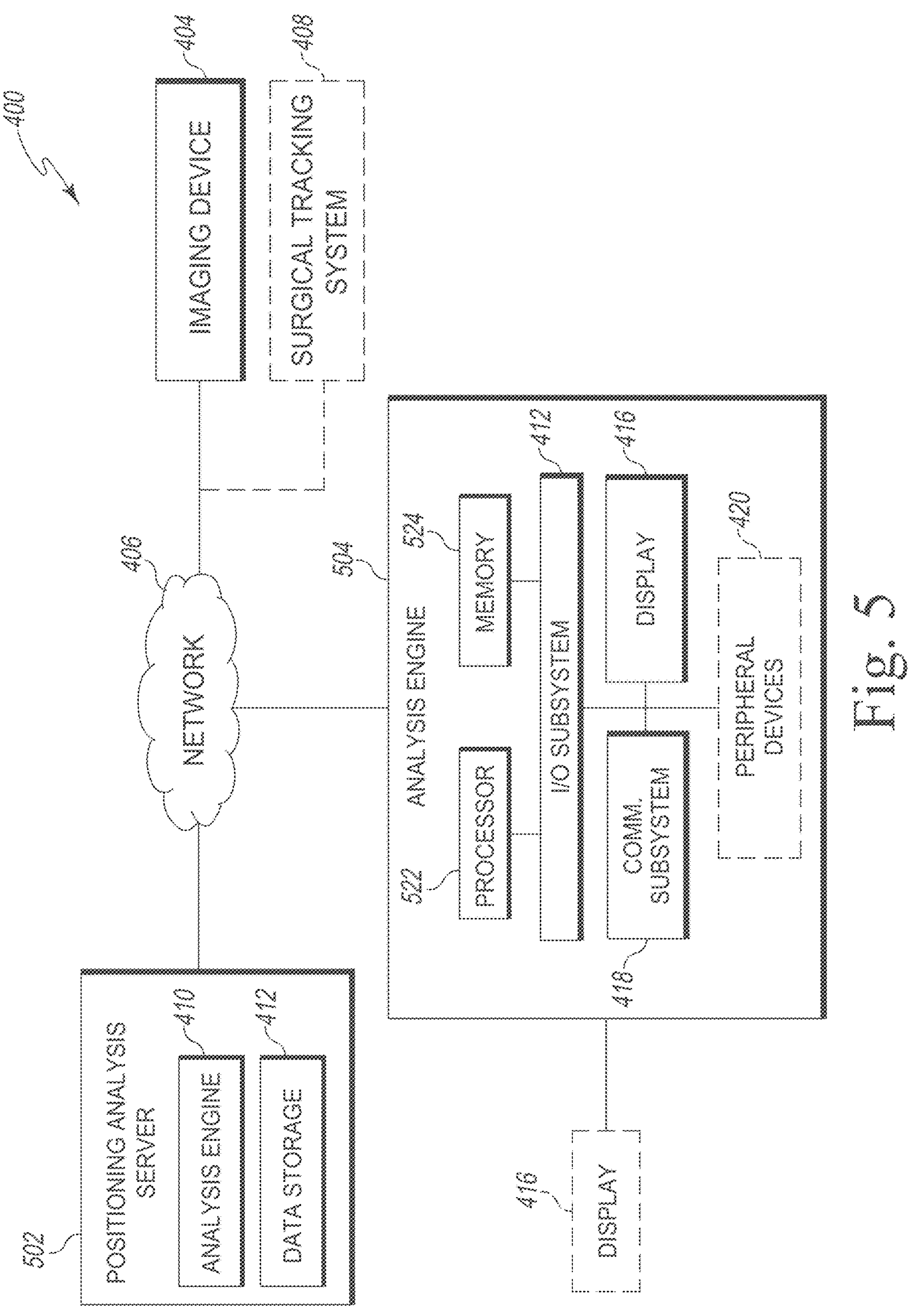
FIG. 5 is a block diagram of another embodiment of a computer system for determining a position of a hip prosthesis (such as the hip prosthesis of FIG. 1) in a bone of a patient.

Referring now to FIG. 5, in some embodiments the computer system 400 may implemented as a cloud-based system. In such embodiments, the computer system 400 may include a positioning analysis server 502, which is communicatively coupled to a local computer device 504 via the network 406. The positioning analysis server 502 may be embodied as any type of computer or computation device capable of performing the functions described herein. For example, the positioning analysis server 502 may be embodied as a server, a rack-mounted computer, a network appliance, a desktop computer, a laptop computer, a tablet computer, or other computer or computer device.

As shown in FIG. 5, each of the analysis engine 410 and the data storage 412 is located on the positioning analysis server 502. As such, the positioning analysis server 502 is configured to perform substantially the same functions as described above and below in regard to the analysis device 402. For example, the positioning analysis server 502 is configured to acquire or otherwise receive medical images of the patient's hip joint from the imaging device 404 and to determine patient-specific pelvic tilt measurements based on those medical images. Additionally, the positioning analysis server 502 is configured to determine or predict sets of target orientations for the acetabular cup 104, including sets of orientations for the acetabular cup 104 that will not result in either edge loading of the acetabular cup 104 by the femoral prosthesis 102 or impingement of the femoral prosthesis 102 and the acetabular cup 104 when the femoral prosthesis 102 is oriented at the various versions. The positioning analysis server 502 may transmit any of this data and/or graphics representing any of this data to the local computer device 504.

The local computer device 504 may be embodied as any type of computer or computation device capable of performing the functions described herein. For example, the local computer device 504 may be embodied as a desktop computer, a laptop computer, a tablet computer, a smartphone, a mobile computer, a smart device, a wearable computer system, or other computer or computer device. Illustratively the local computer device 504 includes a processor 522, a memory 520, the input/output ("I/O") subsystem 412, the display 416, the communication system 418 and, in some embodiments, the one or more peripheral devices 420.

The processor 522 may be similar to the processor 422 of the analysis device 402 described above and may be embodied as any type of processor capable of performing the functions described herein. For example, the processor 522 may be embodied as a single or multi-core processor(s), digital signal processor, microcontroller, or other processor or processing/controlling circuit. Similarly, the memory 524 may be similar to the memory 424 of the analysis device 402 described above and may be embodied as any type of volatile and/or non-volatile memory or data storage capable of performing the functions described herein. In operation, the memory 524 may store various data and software used during operation of the local computer device 504 such as operating systems, applications, executable software, programs, libraries, and drivers.

Figure 6A:
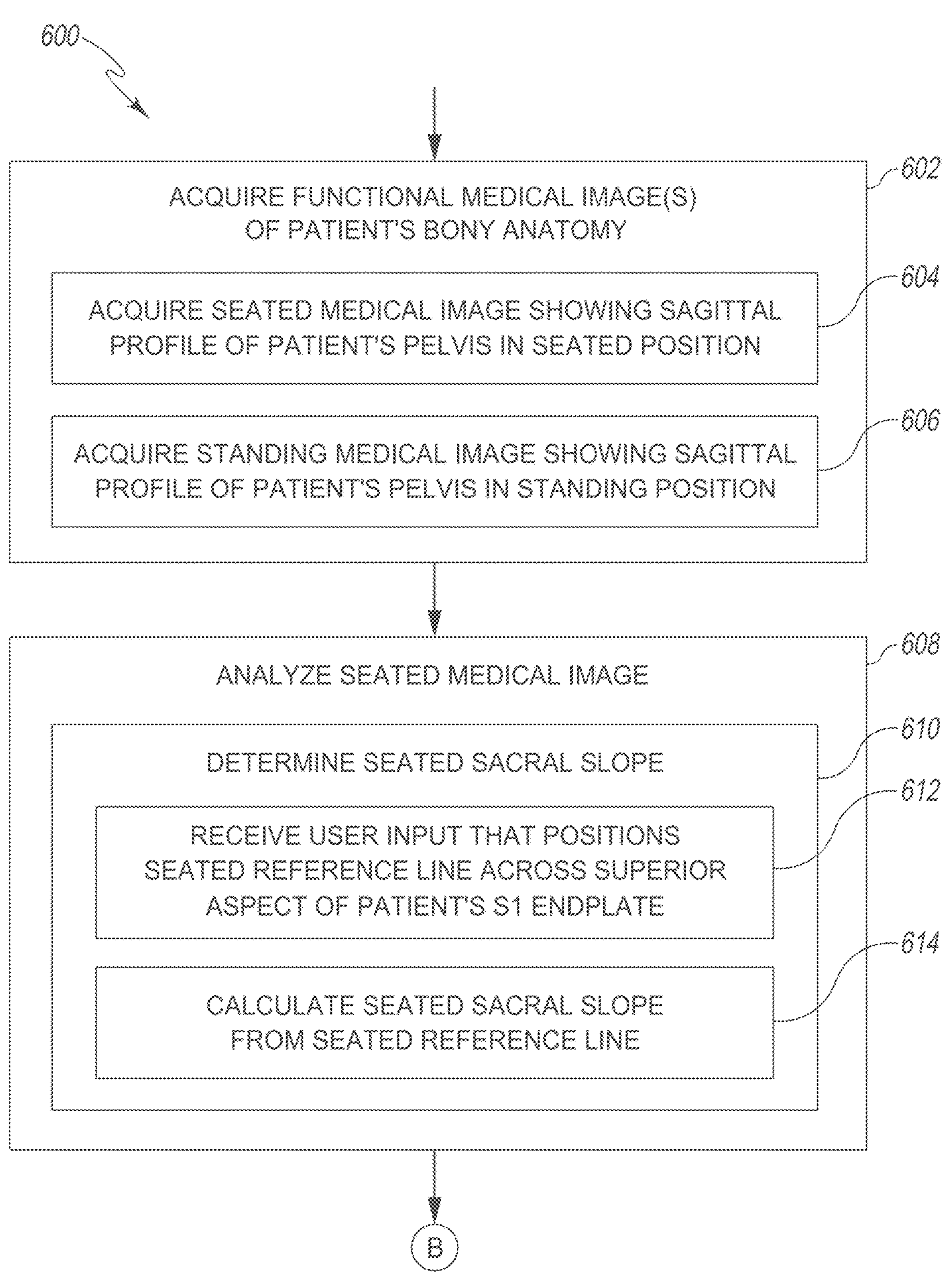
Figure 6C:
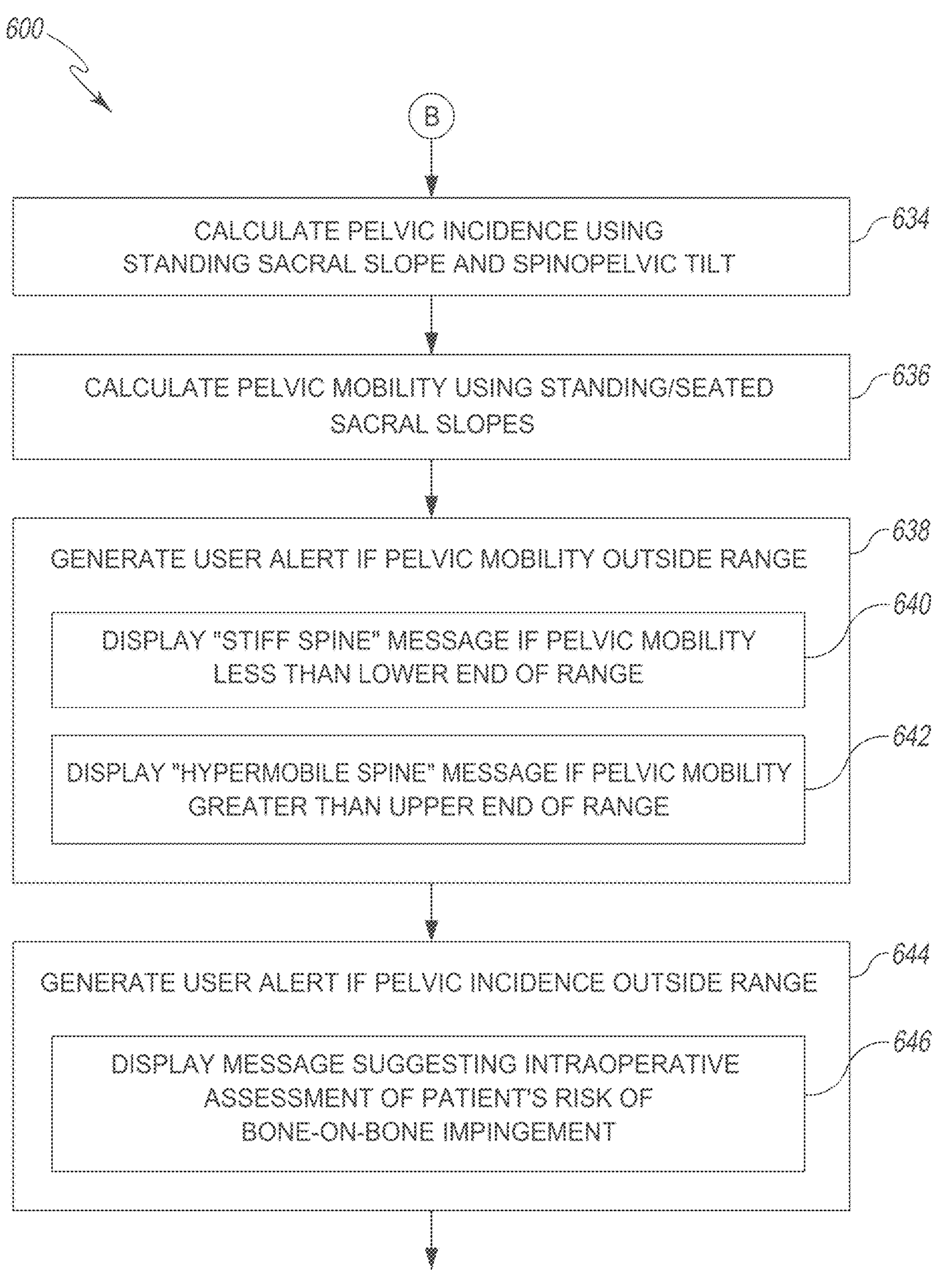

Referring now to FIGS. 6A-6C, in use, the computer system 400 (e.g., the hip prosthesis positioning analysis device 402 of FIG. 4 and/or the positioning analysis server 502 of FIG. 5) is configured to execute a method 600 for determining patient-specific pelvic tilt measurements. The computer system 400 may alert a user (e.g., a surgeon) if the patient-specific pelvic tilt measurements are outside of predetermined ranges. Additionally, these (and other) patient-specific pelvic tilt measurements may be used in determining a position of the hip prosthesis 100, as discussed further below. The method 600, or portions thereof, may be embodied as a set of executable instructions stored on the computer system 400 and executable by the computer system 400. As such, it should be appreciated that the operations of the method 600 may be performed by one or more components of the analysis device 402 and/or devices communicatively coupled to the analysis device 402.

The method 600 begins with block 602 in which the analysis device 402 acquires (e.g., captures, obtains, or receives) a set of medical images of the patient's hip joint on which the orthopaedic surgery is to be performed from the imaging device 404. The medical images are embodied as images of the patient's hip joint with the hip joint positioned in various functional positions. The analysis device 402 may receive any type and number of suitable medical images that facilitate the determination of patient-specific pelvic tilt measurements as discussed in more detail below. For example, in the accompanying drawings, the medical images are illustratively embodied as two-dimensional X-ray images. Additionally or alternatively, other types of two-dimensional medical images and/or three-dimensional medical images may be used. In some embodiments, one or more two-dimensional medical images may be generated from a three-dimensional medical image (e.g., a CT scan) by isolating slices of the three-dimensional medical image (e.g., slices parallel to a sagittal plane and/or to a coronal plane) and/or by projecting structure(s) in the three-dimensional medical image onto a two-dimensional plane (to create a simulated X-ray image).

Figure 7:
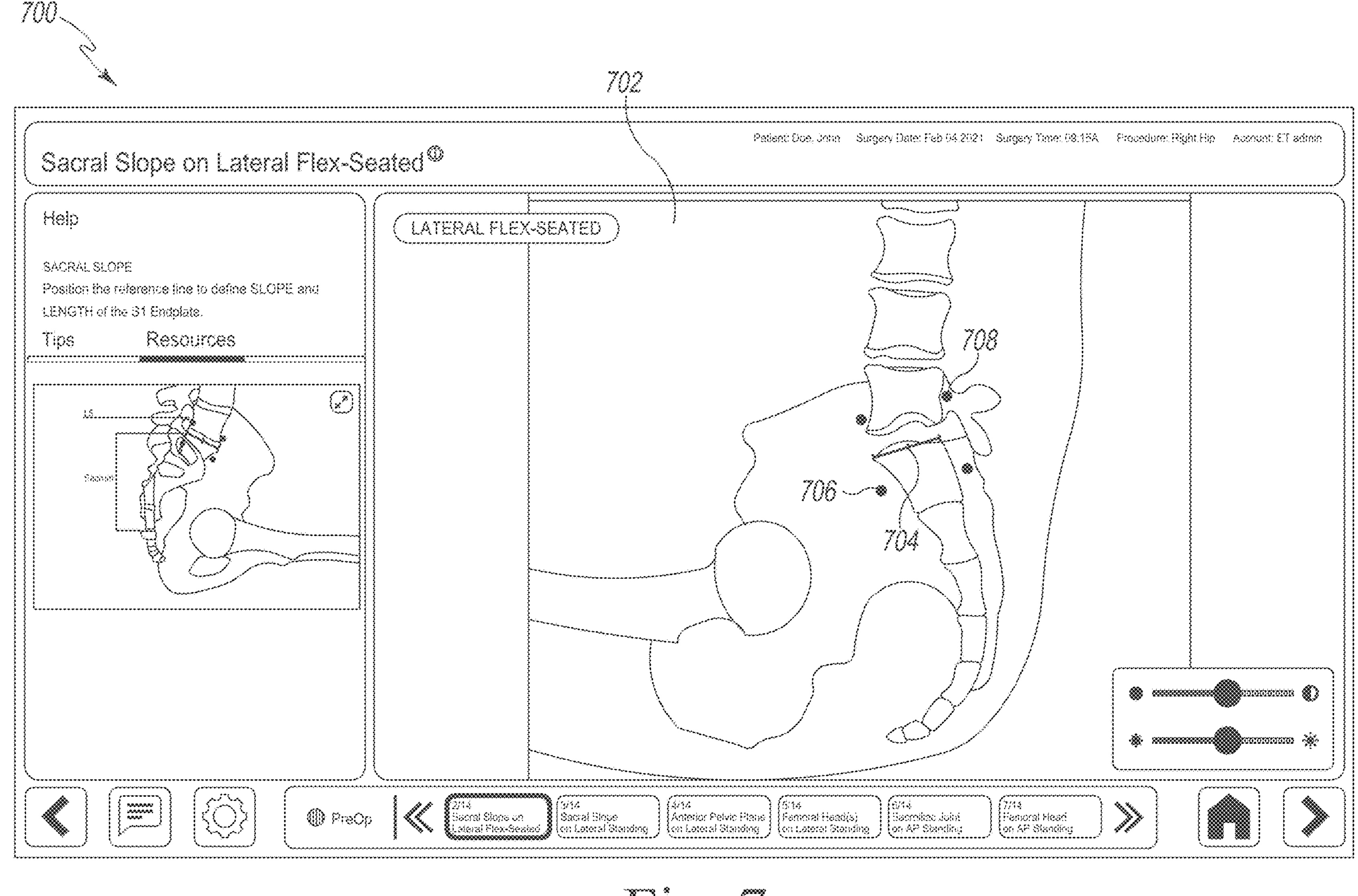
FIG. 7 is an illustrative screen image that may be displayed during the performance of the method of FIGS. 6A-6C showing a seated medical image of the patient's hip joint and a seated reference line positioned by a user.
Figure 8:
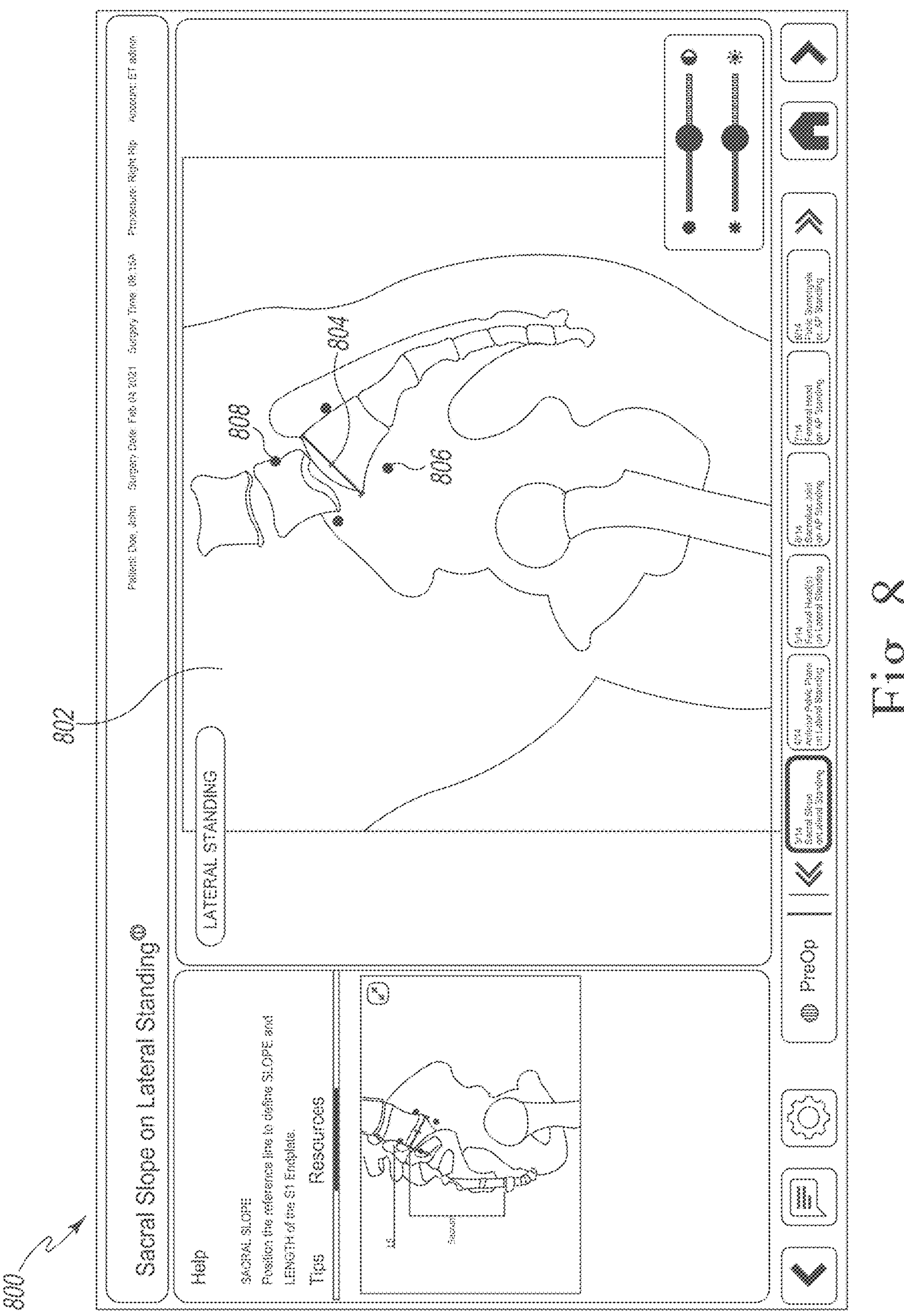
FIG. 8 is an illustrative screen image that may be displayed during the performance of the method of FIGS. 6A-6C showing a standing medical image of the patient's hip joint and a standing reference line positioned by a user.
Figure 9:
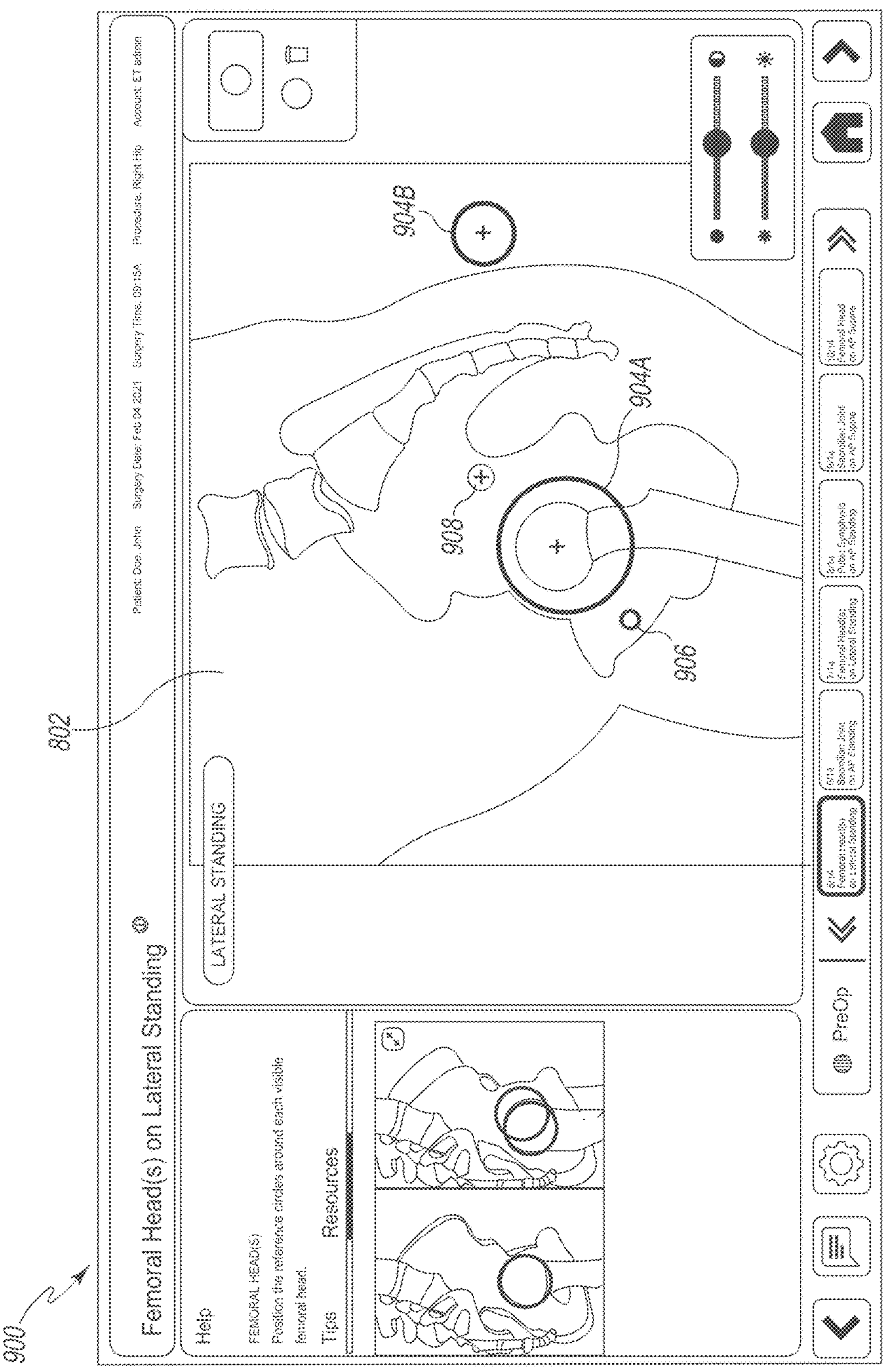
FIG. 9 is an illustrative screen image that may be displayed during the performance of the method of FIGS. 6A-6C showing the standing medical image of the patient's hip joint and a reference circle positioned by a user.

In the illustrative embodiment, the analysis device 402 acquires a seated medical image in block 604 and a standing medical image in block 606. The standing medical image may be embodied as a medical image of the patient's hip joint taken from a sagittal plane of the patient while the patient is standing. As such, the standing medical image shows a sagittal profile of the patient's pelvis in a standing position. One example of a standing medical image 802 is shown in FIGS. 8 and 9. The seated medical image may be embodied as a medical image taken from a sagittal plane of the patient while the patient is in a seated position with the hip joint in full flexion (e.g., with the femur flexed about 90 degrees relative to the standing position). As such, the seated medical image shows a sagittal profile of the patient's pelvis in a seated position. One example of a seated medical image 702 is shown in FIG. 7. In some embodiments of block 602, the analysis device 402 may acquire the standing medical image but not the seated medical image.

Block 602 may also involve acquiring other medical images of the patient's hip joint in the same and/or different functional positions, such as a standing anterior-posterior medical image, a supine anterior-posterior medical image, and a sagittal standing-with-contralateral-flexed-limb medical image. The anterior-posterior medical images may be embodied as medical images of the patient's hip joint taken from a coronal plane anterior to the patient while the patient is standing or supine, respectively. In embodiments using a standing (rather than supine) frame of reference to report target orientations for the acetabular cup 104, the supine anterior-posterior medical image is advantageously not necessary and may be omitted. The sagittal standing-with-contralateral-flexed-limb medical image may be embodied as a medical image taken from a sagittal plane of the patient while the patient is standing with the leg of the opposite hip joint from the hip joint on which the orthopaedic surgery is being performed positioned in flexion (e.g., with the opposite femur flexed about 90 degrees relative to the standing position).

After the analysis device 402 acquires the medical images in block 602 of FIG. 6A, the analysis device 402 analyzes the seated medical image in block 608. To do so, the analysis device 402 may identify one or more anatomical landmarks of the patient's bony anatomy in the seated medical image. In particular, the analysis device 402 identifies one or more anatomical landmarks on the patient's pelvis. In some embodiments, the analysis device 402 may identify the relevant anatomical landmark(s) based on annotation of the seated medical image provided by the surgeon, as further described below. Additionally or alternatively, in other embodiments, the analysis device 402 may be configured to automatically and/or autonomously identify the relevant anatomical landmark(s) in the seated medical image in block 608. For example, in some embodiments of method 600, the analysis device 402 may utilize a machine-learning algorithm (of landmarks model 432) to identify the relevant anatomical landmark(s) in the seated medical image in block 608. In such embodiments, the machine learning algorithm may undergo a training phase in which the machine learning algorithm is supplied with a training set of surgeon-annotated medical images of sample patients. In this way, the machine-learning algorithm is trained to identify the corresponding anatomical landmarks in new medical images such as the medical images of the present patient.

The one or more anatomical landmarks identified in block 608 may be embodied as any anatomical landmark that facilitates or improves the determination of the pelvic tilt measurements of the patient. The particular landmarks used may depend on various factors such as the patient's bony anatomy, the size and type of hip prosthesis 100, and/or other factors. For example, in the illustrative embodiment of block 608, the analysis device 402 determines a seated sacral slope of the patient, as shown in block 610. The seated sacral slope is defined by the superior aspect of patient's S1 endplate (i.e., the most superior aspect of the patient's sacrum, which can be identified as distal to the most distal vertebral body, L5) when the patient is in the seated position shown in the seated medical image. In the illustrative embodiment, the analysis device 402 provides a graphical user interface (GUI) through which a surgeon (or another user working at the surgeon's direction) can annotate the seated medical image to identify the seated sacral slope. One example of this GUI 700, which the computer system 400 may generate on display 416, is shown in FIG. 7.

The GUI 700 includes the seated medical image 702 (or a relevant portion thereof) and instructs the surgeon to position the seated reference line 704 to define the slope and length of the S1 endplate. The entire length of the S1 endplate should be demarcated with the seated reference line 704, with a first end of the seated reference line 704 at the anterior margin and a second end of the seated reference line 704 at the posterior margin. This placement ensures that the midpoint and anterior point of the seated reference line 704 are accurate enough to be used in later calculations. The seated reference line 704 should follow the S1 endplate as closely as possible, but in the event the S1 endplate is curved or osteophytes are present, the surgeon can prioritize selecting accurate endpoints in order to approximate the slope as best as possible. To facilitate positioning of the first end of the seated reference line 704 at the anterior margin of the S1 endplate, the GUI 700 provides two anchors 706 (only one of which is labeled in FIG. 7) that can each be selected and dragged by the user to move the first end. To facilitate positioning of the second end of the seated reference line 704 at the posterior margin of the S1 endplate, the GUI 700 provides two anchors 708 (only one of which is labeled in FIG. 7) that can each be selected and dragged by the user to move the second end. Additionally, the GUI 700 provides slider controls that allow the user to adjust the contrast and brightness of the seated medical image 702 to facilitate accurate positioning of the seated reference line 704.

As the user positions the seated references line 704 across the superior aspect of the patient's S1 endplate shown in the seated medical image 702, via the GUI 700, the analysis device 402 receives these user inputs in block 612. Once the seated reference line 704 has been positioned, the method 600 proceeds to block 614, in which the analysis device 402 calculates the seated sacral slope using the seated reference line 704. In the illustrative embodiment of block 614, the analysis device 402 calculates a seated sacral slope value as an angle (relative to the horizontal of the seated medical image 702), expressed in degrees, using the formula:

$$\text{Seated Sacral Slope} = \tan^{-1}\left(\frac{y_2 - y_1}{x_2 - x_1}\right),$$

where the end of the seated reference line 704 furthest to the left in the image (i.e., having the least x value) is assigned coordinate points ($x_1$, $y_1$) and the end of the seated reference line 704 furthest to the right in the image (i.e., having the greatest x value) is assigned coordinate points ($x_2$, $y_2$).

After analyzing the seated medical image in block 608, the illustrative embodiment of method 600 proceeds to block 616, in which the analysis device 402 analyzes the standing medical image. (In other embodiments of method 600, block 616 may be performed before or simultaneously with block 608.) In block 616, the analysis device 402 may identify one or more anatomical landmarks of the patient's bony anatomy in the standing medical image. In particular, the analysis device 402 identifies one or more anatomical landmarks on the patient's pelvis. In some embodiments, the analysis device 402 may identify the relevant anatomical landmark(s) based on annotation of the standing medical image provided by the surgeon, as further described below. Additionally or alternatively, in other embodiments, the analysis device 402 may be configured to automatically and/or autonomously identify the relevant anatomical landmark(s) in the standing medical image in block 616. For example, in some embodiments of method 600, the analysis device 402 may utilize a machine-learning algorithm (of landmarks model 432) to identify the relevant anatomical landmark(s) in the standing medical image in block 616.

The one or more anatomical landmarks identified in block 616 may be embodied as any anatomical landmark that facilitates or improves the determination of the pelvic tilt measurements of the patient. The particular landmarks used may depend on various factors such as the patient's bony anatomy, the size and type of hip prosthesis 100, and/or other factors. For example, in the illustrative embodiment of block 616, the analysis device 402 determines a standing sacral slope of the patient, as shown in block 618, and a femoral head center, as shown in block 626. The standing sacral slope is defined by the superior aspect of patient's S1 endplate (i.e., the most superior aspect of the patient's sacrum, which can be identified as distal to the most distal vertebral body, L5) when the patient is in the standing position shown in the standing medical image. In the illustrative embodiment, the analysis device 402 provides another GUI through which a surgeon (or another user working at the surgeon's direction) can annotate the standing medical image to identify the standing sacral slope. One example of this GUI 800, which the computer system 400 may generate on display 416, is shown in FIG. 8.

The GUI 800 includes the standing medical image 802 (or a relevant portion thereof) and instructs the surgeon to position the standing reference line 804 to define the slope and length of the S1 endplate. The entire length of the S1 endplate should be demarcated with the standing reference line 804, with a first end of the standing reference line 804 at the anterior margin and a second end of the standing reference line 804 at the posterior margin. This placement ensures that the midpoint and anterior point of the standing reference line 804 are accurate enough to be used in later calculations. The standing reference line 804 should follow the S1 endplate as closely as possible, but in the event the S1 endplate is curved or osteophytes are present, the surgeon can prioritize selecting accurate endpoints in order to approximate the slope as best as possible. To facilitate positioning of the first end of the standing reference line 804 at the anterior margin of the S1 endplate, the GUI 800 provides two anchors 806 (only one of which is labeled in FIG. 8) that can each be selected and dragged by the user to move the first end. To facilitate positioning of the second end of the standing reference line 804 at the posterior margin of the S1 endplate, the GUI 800 provides two anchors 808 (only one of which is labeled in FIG. 8) that can each be selected and dragged by the user to move the second end. Additionally, the GUI 800 provides slider controls that allow the user to adjust the contrast and brightness of the standing medical image 802 to facilitate accurate positioning of the standing reference line 804.

As the user positions the standing reference line 804 across the superior aspect of the patient's S1 endplate shown in the standing medical image 802, via the GUI 800, the analysis device 402 receives these user inputs in block 620. Once the standing reference line 804 has been positioned, the method 600 proceeds to block 622, in which the analysis device 402 calculates the standing sacral slope using the standing reference line 804. In the illustrative embodiment of block 622, the analysis device 402 calculates a standing sacral slope value as an angle (relative to the horizontal of the standing medical image 802), expressed in degrees, using the formula:

$$\text{Standing Sacral Slope} = \tan^{-1}\left(\frac{y_2 - y_1}{x_2 - x_1}\right),$$

where the end of the standing reference line 804 furthest to the left in the image (i.e., having the least x value) is assigned coordinate points ($x_1$, $y_1$) and the end of the standing reference line 804 furthest to the right in the image (i.e., having the greatest x value) is assigned coordinate points ($x_2$, $y_2$). Block 618 also involves block 624, in which the analysis device 402 calculates a sacral slope midpoint as the midpoint of the standing reference line 804 positioned by the user. In the illustrative embodiment of block 624, the analysis device 402 calculates the midpoint of the standing reference line 804 as a Cartesian coordinate using the formula:

$$\text{Sacral Slope Midpoint}_{standing} = \left(\frac{x_1 + x_2}{2}, \frac{y_1 + y_2}{2}\right).$$

As noted above, the illustrative embodiment of block 616 also involves block 626, in which the analysis device 402 determines a femoral head center from the standing medical image. The femoral head center is defined as the point halfway between the respective centers of rotation of the patient's femurs (when the patient is in the standing position shown in the standing medical image). In the illustrative embodiment, the analysis device 402 provides another GUI through which a surgeon (or another user working at the surgeon's direction) can annotate the standing medical image to identify the femoral head center. One example of this GUI 900, which the computer system 400 may generate on display 416, is shown in FIG. 9.

The GUI 900 includes the standing medical image 802 (or a relevant portion thereof) and instructs the surgeon to position the reference circles 904A, 904B around each visible femoral head. In some cases, only one femoral head will be visible in the standing medical image 802. In such cases, the surgeon can position the reference circle 904A around the visible femoral head and delete the other reference circle 904B. To facilitate positioning around the femoral head(s), the GUI 900 provides two anchors 906, 908, as shown in FIG. 9. The anchor 906 can be selected and dragged by the user to manipulate the position of the associated reference circle 904. The anchor 908 can be selected and dragged by the user to change the size of the associated reference circle 904 while maintaining the current center point. Additionally, the GUI 900 provides slider controls that allow the user to adjust the contrast and brightness of the standing medical image 802 to facilitate accurate positioning of the reference circles 904.

As the user positions the reference circle 904A, and possibly the reference circle 904B, around the visible femoral head(s) in the standing medical image 802, via the GUI 900, the analysis device 402 receives these user inputs in block 628. Once the reference circle(s) 904 has/have been positioned, the method 600 proceeds to block 630, in which the analysis device 402 records the femoral head center using the center(s) of the reference circle(s) 904. Where the user only placed a single reference circle 904A, the analysis device 402 records the center of the reference circle 904A as the femoral head center in block 630. Alternatively, where the user placed both reference circles 904A, 904B, the analysis device 402 calculates a femoral head midpoint as a Cartesian coordinate using the formula:

$$\text{Femoral Head Midpoint} = \left(\frac{x_{FHC1} + x_{FHC2}}{2}, \frac{y_{FHC1} + y_{FHC2}}{2}\right),$$

where the center of the reference circle 904A is assigned coordinate points ($x_{FHC1}$, $y_{FHC1}$) and the center of the reference circle 904B is assigned coordinate points ($x_{FHC2}$, $y_{FHC2}$), and then records this midpoint as the femoral head center.

In some embodiments of method 600, block 616 may further involve determining an anterior pelvic plane from the standing medical image 802. For instance, the analysis device 402 may present another GUI that allows the surgeon to annotate with standing medical image 802 with reference point markers on the patient's pubic symphysis and two anterior iliac spine (ASIS) points. The surgeon may place these three reference point markers in any order. (Additionally or alternatively, in some embodiments, these three reference point markers may be placed automatically by the analysis device 402 using image analysis and machine learning.) Once the three reference point markers are placed, the analysis device 402 identifies the lowest marker as the pubic symphysis and the remaining two markers as ASIS points and calculates the slope of the patient's anterior pelvic plane in the standing position from the three reference point markers. The analysis device 402 also determines whether the patient's pelvis is left-facing or right-facing in the standing medical image 802 by comparing relative positions of sacral slope midpoint and a midpoint between the two ASIS markers. The illustrative embodiment of method 600 assumes that the patient's pelvis is a rigid body, such that the patient's anterior pelvic plane in the seated position as compared to the standing position has an equivalent relationship to the patient's sacral slope in the seated position as compared to the standing position. As such, the illustrative embodiment of method 600 does not require the surgeon to annotate the anterior pelvic plane (or other anatomical features beyond the sacral slope) on the seated medical image 702.

After analyzing the standing medical image in block 616, the method 600 proceeds to block 632, in which the analysis device 402 calculates a spinopelvic tilt for the patient's pelvis in the standing position shown in the standing medical image. To do so, in block 632, the analysis device 402 defines a line between the sacral slope midpoint (from block 624) and the femoral head center (from block 630). The angle of this derived line, measured to a vertical line, is the spinopelvic tilt associated with the patient's standing position. In the illustrative embodiment of block 632, the analysis device 402 calculates a spinopelvic tilt value as an angle (relative to the vertical of the standing medical image 802), expressed in degrees, using the formula:

$$\text{Spinopelvic Tilt}_{standing} = \tan^{-1}\left(\frac{x_{SStm} - x_{FHC}}{y_{SStm} - y_{FHC}}\right)$$

where ($x_{SStm}$, $y_{SStm}$) is the coordinate point for the sacral slope midpoint (from block 624) and ($x_{FHC}$, $y_{FHC}$) is the coordinate point for the femoral head center (from block 630). When the sacral slope midpoint is posterior to the femoral head center, it is a positive spinopelvic tilt value and, when the sacral slope midpoint is anterior to the femoral head center, it is a negative spinopelvic tilt value. Therefore, for a left-facing pelvis in the standing medical image, the spinopelvic tilt value is multiplied by −1. For a right-facing pelvis in the standing medical image, the native sign is kept.

After calculating the spinopelvic tilt value for the standing medical image in block 632, the method 600 proceeds to block 634, in which the analysis device 402 calculates a pelvic incidence specific to the patient. This pelvic incidence is defined as an angle between the derived line from block 632 (extending between the sacral slope midpoint and the femoral head center) and a conceptual line perpendicular to the standing sacral slope at the sacral slope midpoint. In the illustrative embodiment of block 634, the analysis device 402 calculates a pelvic incidence value by summing the standing sacral slope value (from block 622) and the spinopelvic tilt value (from block 632). In the illustrative embodiment, each of the pelvic incidence value, the standing sacral slope value, and the spinopelvic tilt value is an angle expressed in degrees. Because the signs of the standing sacral slope value and the spinopelvic tilt value have already been corrected to match the coordinate system, the sign of the pelvic incidence value will be correct.

In the illustrative embodiment, after calculating the pelvic incidence in block 634, the method 600 proceeds to block 636, in which the analysis device 402 calculates a pelvic mobility specific to the patient. In other embodiments of the method 600, block 636 may be performed at any time after the seated sacral slope is calculated (block 614) and after the standing sacral slope is calculated (block 622). This pelvic mobility is defined as an angle between the seated and standing sacral slopes. In the illustrative embodiment of block 636, the analysis device 402 calculates a pelvic mobility value by subtracting the standing sacral slope value (from block 622) from the seated sacral slope value (from block 614). In the illustrative embodiment, each of the pelvic mobility value, the standing sacral slope value, and the seated sacral slope value is an angle expressed in degrees. While the illustrative embodiment utilizes seated and standing sacral slopes to calculate pelvic mobility, it is contemplated that other pelvic features that are identifiable in both seated and standing medical images could be used to perform a similar calculation. For instance, in some sets of seated and standing medical images, an anterior pelvic plane could be identified in each position, and the two anterior pelvic planes could be used to determine a pelvic mobility specific to the patient.

After calculating the pelvic mobility in block 636, the method 600 proceeds to block 638, in which the analysis device 402 generates a user alert if the patient's pelvic mobility is outside of a predetermined range. In the illustrative embodiment, the analysis device 402 compares the pelvic mobility value calculated in block 636 (here, an angle expressed in degrees) to the range of 10-35 degrees, inclusive. It will be appreciated that, in other embodiments, the range may have a different value for its lower end and/or a different value for its upper end. If the calculated pelvic mobility value is within the range, the analysis device 402 may inform the user that the patient's pelvic mobility is within a normal range. However, in response to the pelvic mobility value being outside the range, the analysis device 402 will generate a user alert. The user alert may take any number of forms including a visual and/or audio alert generated on any part(s) of the computer system 400. In some embodiments, the user alert may be embodied as an icon that appears, changes, or is highlighted on a graphical user interface.

In the illustrative embodiment of block 638, the analysis device 402 generates a different user alert depending on whether the patient's pelvic mobility is above or below the predetermined range. If the calculated pelvic mobility value is less than a lower end of the predetermined range (e.g., less than 10 degrees), the analysis device 402 performs block 640, in which the computer system 400 displays a message that indicates the patient has a stiff spine. In the illustrative embodiment of block 640, the computer system 400 displays the message "Patient has a STIFF SPINE. The algorithm accounts for this in the Target Zone. Special consideration could be taken on implant selection if it is not possible to orient the implant in the Patient Target Zone (e.g., dual-mobility, lipped liners, etc.)" on a GUI. In other embodiments, a different message (or another type of alert, e.g., an icon) relating to the patient having a stiff spine may be displayed in block 640.

On the other hand, if the calculated pelvic mobility value is greater than an upper end of the predetermined range (e.g., greater than 35 degrees), the analysis device 402 performs block 642, in which the computer system 400 displays a message that indicates the patient has a hypermobile spine. In the illustrative embodiment of block 642, the computer system 400 displays the message "Patient has a HYPERMOBILE SPINE. The algorithm accounts for this in the Target Zone. Special consideration could be taken on implant selection if it is not possible to orient the implant in the Patient Target Zone (e.g., dual-mobility, lipped liners, etc.)" on a GUI. In other embodiments, a different message (or another type of alert, e.g., an icon) relating to the patient having a hypermobile spine may be displayed in block 642. In some embodiments of the method 600, the surgeon may select a new hip prosthesis 100, having a different type and/or size than the originally selected hip prosthesis 100, in response to receiving the user alert in block 638.

After block 638 (or at any other time after calculating the pelvic incidence in block 634), the method 600 may proceed to block 644, in which the analysis device 402 generates a user alert if the patient's pelvic incidence is outside of a predetermined range. In the illustrative embodiment, the analysis device 402 compares the pelvic incidence value calculated in block 634 (here, an angle expressed in degrees) to the range of 45-65 degrees, inclusive. It will be appreciated that, in other embodiments, this range may have a different value for its lower end and/or a different value for its upper end. If the calculated pelvic incidence value is within the range, the analysis device 402 may inform the user that the patient's pelvic incidence is within a normal range.

However, in response to the pelvic incidence value being outside the range, the analysis device 402 will generate a user alert. The user alert may take any number of forms including a visual and/or audio alert generated on any part(s) of the computer system 400. In some embodiments, block 644 may involve block 646, in which the computer system 400 displays a message that suggests a surgeon intra-operatively assess the patient's risk of bone-on-bone impingement. In the illustrative embodiment of block 646, the computer system 400 displays the message "Patient has a [HIGH/LOW] PELVIC INCIDENCE. Literature suggests that the patient may be at increased risk for bone-on-bone impingement which should be assessed intra-operatively." This message may be displayed on the computer system 400 pre-operatively and/or intra-operatively, including during the orthopaedic surgical procedure, as a reminder to the surgeon. In other embodiments, this user alert may be embodied as an icon that appears, changes, or is highlighted on a graphical user interface. In some embodiments of the method 600, the surgeon may perform an intra-operative assessment of the patient's risk of bone-on-bone impingement in response to receiving the user alert in block 644.

Figure 10A:
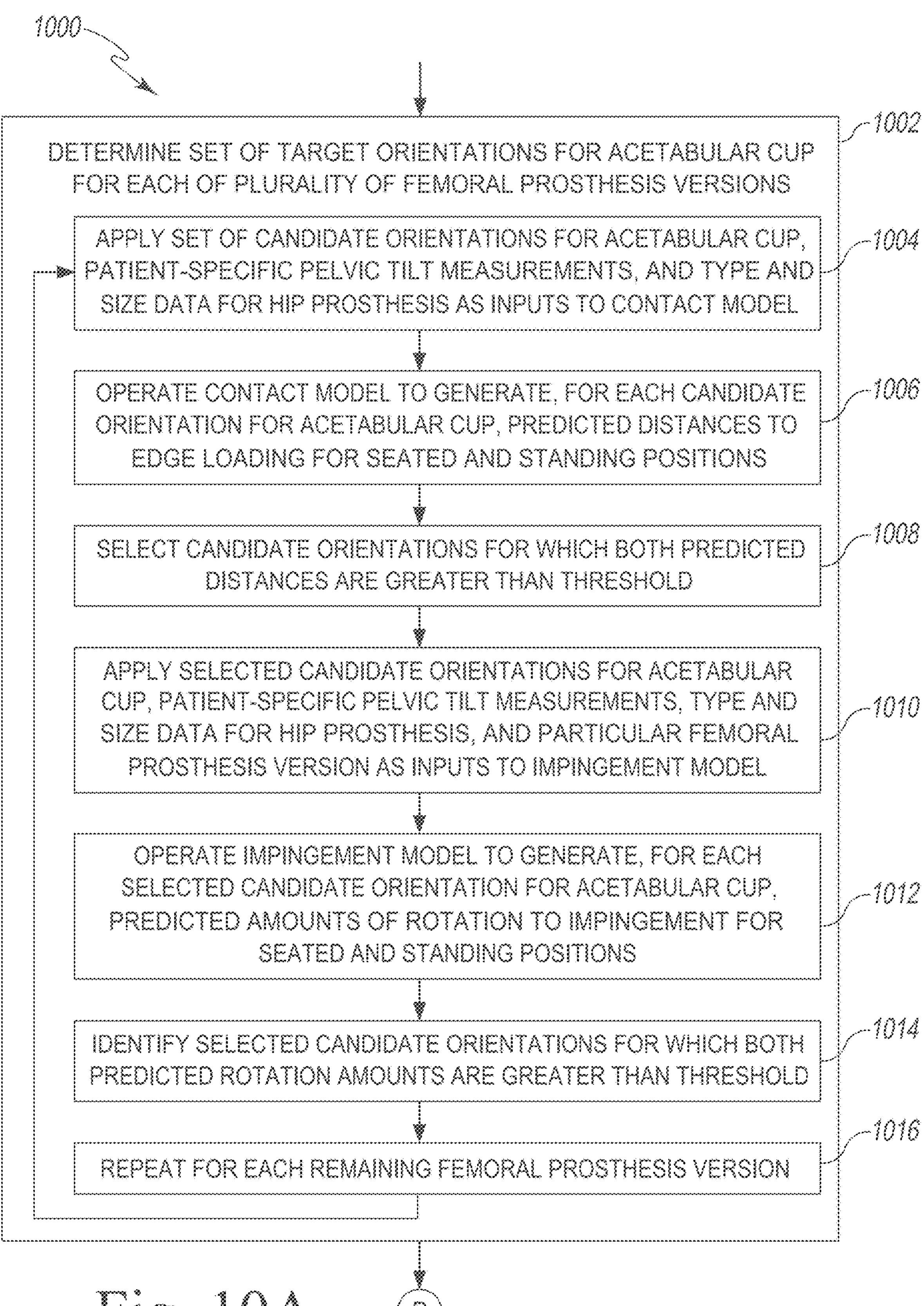
FIGS. 10A-10B are a flow chart diagram of a method for determining and presenting multiple sets of target orientations for the acetabular cup corresponding to the femoral prosthesis being oriented at different versions, which may be executed by the computer system of FIG. 4 or the computer system of FIG. 5.
Figure 10B:
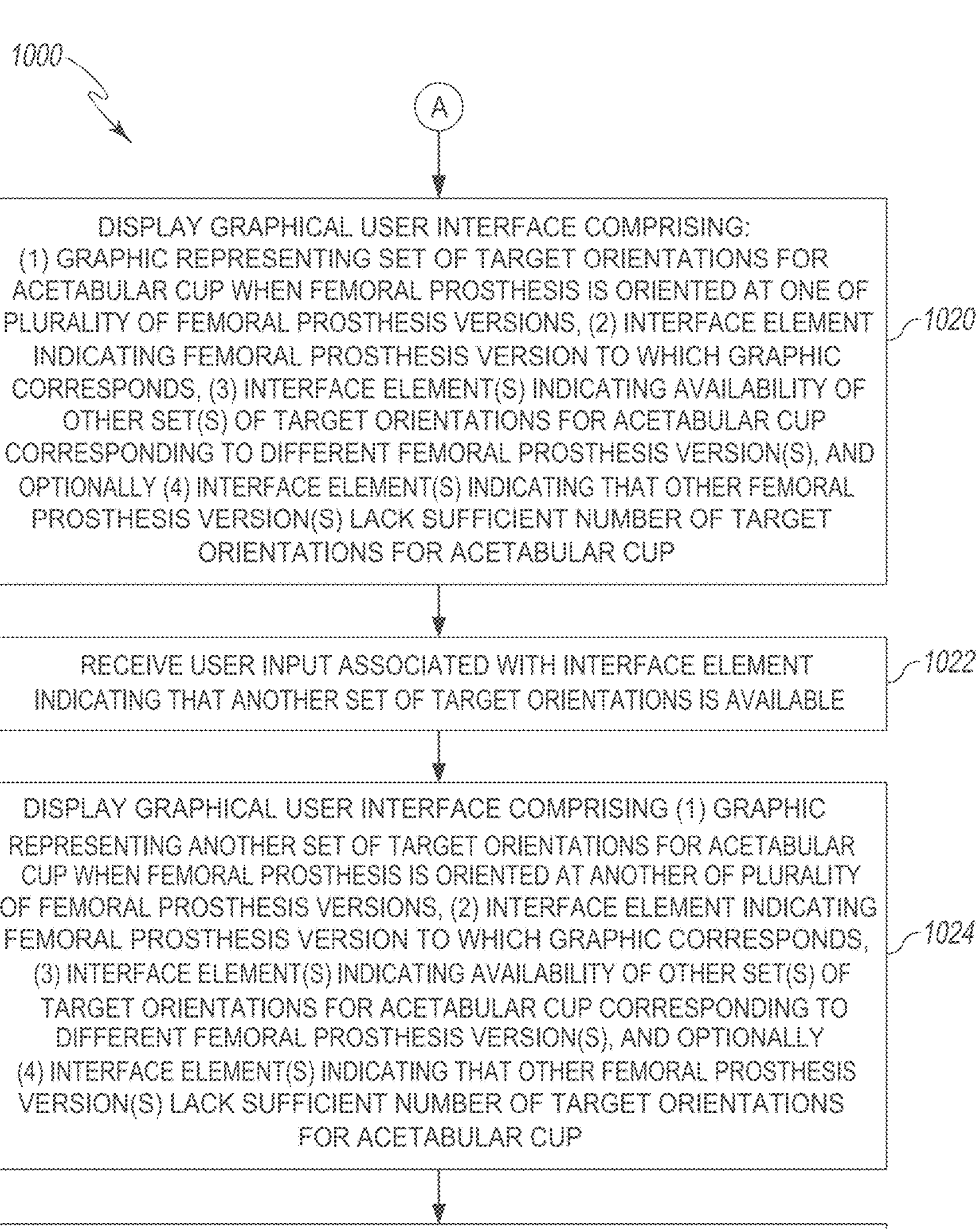

Referring now to FIGS. 10A-10B, in use, the computer system 400 (e.g., the hip prosthesis positioning analysis device 402 of FIG. 4 and/or the positioning analysis server 502 of FIG. 5) is also configured to execute a method 1000 for determining and presenting multiple sets of target orientations for the acetabular cup 104 corresponding to the femoral prosthesis 102 being oriented at different versions. The method 1000, or portions thereof, may be embodied as a set of executable instructions stored on the computer system 400 and executable by the computer system 400. As such, it should be appreciated that the operations of the method 1000 may be performed by one or more components of the analysis device 402 and/or devices communicatively coupled to the analysis device 402.

The patient-specific pelvic tilt measurements determined by the method 600 and other parameters related to the patient's anatomy, to the planned orthopaedic surgical procedure, and to the hip prosthesis 100 feed into the method 1000. For instance, in additional to the patient-specific pelvic tilt measurements discussed above, the analysis device 402 may ask the surgeon to annotate various anatomical landmarks on anterior-posterior (A-P) medical images, taken with the patient in standing and/or supine positions. These annotations may be used to generate inputs to the method 1000 and/or to facilitate presentation of the results of the method 1000 in standing and/or supine frames of reference. As noted above, in embodiments using the standing frame of reference, the methods 600, 1000 may advantageously not require any supine medical images to be obtained or annotated.

The analysis device 402 also asks the surgeon to input the type and size of the hip prosthesis 100 (including the femoral prosthesis 102 and the acetabular cup 104) to be used during the orthopaedic surgical procedure. The surgeon may select the type and size from a menu of available types and sizes or otherwise provide those selections to the analysis device 402. Selection of the type and size of the hip prosthesis 100 provides the method 1000 with data, including geometric measurements, of the hip prosthesis 100. These geometric measurements may illustratively include an inner diameter measurement of the acetabular cup 104 (i.e., of the cup liner 122), an outer diameter measurement of the acetabular cup 104, a proximal-distal distance measurement from the medial edge of the cup liner 122 of the acetabular cup 104 to the center of rotation of the femoral head 118 of the femoral prosthesis 102, a proximal-distal distance measurement from the lateral edge of the cup liner 122 of the acetabular cup 104 to the center of rotation of the femoral head 118 of the femoral prosthesis 102, and the neck angle of the femoral stem 110 of the femoral prosthesis 102 (e.g., relative to the longitudinal angle of the stem 110). In some embodiments, the analysis device 402 may retrieve those geometric measurements from a database based on the type and size of the hip prostheses 100 selected by the surgeon. Alternatively, in other embodiments, the orthopaedic surgeon or other user may manually enter the geometric measurements. In still other embodiments, the geometric measurements may be determined based on three-dimensional models or engineering drawings of the selected hip prosthesis 100 (i.e., of the femoral prosthesis 102 and the acetabular cup 104), including metadata files associated with such model or drawings.

The method 1000 begins with block 1002 in which the analysis device 402 determines a set of target orientations for the acetabular cup 104 (each target orientation being a pair of anteversion and inclination values) for each of a plurality of femoral prosthesis versions. Femoral prosthesis version, also sometimes called femoral neck anteversion (FNA) or femoral version, is an angle between the projection of two lines in the axial plane perpendicular to the femoral shaft: one line going through the proximal femoral neck region and the second one through the distal condylar region, indicating the degree of "twist" of the femur. Femoral prosthesis version affects the biomechanics of the hip, as moment arms and the line of action of muscles around the joint are altered. When performing a total hip arthroplasty, the surgeon may choose between a number of different versions in which to orient the femoral prosthesis 102.

In the illustrative embodiment, block 1002 involves determining a set of target orientations for the acetabular cup 104 for each of five possible versions of the femoral prosthesis 102, specifically −5 degrees, 5 degrees, 15 degrees, 25 degrees, and 35 degrees. These version values were chosen to represent a mean femoral prosthesis version) (15°, #approximately 1 standard deviation from that mean (5°, 25°), and ± approximately 2 standard deviations from that mean (−5°, 35°), based on current medical literature. It is contemplated that other embodiments can use different solution spaces for femoral prosthesis version, including different version values and/or a different number of options for femoral prosthesis version. For instance, in some embodiments, the analysis device 402 may utilize the pre-operative version of the patient's natural femur as the initial femoral prosthesis version when determining the first set of target orientations for the acetabular cup 104. The analysis device 402 can then determine additional sets of target orientations for the acetabular cup 104 using additional femoral prosthesis versions above and below this initial femoral prosthesis version. In such embodiments, the method 1000 may involve measuring the pre-operative version of the patient's natural femur from one or more medical images obtained by the analysis device 402 (e.g., from a CT scan).

Block 1002 may use any suitable algorithm to determine a set of target orientations for the acetabular cup 104 for each femoral prosthesis version in the solution space. For instance, any of the methods described in U.S. Patent Application Publication Nos. 2022/0202494 and 2022/0202503, both published on Jun. 30, 2022, and in PCT International Publication No. WO 2022/144448, published on Jul. 7, 2022 (the entire disclosures of which are incorporated herein by reference) may be used to determine sets of target orientations for the acetabular cup 104 in block 1002. As described in the foregoing references, some embodiments of block 1002 may determine each set of target orientations for the acetabular cup 104 by predicting a set of orientations for the acetabular cup 104 that will not result in either edge loading of the acetabular cup 104 by the femoral prosthesis 102 or impingement of the femoral prosthesis 102 and the acetabular cup 104 when the femoral prosthesis is oriented at the corresponding version. One illustrative embodiment of such an algorithm is described below with reference to blocks 1004-1016 of FIG. 10A.

In the illustrative embodiment, block 1002 begins with block 1004, in which the contact model 434 is supplied with the following inputs: a set of candidate orientations for the acetabular cup 104 (e.g., each pair of integer values for inclination between 20-60 degrees and anteversion between 0-50 degrees, giving 2,091 candidate orientations), patient-specific pelvic tilt measurements (e.g., the pelvic incidence and pelvic mobility values discussed above), and type and size data for the hip prosthesis 100 (e.g., geometric data regarding dimensions of the femoral prosthesis 102 and acetabular cup 104). The contact model 434 is illustratively embodied as a regression model that predicts how close the loading of the acetabular cup liner 122 of the acetabular cup 104 by the femoral head 118 of the femoral prosthesis 102 will be to the edge of the bearing surface of the acetabular cup liner 122 in different functional positions of the patient for each set of input conditions.

After block 1004, the illustrative embodiment of block 1002 proceeds to block 1006, in which the analysis device 402 operates the contact model 434 to generate, for each candidate orientation for the acetabular cup 104, two predicted distances: (i) a closest distance between the edge of the cup liner 122 of the acetabular cup 104 and predicted contact between the cup liner 122 and the femoral head 118 of the femoral prosthesis 102 when the patient is in a standing position and (ii) a closest distance between the edge of the cup liner 122 of the acetabular cup 104 and predicted contact between the cup liner 122 and the femoral head 118 of the femoral prosthesis 102 when the patient is in seated position (e.g., seated-with-fully-flexed-hip, as discussed above). Because the contact model 434 has been specifically configured to generate this data based on the inputs provided, block 1006 can be performed locally in real-time by the analysis device 402 without computationally intensive modeling of the joint and hip prosthesis 100.

After block 1006, the illustrative embodiment of block 1002 proceeds to block 1008, in which the analysis device 402 compares the predicted distances generated by the contact model 434 for each candidate orientation for the acetabular cup 104 to one or more thresholds. For instance, in block 1008, each predicted distance may be compared to a threshold between 0-2 millimeters. If both predicted distances associated with a particular candidate orientation for the acetabular cup 104 are greater than the threshold, that candidate orientation is identified as not resulting edge loading and is selected for further processing by the algorithm. If either predicted distance associated with a particular candidate orientation is less than the threshold, that candidate orientation is not further considered and cannot become part of the set of target orientations for the acetabular cup 104 in this pass of the algorithm. It is contemplated that some embodiments may use multiple thresholds, including thresholds that vary based on the size and/or type of the hip prosthesis 100, in block 1008.

After block 1008, the illustrative embodiment of block 1002 proceeds to block 1010, in which the impingement model 436 is supplied with the following inputs: the selected candidate orientations for the acetabular cup 104 (i.e., those that satisfied the threshold(s) applied in block 1008), the same patient-specific pelvic tilt measurements and the same type and size data for the hip prosthesis 100 that were supplied to the contact model 434 in block 1004, and the femoral prosthesis version for which the set of target orientations for the acetabular cup 104 is being determined (e.g., a planned version for the femoral prosthesis). The impingement model 436 is illustratively embodied as a regression model that predicts how far the femoral prosthesis 106 can rotate before impingement with the acetabular cup 104 in different functional positions of the patient for each set of input conditions.

After block 1010, the illustrative embodiment of block 1002 proceeds to block 1012, in which the analysis device 402 operates the impingement model 436 to generate, for each selected candidate orientation for the acetabular cup 104, two predicted values: (i) an amount by which the femoral prosthesis 106 can externally rotate before impingement with the acetabular cup 104 when the patient is in a standing position and (ii) an amount by which the femoral prosthesis 106 can internally rotate before impingement with the acetabular cup 104 when the patient is in a seated position (e.g., seated-with-fully-flexed-hip, as discussed above). Because the impingement model 436 has been specifically configured to generate this data based on the inputs provided, block 1012 can be performed locally in real-time by the analysis device 402 without computationally intensive modeling of the joint and hip prosthesis 100.

After block 1012, the illustrative embodiment of block 1002 proceeds to block 1014, in which the analysis device 402 compares the predicted amounts of rotation generated by the impingement model 436 for each selected candidate orientation for the acetabular cup 104 to one or more thresholds. If both predicted rotation amounts associated with a particular selected candidate orientation for the acetabular cup 104 are greater than the applicable threshold(s), that selected candidate orientation is identified as not resulting in implant impingement and is included in the set of target orientations for the acetabular cup 104 in this pass of the algorithm. If either predicted rotation amount associated with a particular selected candidate orientation is less than the applicable threshold(s), that selected candidate orientation does not become part of the set of target orientations for the acetabular cup 104 in this pass of the algorithm. In the illustrative embodiment of block 1014, the thresholds used to evaluate the predicted amounts of rotation for each selected candidate orientation are updated dynamically based on whether those thresholds produce an adequate number of target orientations for the acetabular cup 104. For instance, if the default values of the thresholds applied in block 1014 do not produce a sufficient number of target orientations, the thresholds are incrementally lowered and block 1014 is performed again. This process is iteratively repeated until block 1014 produces a sufficient number of target orientations for the acetabular cup 104 or until the algorithm determines that a sufficient number of target orientations cannot be produced for the current set of input conditions.

Each of the selected candidate orientations that satisfies the thresholds of block 1014 is thus identified as an orientation for the acetabular cup 104 that will not result in either edge loading of the acetabular cup 104 by the femoral prosthesis 102 or impingement of the femoral prosthesis 102 and the acetabular cup 104 when the femoral prosthesis 102 is oriented at the corresponding version. The set of these orientations forms a set of target orientations for the acetabular cup 104 for the corresponding femoral prosthesis version. In block 1016, the femoral prosthesis version can be updated to a different femoral prosthesis version in the solution space, and blocks 1004-1014 can be repeated for that femoral prosthesis version. In other embodiments, the system may determine sets of target orientations for the acetabular cup 104 corresponding to all femoral prosthesis versions in the solution space in parallel, rather than sequentially.

Figure 11:
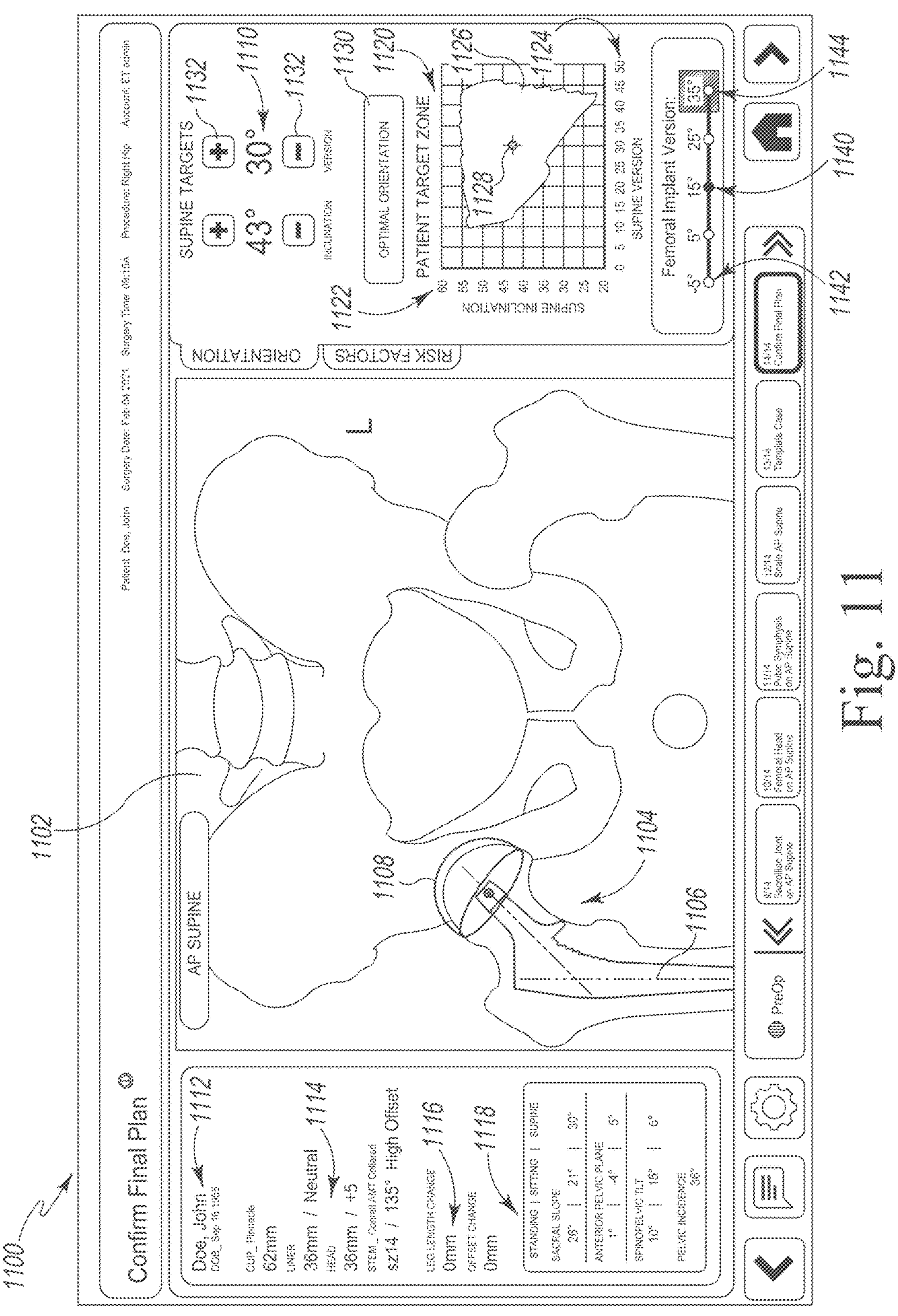
FIG. 11 is an illustrative screen image that may be displayed during the performance of the method of FIGS. 10A-10B and that includes a graphic showing a patient target zone corresponding to a femoral implant version of 15 degrees and an optimal orientation for the acetabular cup within the patient target zone.

After block 1002, the illustrative embodiment of method 1000 proceeds to block 1020, shown in FIG. 10B, in which the analysis device 402 displays a GUI presenting certain results of the algorithm run in block 1002. One illustrative example of a GUI 1100 that may be displayed in block 1020 is shown in FIG. 11. The GUI 1100 of FIG. 11 includes a medical image 1102 of the patient's hips (illustratively, an anterior-posterior supine X-ray, since the results of the algorithm run in block 1002 are being presented from a supine frame of reference in the GUI 1100). The medical image 1102 in the GUI 1100 has been annotated with a template 1104 of the hip prosthesis 100 to be implanted in the patient's right hip. The template 1104 includes a femoral prosthesis template 1106 and an acetabular cup template 1108. An orientation of the acetabular cup template 1108 in the GUI 1100 reflects the default target orientation 1110 for the acetabular cup 104 (discussed further below). The GUI 1100 further includes patient information 1112, certain type and size data 1114 for the hip prosthesis 100, bio-mechanics information 1116 relating to what changes to the patient's bio-mechanics can be expected from the current surgical plan, and pelvic tilt measurements 1118 (including, but not limited to, one or more pelvic tilt measurements determined during the method 600 discussed above).

As shown in FIG. 11, the GUI 1100 further includes a graphic 1120 representing one of the sets of target orientations for the acetabular cup 104 that was determined in block 1002. The graphic 1120 illustratively includes an inclination axis 1122, a version axis 1124, and a closed shape 1126 surrounding the represented set of target orientations for the acetabular cup 104 when graphed relative to the inclination and version axes 1122, 1124. The set of target orientations for the acetabular cup 104 can be represented in the graphic 1120 by the closed shape 1126 because outlier orientations that lack sufficient neighbors are excluded from the set of target orientations. The graphic 1120 further includes a marker 1128 indicating a centroid of the closed shape 1126, which the algorithm presents as the default target orientation 1110 and labels as the "optimal orientation" in interface element 1130 of the GUI 1100. As used herein, an "interface element" may be embodied as one or more text characters (including letters and/or numbers), one or more graphics (e.g., shapes, pictures, etc.), or any combination of text and graphics.

Figure 12:
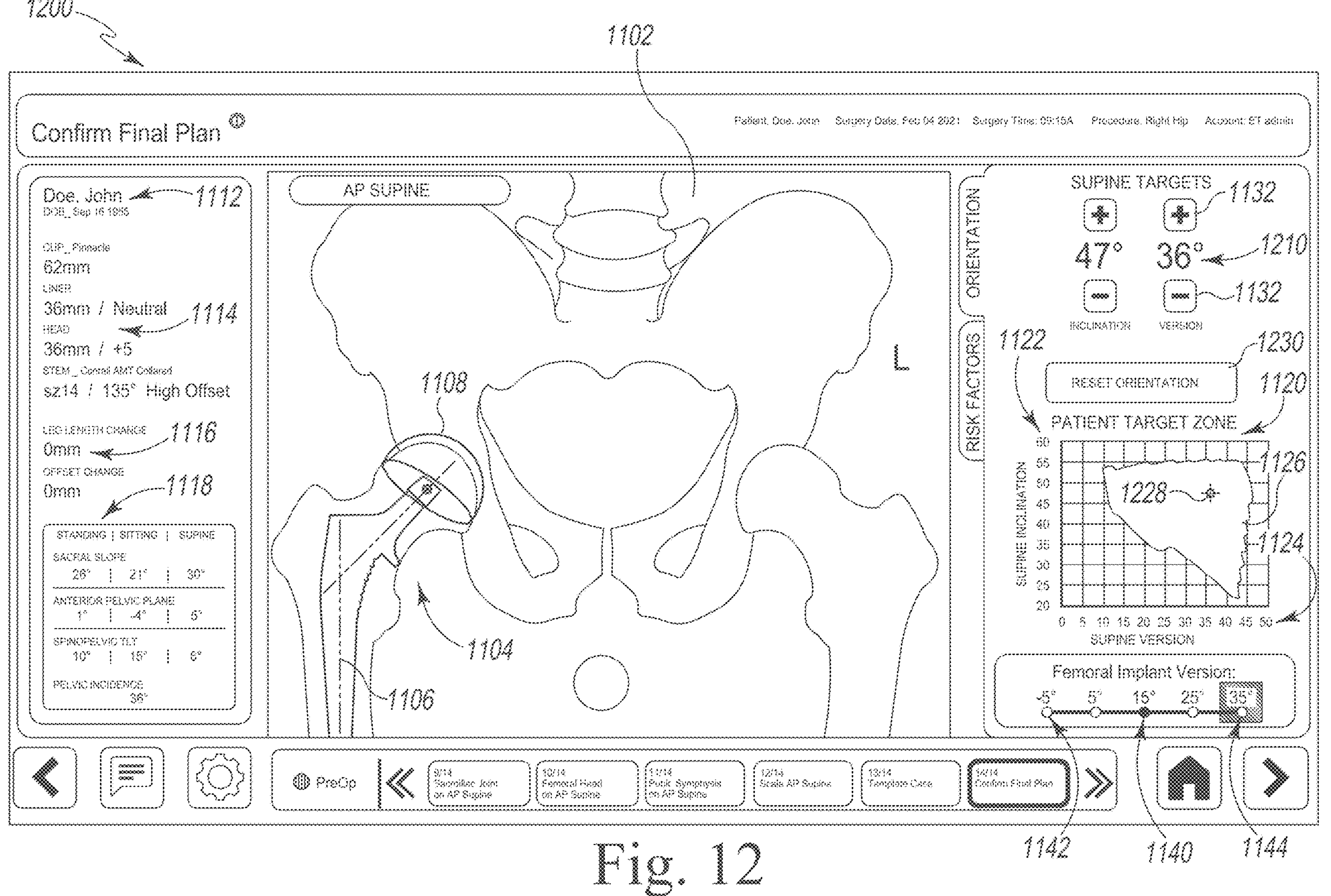
FIG. 12 is an illustrative screen image that may be displayed during the performance of the method of FIGS. 10A-10B and that includes a graphic showing the patient target zone corresponding to the femoral implant version of 15 degrees and a user-modified orientation for the acetabular cup within the patient target zone.

Several interface elements 1132 of the GUI 1100 allow a user to increment or decrement the inclination or the version of the default target orientation 1110 to create a different selected target orientation as the planned orientation for the acetabular cup 104. For instance, if the user adjusts the default target orientation 1110 shown in the GUI 1100 of FIG. 7 by incrementing the inclination by 4 degrees (from 43 degrees up to 47 degrees) and incrementing the version by 6 degrees (from 30 degrees up to 36 degrees), the analysis device 402 will display an updated GUI 1200, as shown in FIG. 12. The GUI 1200 displays the new selected target orientation 1210 (47 degrees inclination, 36 degrees version) for the acetabular cup 104. The marker 1128 on the graphic 1120 is replaced by a new marker 1228 that denotes the selected target orientation 1210 on the graphic 1120. (This new marker 1228 is no longer the centroid of the closed shape 1126.) In some embodiments, the orientation of the acetabular cup template 1108 overlaid on medical image 1102 in GUI 1200 may be updated to reflect the selected target orientation 1210 for the acetabular cup 104. The interface element 1130 is replaced by another interface element 1230 to indicate that the selected target orientation 1210 is no longer the "optimal orientation." The interface element 1230 illustratively reads "reset orientation" and can be selected by a user to return to the default target orientation 1110 (43 degrees inclination, 30 degrees version) and to the GUI 1100 of FIG. 11.

As shown in FIGS. 11 and 12, the GUIs 1100, 1200 also include interface elements 1140, 1142 related to the various femoral prosthesis versions for which sets of target orientations for the acetabular cup 104 were generated in block 1002. The interface element 1140 indicates that the graphic 1120, 1220 (representing one set of target orientations for the acetabular cup 104) that is actively being displayed on each GUI 1100, 1200 corresponds to the femoral prosthesis 102 being oriented at a version of 15 degrees. (As discussed above, in other embodiments, this initial femoral prosthesis version may correspond to the pre-operative version of the patient's natural femur, rather than a default value like 15 degrees.) In the illustrative embodiment, the interface element 1140 includes a solid circle next to the text "15°". The interface elements 1142 (illustratively embodied as hollow circles next to the text "−5°", "5°", and "25°") each indicate that another set of target orientations for the acetabular cup 102 that was also generated in block 1002, but corresponds to a different femoral prosthesis version, is available for review. For instance, in FIGS. 11 and 12, the interface elements 1142 indicate that sets of target orientations for the acetabular cup 102 corresponding to the femoral prosthesis being oriented at each of −5 degrees version, 5 degrees version, and 25 degrees version are available for review by the user. As noted above, different embodiments may utilize different solution spaces for femoral prosthesis version.

As noted above, in some circumstances, block 1002 may not be able to determine a sufficient set of target orientations for the acetabular cup 104 for every femoral prosthesis version in the solution space. For instance, the algorithm may determine an insufficient number of orientations for the acetabular cup 104 that do not result in edge loading of the acetabular cup 104 by the femoral prosthesis 102 and impingement of the femoral prosthesis 102 and the acetabular cup 104 when the femoral prosthesis 102 is oriented at a particular version. In other words, the number of target orientations for the acetabular cup 104 when the femoral prosthesis is oriented at that particular version is below a threshold required by the software to generate a "patient target zone." In such cases, the resulting GUI may include an interface element that indicates that analysis device 402 cannot generate a sufficient set of target orientations for the acetabular cup 104 when the femoral prosthesis is oriented at that version. As shown in FIGS. 11 and 12, for example, the GUIs 1100, 1200 each include an interface element 1144 that indicates that the femoral implant version of 35 degrees did not produce a sufficient set of target orientations for the acetabular cup 104 in block 1002. In the illustrative embodiments, this interface element 1144 is embodied as a hollow circle next to the text "35°", with both the hollow circle and the text colored red to distinguish the interface element 1144 from the interface elements 1142.

After block 1020, the illustrative embodiment of method 1000 proceeds to block 1022, in which the analysis device 402 receives a user input associated with one of the interface elements 1142. For instance, block 1022 may involve the user clicking on one of the interface elements 1142 with a mouse pointer or touching one of the interface elements 1142 with a finger or stylus (e.g., where the GUI 1100 is displayed on a touchscreen). The analysis device 402 interprets this user input as indicating that the user desires to review a different set of target orientations for the acetabular cup 102 that was generated in block 1002 and is associated with the selected interface element 1142. In the illustrative embodiment of method 1000, each of the different sets of target orientations for the acetabular cup 102 is determined in block 1002 before receiving the user input in block 1022, which allows the new set of target orientations to be displayed almost immediately after the user input is received.

Figure 13:
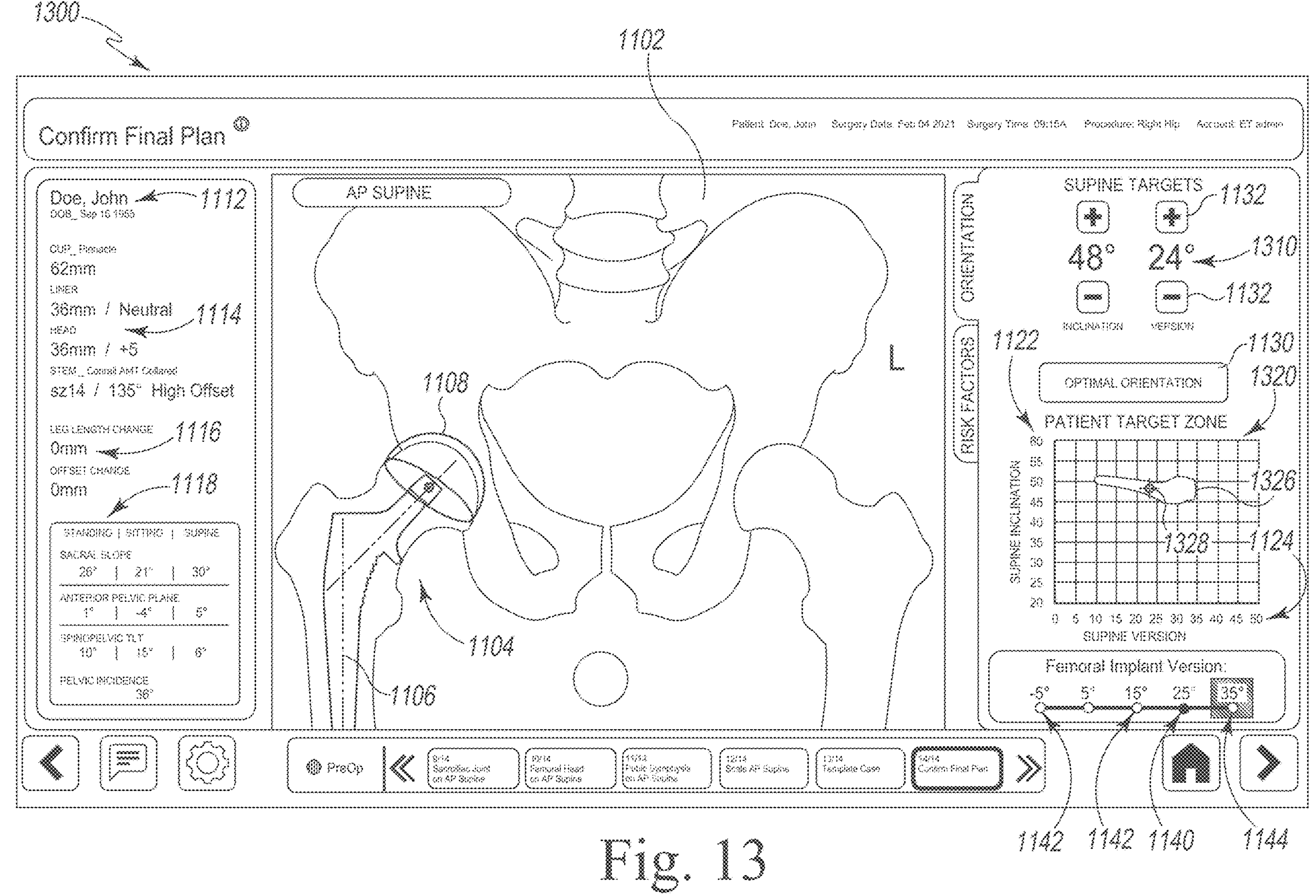
FIG. 13 is an illustrative screen image that may be displayed during the performance of the method of FIGS. 10A-10B and that includes a graphic showing a different patient target zone corresponding to a femoral implant version of 25 degrees and an optimal orientation for the acetabular cup within the different patient target zone.

In response to receiving the user input in block 1022, the method 1000 proceeds to block 1024, which displays an updated or new GUI presenting other results of the algorithm run in block 1002. One illustrative example of a GUI 1300 that may be displayed in block 1024 is shown in FIG. 13. The GUI 1300 of FIG. 13 is similar to the GUI 1100 of FIG. 11, except for the differences described below. The graphic 1120 of GUI 1100 is replaced with the graphic 1320 of GUI 1300. Like the graphic 1120, the graphic 1320 includes the inclination axis 1122 and the version axis 1124. However, the graphic 1320 includes a different closed shape 1326 because the graphic 1320 represents a different set of target orientations for the acetabular cup 104 than that represented by the closed shape 1126 of graphic 1120. The closed shape 1326 surrounds the represented set of target orientations for the acetabular cup 104 when graphed relative to the inclination and version axes 1122, 1124. The set of target orientations for the acetabular cup 104 can be represented in the graphic 1320 by the closed shape 1326 because outlier orientations that lack sufficient neighbors are excluded from the set of target orientations. The graphic 1320 further includes a marker 1328 indicating a centroid of the closed shape 1326, which the algorithm presents as the default target orientation 1310 and labels as the "optimal orientation" in interface element 1130 of the GUI 1300. The interface element 1142 that was associated with 25 degrees femoral prosthesis version in GUI 1100 is replaced with an interface element 1140 (illustratively a solid circle next to the text "25°") that indicates that the graphic 1320 that is actively being displayed on the GUI 1300 corresponds to the femoral prosthesis 102 being oriented at a version of 25 degrees. The interface element 1140 that was associated with 15 degrees femoral prosthesis version in GUI 1100 is replaced with an interface element 1142 (illustratively a hollow circle next to the text "15°") that indicates this data set is no longer being actively displayed but is available for review.

In some embodiments, after block 1024, the method 1000 may proceed to block 1026, in which the analysis device 402 receives a user input associated with one of the interface elements 1142 in GUI 1300. For instance, block 1022 may involve the user clicking on one of the interface elements 1142 with a mouse pointer or touching one of the interface elements 1142 with a finger or stylus (e.g., where the GUI 1300 is displayed on a touchscreen). The analysis device 402 interprets this user input as indicating that the user desires to review a different set of target orientations for the acetabular cup 102 that was generated in block 1002 and is associated with the selected interface element 1142. For instance, if the user input in block 1026 is associated with the interface element 1142 representing the initial femoral prosthesis version value (e.g.,) 15°, the method 1000 returns to block 1020 and displays the GUI 1100 of FIG. 11 once again. Alternatively, if the user input in block 1026 is associated with another of the interface elements 1142 of GUI 1300, the method 1000 effectively returns to block 1024 but displays a different GUI (not shown) that corresponds to a femoral implant version of −5 degrees or 5 degrees, for instance. Once again, each of the different sets of target orientations for the acetabular cup 102 may be determined in block 1002 before receiving the user input in block 1026, which allows the new set of target orientations to be displayed almost immediately after the user input is received.

Figure 14:
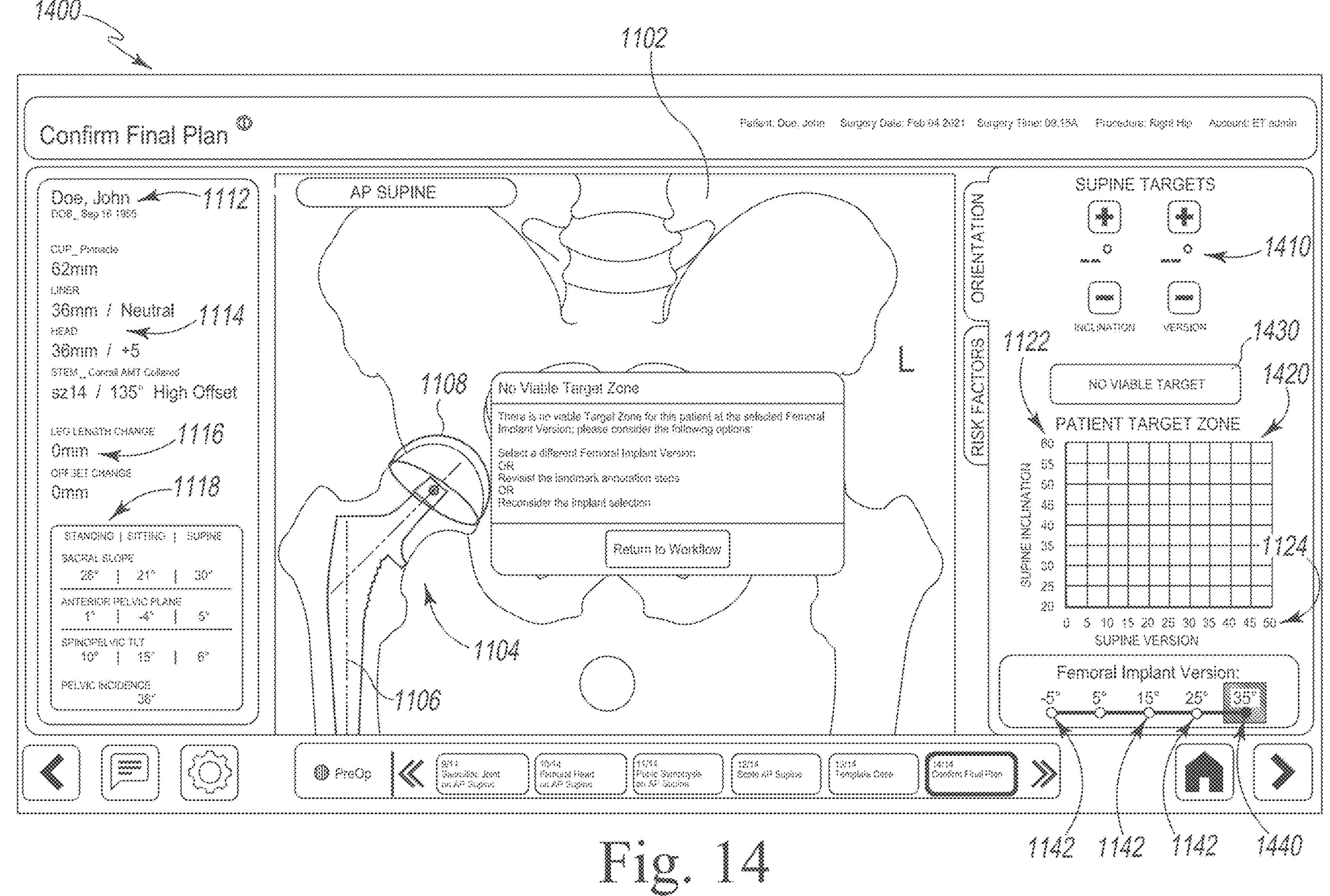
FIG. 14 is an illustrative screen image that may be displayed during the performance of the method of FIGS. 10A-10B and that includes a graphic showing no patient target zone corresponding to a femoral implant version of 35 degrees and an associated user alert.

If a user selects the interface element 1144, the analysis device 402 may display an updated or new GUI indicating that the algorithm identified an insufficient number of orientations for the acetabular cup 104 that do not result in edge loading of the acetabular cup 104 by the femoral prosthesis 102 and impingement of the femoral prosthesis 102 and the acetabular cup 104 when the femoral prosthesis 102 is oriented at the associated version. One illustrative example of a GUI 1400 that may be displayed in response to the user selecting the interface element 1144 is shown in FIG. 14. The GUI 1400 of FIG. 14 is similar to the GUI 1100 of FIG. 11, except for the differences described below. The graphic 1120 of GUI 1100 is replaced with the graphic 1420 of GUI 1400. Like the graphic 1120, the graphic 1420 includes the inclination axis 1122 and the version axis 1124. However, the graphic 1420 does not include a closed shape because the algorithm did not output a set of target orientations for the acetabular cup 104 for this femoral prosthesis version. The interface element 1130 of GUI 1100 is replaced by another interface element 1430 in GUI 1400 to indicate that, for this femoral prosthesis version, there is "no viable target." Similarly, the target orientation 1110 of GUI 1100 is replaced by null placeholders 1410 in GUI 1400. Additionally, the interface element 1144 of GUI 1100 is replaced with an interface element 1440 (illustratively a solid circle next to the text "35°") that indicates that the graphic 1420 that is actively being displayed on the GUI 1400 corresponds to the femoral prosthesis 102 being oriented at a version of 35 degrees. In the illustrative embodiment, both the solid circle and the text of interface element 1440 are colored red to distinguish the interface element 1440 from the interface element 1140 (see FIGS. 11-13). The interface element 1140 that was associated with 15 degrees femoral prosthesis version in GUI 1100 is replaced with an interface element 1142 (illustratively a hollow circle next to the text "15°") that indicates this data set is no longer being actively displayed but is available for review. Finally, the GUI 1400 illustratively includes a pop-up window, titled "no viable target zone", which presents the user with several suggestions for successfully identifying a target orientation for the acetabular cup 102.

In addition to the "Orientation" information discussed above, the illustrative GUIs 1100, 1200, 1300, 1400 also each include a "Risk Factors" tab, as shown in FIGS>11-14. A user may select this "Risk Factors" tab to view various messages output by the algorithm, including the messages discussed above with regard to blocks 638-646 of FIG. 6C.

Alternative embodiments of the method 1000 may additionally incorporate one or more target boundaries when displaying sets of target orientations for the acetabular cup 104. By way of example, FIGS. 15A-D illustrate various alternative graphics 1120A-D that show (or account for) target boundaries and that could be included in the GUI 1100 in place of the graphic 1120 described above. While FIGS. 15A-D each illustrate different approaches to incorporating target boundaries with respect to the graphic 1120, it will be appreciated that one or more target boundaries could be similarly incorporated into any of the graphics shown or described in the present disclosure (such as, for example, the graphics 1220, 1320). Furthermore, while the alternative graphics 1120A-D each illustratively incorporate two target boundaries, it is contemplated that any number of target boundaries might be used in different embodiments.

Figure 15A:
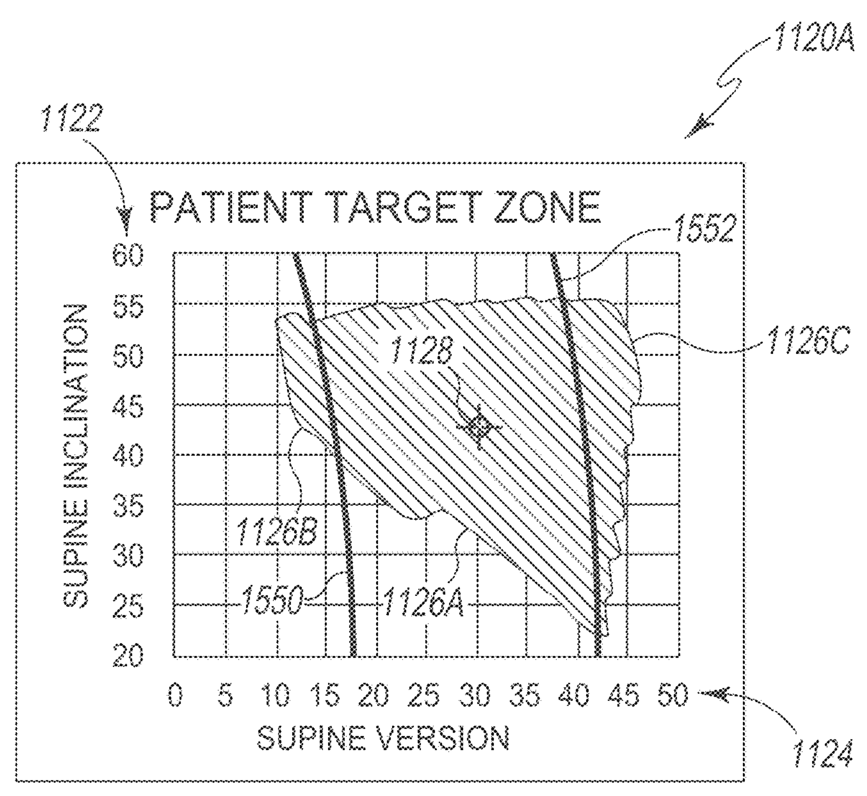
FIG. 15A illustrates an alternative graphic for the screen image of FIG. 11 that shows the patient target zone together with two target boundaries.
Figure 15B:
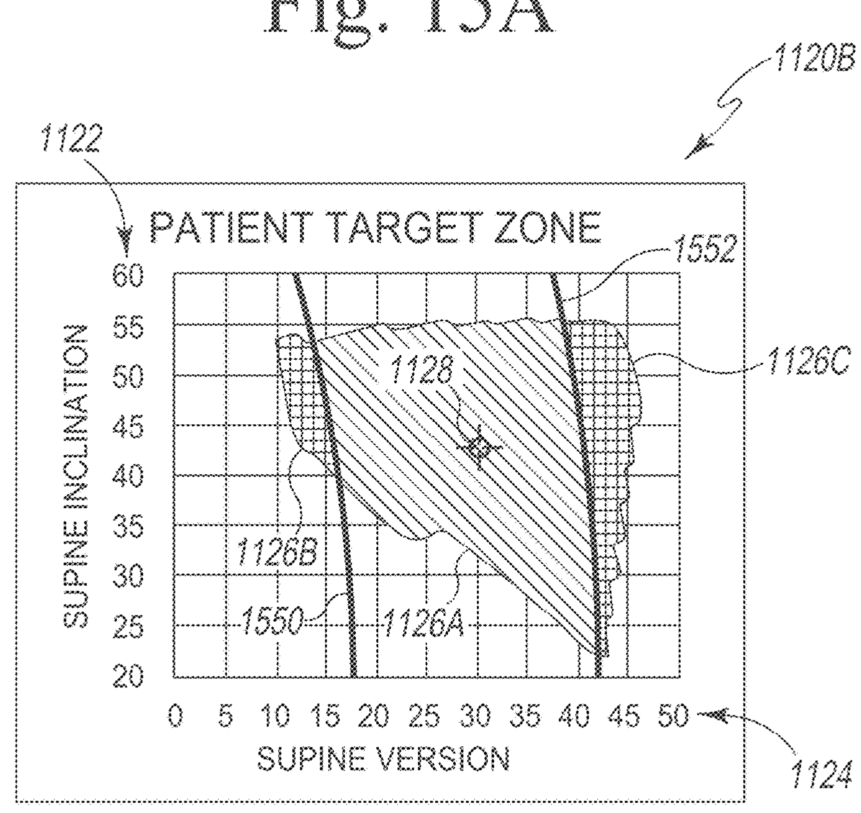
FIG. 15B illustrates another alternative graphic for the screen image of FIG. 11 that shows the patient target zone together with the two target boundaries, but with portions of the patient target zone outside of the target boundaries being visually distinct (differently colored, in this embodiment)
Figure 15C:
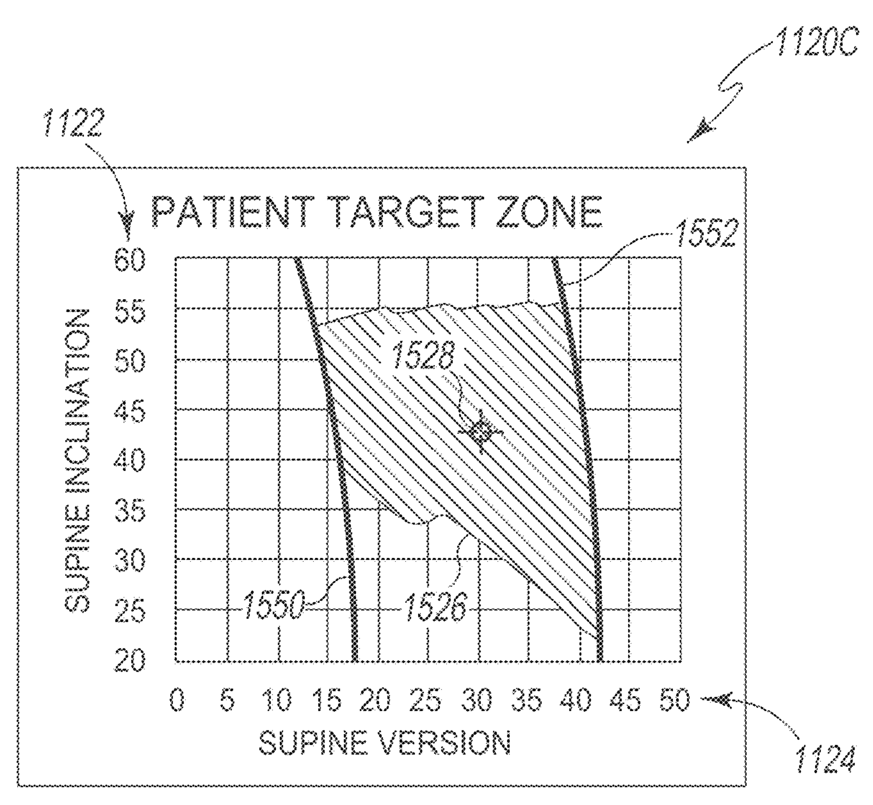
FIG. 15C illustrates yet another alternative graphic for the screen image of FIG. 11 that shows the two target boundaries and a modified patient target zone with portions outside of the target boundaries removed.
Figure 15D:
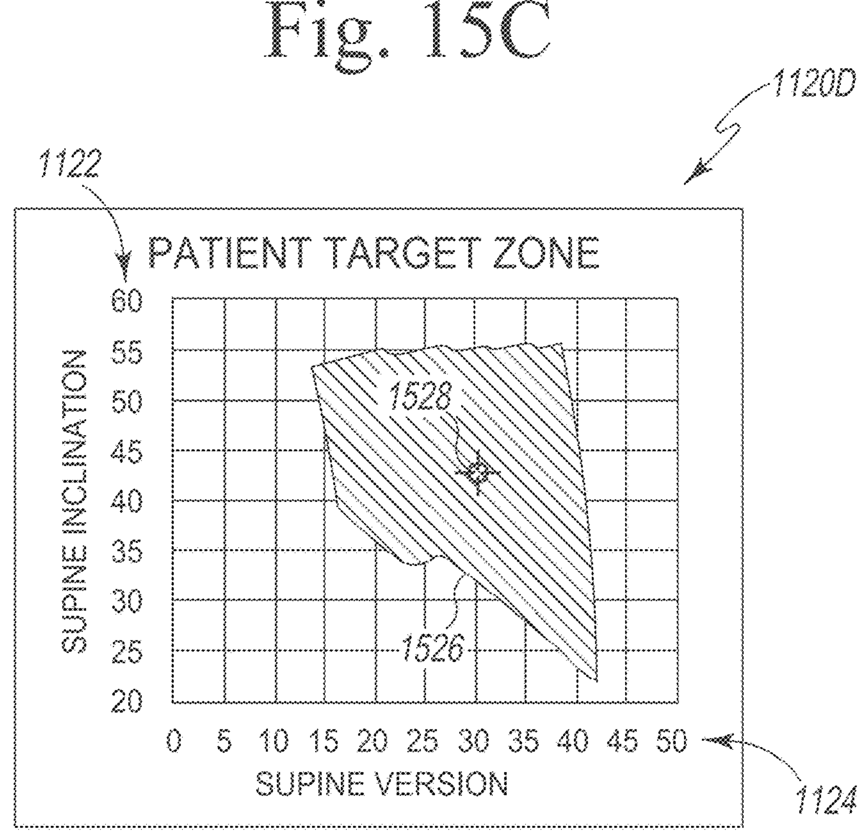
FIG. 15D illustrates yet another alternative graphic for the screen image of FIG. 11 that shows just the modified patient target zone with portions outside of the target boundaries removed.

One alternative graphic 1120A for representing one of the sets of target orientations for the acetabular cup 104 that was determined in block 1002 of the method 1000 is shown in FIG. 15A. Another alternative graphic 1120B for representing the same set of target orientations for the acetabular cup 104 is shown in FIG. 15B. Like the graphic 1120, the alternative graphics 1120A, 1120B each include the inclination axis 1122, the version axis 1124, the closed shape 1126 (surrounding the represented set of target orientations for the acetabular cup 104 when graphed relative to the inclination and version axes 1122, 1124), and a marker 1128 positioned at a centroid of the closed shape 1126, each of which were described in detail above. The alternative graphics 1120A, 1120B both present the patient target zone in a supine frame of reference, like to the graphic 1120. In contrast to graphic 1120, however, the alternative graphics 1120A, 1120B each additionally include a line 1550 representing a minimum target boundary and a line 1552 representing a maximum target boundary. Although the lines 1550, 1552 each have a similar appearance in the illustrative embodiments, it is contemplated that the lines may have different coloring, shading, hatching, patterns, and/or labels in other embodiments, in order to indicate the different target boundaries represented by each line.

The lines 1550, 1552 each represent a corresponding target boundary graphed relative to the inclination axis 1122 and the version axis 1124 of the graphics 1120A, 1120B. Each target boundary reflects a particular constraint on positioning of the acetabular cup 104. For instance, each target boundary may reflect a minimum or maximum allowable value for the version or inclination of the acetabular cup 104 relative to a specific frame of reference (e.g., relative to a particular functional position of the pelvis of the patient). A target boundary may also be based on both version and inclination of the acetabular cup 104, for example, a particular relationship between the version and inclination of the acetabular cup 104. The constraints captured in the target boundaries may be derived from medical literature and/or studies. For instance, in the illustrative embodiment, one target boundary (represented by the line 1550) is predefined to signify a minimum allowable version for the acetabular cup 104 of 10 degrees when the patient is in a flexed seated position, while the other target boundary (represented by the line 1552) is predefined to signify a maximum allowable version for the acetabular cup 104 of 30 degrees while the patient is in a standing position. These two target boundaries were derived from J. W. Pierrepont, "Patient-Specific Component Alignment in Total Hip Arthroplasty," Ph.D. Thesis, The University of Sydney, June 2017. In other embodiments, other target boundaries representing other constraints derived from different medical literature or studies may be used.

It is also contemplated that a target boundary may be user-defined in order to reflect a constraint on positioning of the acetabular cup 104 preferred by a particular surgeon (or group of surgeons) using the system 400, 500. By way of example, if a surgeon using the system 400, 500 prefers to avoid placements of the acetabular cup 104 that would result in the acetabular cup 104 having a version or inclination that is greater or less than a particular value when the patient is in a certain functional position (e.g., seated, standing, etc.), a target boundary may be defined to represent that surgeon preference. In various embodiments, the one or more target boundaries could be all user-defined, or all predefined based on values taken from medical literature and/or studies, or a combination of user-defined and predefined based on values taken from medical literature and/or studies.

Where a target boundary based only on version or inclination is defined in the same frame of reference in which the set(s) of target orientations for the acetabular cup 104 are being displayed to the user (e.g., a supine or standing frame of reference, as described above), a straight line representing that target boundary can be superimposed on the two-dimensional graph delineated by the inclination and version axes 1122, 1124. While such a target boundary may be defined relative to only one axis (e.g., a minimum acetabular cup version of 5 degrees when the patient is standing), a line representing that target boundary will typically have a slope because the apparent value of acetabular cup version changes with increases or decreases in acetabular cup inclination due to projection of the three-dimensional structure onto a two-dimensional image.

Where a target boundary is defined in a different frame of reference than the frame of reference being used to display a set of target orientations for the acetabular cup 104, that target boundary must be converted between the two frames of references before it can be graphed relative to the inclination and version axes 1122, 1124. By way of example, where a patient target zone is presented in a supine frame of reference (as in graphics 1120A, 1120B) but a target boundary has been defined relative to a standing or flexed seated frame of reference (such as a minimum allowable version for the acetabular cup 104 of 10 degrees when the patient is in a flexed seated position, or a maximum allowable version for the acetabular cup 104 of 30 degrees while the patient is in a standing position, as described above), the target boundary must be converted to the supine frame of reference before it can be added to the graphic displaying the patient target zone. This conversion between different frames of reference is based on the specific patient's pelvic mobility, meaning that the same target boundary will be represented by lines positioned in different locations relative to the inclination and version axes 1122, 1124 for different patients. When converting a target boundary defined in one frame of reference into another frame of reference for display relative to the inclination and version axes 1122, 1124, the system 400, 500 can utilize the pelvic tilt measurements determined during the method 600, as described above.

Furthermore, there is a non-linear relationship between pelvic tilt, acetabular cup inclination, and acetabular cup version. As such, a line reflecting this non-linear relationship relative to the inclination and version axes 1122, 1124 will typically be curved (similar to the curved lines 1550, 1552 shown in the illustrative embodiments of FIGS. 15A-C). It will be appreciated that the shape of the curved line will change from case-to-case, as it is dependent on patient-specific pelvic mobility. Once again, the system 400, 500 can utilize the pelvic tilt measurements determined during the method 600 when converting between different frames of reference. It is also contemplated that some embodiments, rather than using curved lines to represent converted target boundaries, may use straight lines which approximate the more complex relationship between pelvic tilt, acetabular cup inclination, and acetabular cup version. It is also possible that a more complex target boundary based on both version and inclination in one frame of reference may become a straight line when converted to a different frame of reference.

In the illustrative case depicted in FIGS. 15A and 15B, the lines 1550, 1552 both intersect the closed shape 1126, thereby dividing the closed shape 1126 into portions 1126A, 1126B, and 1126C. In this particular case, the closed shape portion 1126B lies outside the minimum version target boundary represented by line 1550, the closed shape portion 1126C lies outside the maximum version target boundary represented by line 1552, and the closed shape portion 1126A lies inside both the minimum version target boundary represented by line 1550 and the maximum version target boundary represented by line 1552. As described above, the shape and positioning of the lines 1550, 1552 depends on patient-specific pelvic tilt measurements and, thus, will change from case to case. As such, whether or not a given line representing a target boundary intersects the closed shape representing a set of target orientations for the acetabular cup 104 (and, if so, what portion it intersects) will change with the patient's pelvic mobility, as well as the size and shape of each patient target zone output by block 1002 of method 1000.

In some embodiments, each portion of the closed shape 1126 that is outside any of the one or more target boundaries is visually distinct from each portion of the closed shape that is inside all of the one or more target boundaries. By way of example, in illustrative graphic 1120B shown in FIG. 15B, the closed shape portion 1126B, which is outside the minimum version target boundary represented by line 1550, and the closed shape portion 1126C, which is outside the maximum version target boundary represented by line 1552, are each colored yellow. By contrast, the closed shape portion 1126A, which lies inside both the minimum version target boundary represented by line 1550 and the maximum version target boundary represented by line 1552, is colored green. In other embodiments, different shading, hatching, patterns, and/or labels may be used to provide visual distinctiveness to different portions of the closed shape 1126 with different relationships to the one or more target boundaries. In some scenarios, it is possible that no portion of the closed shape 1126 will lie within the target boundaries (i.e., no candidate orientation satisfied all selection criteria, including any applicable boundaries). In such cases, the system 400, 500 may select what graphical elements to display or not display based on one or more user-defined preferences.

In other alternative embodiments, the one or more target boundaries may be used to remove certain target orientations for the acetabular cup 104 output by block 1002 of the method 1000 before the patient target zone is displayed to the user. For instance, in the alternative graphic 1120C of FIG. 15C as well as the alternative graphic 1120D of FIG. 15D, certain target orientations for the acetabular cup 104 that were predicted to not result in either edge loading of the acetabular cup by the femoral prosthesis or impingement of the femoral prosthesis and the acetabular cup (in block

1002) but that did not satisfy both target boundaries represented by lines 1550, 1552 have been removed from the patient target zone. In particular, target orientations below the minimum version target boundary represented by line 1550 (i.e. the closed shape portion 1126B in FIGS. 15A and 15B) have been removed, and target orientations above the maximum version target boundary represented by line 1552 (i.e. the closed shape portion 1126C in FIGS. 15A and 15B) have also been removed.

As a result of removing target orientations that do not satisfy one or more of the target boundaries, the closed shape 1526 included in the graphics 1120C, 1120D is different than the closed shape 1126 included in the graphics 1120A, 1120B. The modified closed shape 1526 (which matches the closed shape portion 1126A from FIGS. 15A and 15B) represents the target orientations that both (i) are predicted to not result in either edge loading of the acetabular cup by the femoral prosthesis or impingement of the femoral prosthesis and the acetabular cup (in block 1002) and (ii) satisfy all incorporated target boundaries. In this way, the one or more target boundaries can serve as an additional filter for which orientations for the acetabular cup 104 are included in the patient target zone. In such embodiments, the marker indicating the centroid of the closed shape may also be modified. For instance, in FIGS. 15C and 15D, the marker 1528 indicates the new centroid of the modified closed shape 1526. It is also contemplated that, where the patient target zone has been modified to remove target orientations for the acetabular cup 104 that do not satisfy all applicable target boundaries, lines representing the target boundaries may be optionally included (as in the alternative graphic 1120C of FIG. 15C) or not included (as in the alternative graphic 1120D of FIG. 15D).

Figure 16:
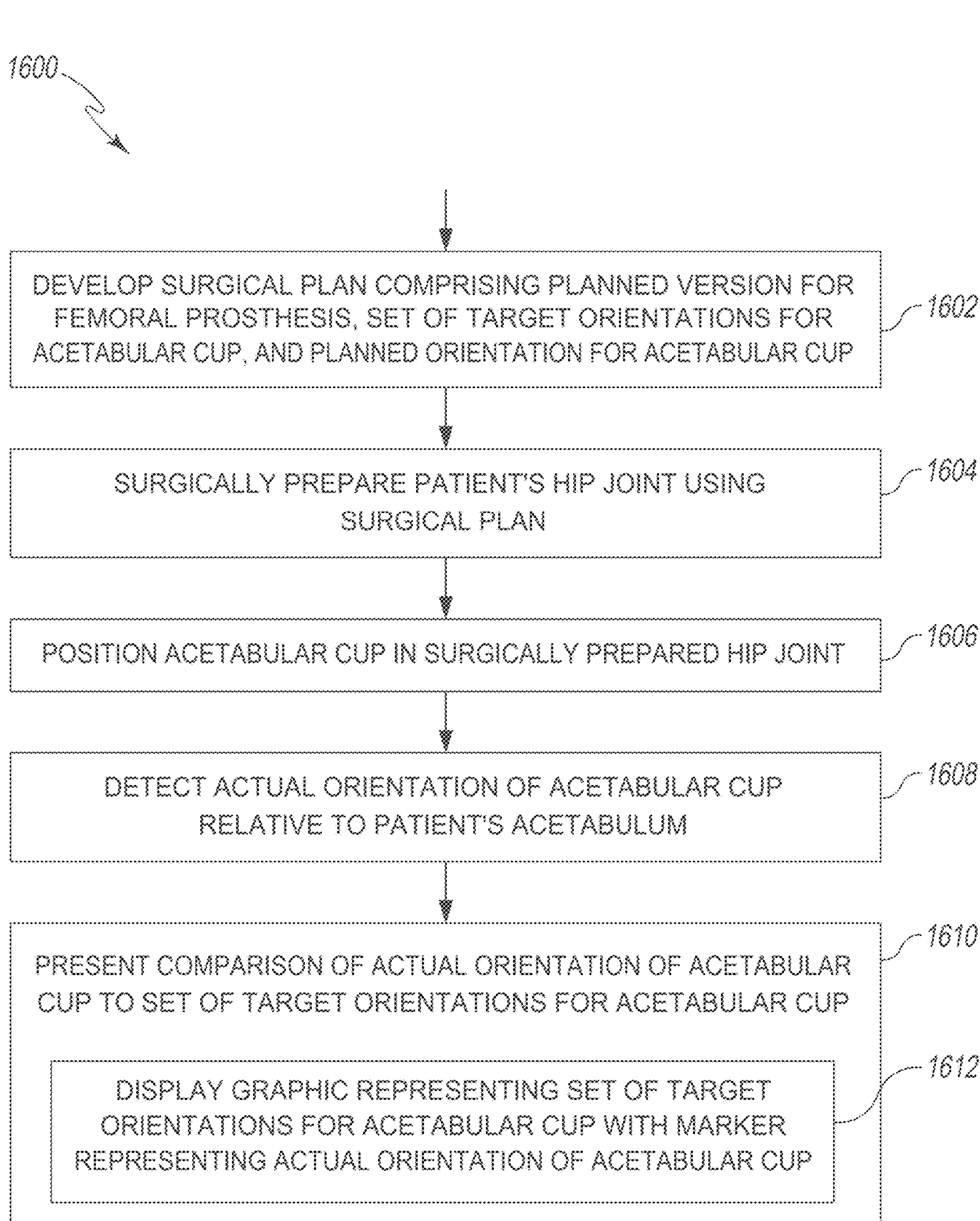
FIG. 16 is a flow chart diagram of a method for an orthopaedic surgical procedure on a hip of a patient to implant a hip prosthesis (such as the hip prosthesis of FIG. 1), which may be performed by an orthopaedic surgeon using the computer system of FIG. 4 or the computer system of FIG. 5.

As noted above, the systems 400, 500 may also be used to assist an orthopaedic surgeon in performing an orthopaedic surgical procedure on a hip joint of a patient to implant a hip prosthesis 100. One example of a method 1600 that can be performed by an orthopaedic surgeon using one of the systems 400, 500 is illustrated as a flowchart in FIG. 16. The method 1600 begins with block 1602, in which a user (e.g., the orthopaedic surgeon) operates the computer system 400 to develop a surgical plan for the orthopaedic surgical procedure. Any of the systems and methods described in the present disclosure may be used to generate the surgical plan in block 1602. The surgical plan includes, among other things, a planned version for the femoral prosthesis 102 of the hip prosthesis 100 to be implanted (e.g., selected by the user), a set of target orientations for the acetabular cup 104 of the hip prosthesis 100 to be implanted (e.g., generated in block 1002 of FIG. 10A for the planned version of the femoral prosthesis 102), and a planned orientation for the acetabular cup 104 (e.g., chosen from among the set of target orientations using the graphical user interfaces of FIGS. 11-15D). Block 1602 may be performed pre-operatively and/or intra-operatively. For instance, in some embodiments, the surgical plan may be developed pre-operatively but then revised or redeveloped intra-operatively.

After at least an initial version of the surgical plan is developed in block 1602, the method 1600 proceeds to block 1604, in which the orthopaedic surgeon prepares the patient's hip joint using the surgical plan. Certain aspects of the surgical plan, such as the size and type of hip prosthesis 100 selected by the surgeon, the planned version of the femoral prosthesis 102, and/or planned orientation for the acetabular cup 104, may dictate other aspects of the surgical plan, such as the portions of bone to be removed in order to surgically prepare the hip joint to receive the hip prosthesis 100. In the illustrative embodiment, block 1604 involves the surgical tracking system 408 of the computer system 400 assisting the orthopaedic surgeon in preparing the hip joint according to the surgical plan developed in block 1602. For example, the surgical tracking system 408 may indicate to the surgeon whether a tracked surgical instrument is in the correct position relative to the patient's bony anatomy to accurately perform a surgical step according to the surgical plan.

After the patient's hip joint has been surgically prepared in block 1604, the method 1600 proceeds to block 1606, in which the orthopaedic surgeon positions the acetabular cup 104 in the patient's acetabulum 200. The acetabular cup 104 positioned by the surgeon in block 1606 may be a trial component (designed to test the fit of the size and type of acetabular cup 104, but not to be implanted) or may be a final component (designed to be implanted, but not yet cemented or otherwise permanently installed). In either case, after the acetabular cup 104 has been positioned in block 1606, the method 1600 proceeds to block 1608 in which the computer system 400 detects the actual orientation of the positioned acetabular cup 104 relative to the patient's acetabulum 200. In the illustrative embodiment, the method 1600 involves attaching markers to both the acetabular cup 104 and the patient's pelvis (prior to block 1608) such that the relative positions and orientations of those structures can be tracked by the surgical tracking system 408 in block 1608.

After the actual orientation of the acetabular cup 104 has been detected in block 1608, the method 1600 proceeds to block 1610, in which the computer system 400 presents a comparison of the actual orientation of the acetabular cup 104 detected in block 1608 to the set of target orientations for the acetabular cup 104 of the surgical plan developed in block 1602. It is contemplated that this comparison could be presented in textually and/or graphically. For instance, in some embodiments, the computer system 400 might present binary information to the orthopaedic surgeon indicating whether the actual orientation of the acetabular cup 104 detected in block 1608 is or is not part of the set of target orientations for the acetabular cup 104 from the surgical plan. In other embodiments, block 1610 may involve block 1612, in which the computer system displays a graphic including both a closed shape representing the set of target orientations for the acetabular cup 104 (e.g., similar to any of the graphics 1120, 1320 in FIGS. 11-13 and FIGS. 15A-D) and a marker (e.g., a crosshairs) representing the actual orientation of the acetabular cup 104 detected in block 1608 when graphed relative to the same inclination and version axes as the set of target orientations for the acetabular cup 104. It will be appreciate that the graphic displayed in block 1612 may include additional information, including any of the information described above (e.g., an optimal orientation for the acetabular cup 104, the planned orientation for the acetabular cup 104, etc.). In any case, the orthopaedic surgeon may use the information presented in block 1610 to complete the orthopaedic procedure (e.g., proceeding with the current size, type, and orientation of the acetabular cup 104, or changing to another size, type, and/or orientation for the acetabular cup 104 before proceeding).

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

The invention claimed is:

1. A method for performing an orthopaedic surgical procedure on a hip of a patient to implant a hip prosthesis having a femoral prosthesis and an acetabular cup, the method comprising:

determining, with a computer system, a first set of target orientations for the acetabular cup when the femoral prosthesis is oriented at a first version;

determining, with the computer system, a second set of target orientations for the acetabular cup when the femoral prosthesis is oriented at a second version different from the first version;

displaying, with the computer system, a first graphical user interface (GUI) that comprises (i) a first graphic representing the first set of target orientations for the acetabular cup, (ii) a first interface element indicating that the first graphic corresponds to the femoral prosthesis being oriented at the first version, and (iii) a second interface element indicating that the second set of target orientations for the acetabular cup corresponding to the femoral prosthesis being oriented at the second version is available for review;

receiving, with the computer system, a user input associated with the second interface element;

displaying, with the computer system and in response to receiving the user input associated with the second interface element, a second GUI that comprises (i) a second graphic representing the second set of target orientations for the acetabular cup, (ii) a third interface element indicating that the second graphic corresponds to the femoral prosthesis being oriented at the second version, and (iii) a fourth interface element indicating that the first set of target orientations for the acetabular cup corresponding to the femoral prosthesis being oriented at the first version is available for review;

implanting the femoral prosthesis in the patient such that the femoral prosthesis is oriented at either the first version or the second version; and implanting the acetabular cup in the patient at a planned orientation, wherein the planned orientation is selected from among (i) the first set of target orientations for the acetabular cup when the femoral prosthesis is oriented at the first version or (ii) the second set of target orientations for the acetabular cup when the femoral prosthesis is oriented at the second version.

2. The method of claim 1, wherein the computer system determines the second set of target orientations for the acetabular cup prior to receiving the user input associated with the second interface element of the first GUI.

3. The method of claim 1, wherein displaying the second GUI comprises updating the first GUI by (i) replacing the first graphic with the second graphic, (ii) replacing the first interface element with the fourth interface element, and (iii) replacing the second interface element with the third interface element.

4. The method of claim 1, further comprising:

receiving, with the computer system, a user input associated with the fourth interface element; and displaying, with the computer system, the first GUI in response to receiving the user input associated with the fourth interface element.

5. The method of claim 1, further comprising:

determining, with the computer system, a third set of target orientations for the acetabular cup when the femoral prosthesis is oriented at a third version different from the first version and from the second version;

receiving, with the computer system, a user input associated with a fifth interface element included in both the first GUI and the second GUI, the fifth interface element indicating that the third set of target orientations for the acetabular cup corresponding to the femoral prosthesis being oriented at the third version is available for review; and displaying, with the computer system and in response to receiving the user input associated with the fifth interface element, a third GUI that comprises (i) a third graphic representing the third set of target orientations for the acetabular cup, (ii) a sixth interface element indicating that the third graphic corresponds to the femoral prosthesis being oriented at the third version, (iii) the fourth interface element indicating that the first set of target orientations for the acetabular cup corresponding to the femoral prosthesis being oriented at the first version is available for review, and (iv) the second interface element indicating that the second set of target orientations for the acetabular cup corresponding to the femoral prosthesis being oriented at the second version is available for review.

6. The method of claim 1, wherein:

the method further comprises determining, with the computer system, that a number of target orientations for the acetabular cup when the femoral prosthesis is oriented at a third version is below an output threshold, wherein the third version is different from the first version and from the second version;

the first GUI further comprises a fifth interface element indicating that the computer system cannot generate a sufficient set of target orientations for the acetabular cup when the femoral prosthesis is oriented at the third version; and the second GUI also comprises the fifth interface element.

7. The method of claim 1, wherein:

the first graphic comprises an inclination axis, a version axis, and a first closed shape surrounding the first set of target orientations for the acetabular cup when graphed relative to the inclination and version axes; and the second graphic comprises the inclination axis, the version axis, and a second closed shape surrounding the second set of target orientations for the acetabular cup when graphed relative to the inclination and version axes.

8. The method of claim 7, wherein:

the first graphic further comprises a marker indicating a centroid of the first closed shape; and the second graphic further comprises a marker indicating a centroid of the second closed shape.

9. The method of claim 1, wherein:

determining the first set of target orientations for the acetabular cup comprises predicting a set of orientations for the acetabular cup that will not result in either edge loading of the acetabular cup by the femoral prosthesis or impingement of the femoral prosthesis and the acetabular cup when the femoral prosthesis is oriented at the first version; and determining the second set of target orientations for the acetabular cup comprises predicting a set of orientations for the acetabular cup that will not result in either edge loading of the acetabular cup by the femoral prosthesis or impingement of the femoral prosthesis and the acetabular cup when the femoral prosthesis is oriented at the second version.

10. The method of claim 9, wherein predicting a set of orientations for the acetabular cup that will not result in either edge loading of the acetabular cup by the femoral prosthesis or impingement of the femoral prosthesis and the acetabular cup when the femoral prosthesis is oriented at the first or second version comprises:

operating a first mathematical model with a set of candidate orientations for the acetabular cup, patient-specific pelvic tilt measurements, and type and size data for the hip prosthesis as inputs to the first mathematical model to generate, for each candidate orientation for the acetabular cup, predicted distances between (i) an edge of a cup liner of the acetabular cup and (ii) contact between the cup liner and a femoral head of the femoral prosthesis in each of a plurality of different functional positions of the patient;

selecting the candidate orientations for the acetabular cup for which each of the predicted distances is greater than a distance threshold;

operating a second mathematical model with the selected candidate orientations for the acetabular cup, the patient-specific pelvic tilt measurements, the type and size data for the hip prosthesis, and a corresponding version of the femoral prosthesis as inputs to the second mathematical model to generate, for each selected candidate orientation for the acetabular cup, predicted amounts of femoral prosthesis rotation until impingement of the femoral prosthesis and the acetabular cup in each of the plurality of different functional positions of the patient; and identifying the selected candidate orientations for the acetabular cup for which each of the predicted amounts of femoral prosthesis rotation is greater than a rotation threshold as the set of orientations for the acetabular cup predicted to not result in either edge loading of the acetabular cup by the femoral prosthesis or impingement of the femoral prosthesis and the acetabular cup when the femoral prosthesis is oriented at the corresponding version.

11. The method of claim 1, wherein the first version is 15 degrees, and wherein the second version is selected from the group consisting of −5 degrees, 5 degrees, 25 degrees, and 35 degrees.

12. The method of claim 1, wherein determining the first set of target orientations for the acetabular cup when the femoral prosthesis is oriented at the first version comprises determining target orientations for the acetabular cup when the femoral prosthesis is oriented at the same version as the patient's natural femur.

13. A method for performing an orthopaedic surgical procedure on a hip of a patient to implant a hip prosthesis having a femoral prosthesis and an acetabular cup, the method comprising:

operating, with a computer system, a first mathematical model with a set of candidate orientations for the acetabular cup, patient-specific pelvic tilt measurements, and type and size data for the hip prosthesis as inputs to the first mathematical model to generate, for each candidate orientation for the acetabular cup, predicted distances between (i) an edge of a cup liner of the acetabular cup and (ii) contact between the cup liner and a femoral head of the femoral prosthesis in each of a plurality of different functional positions of the patient;

selecting, with the computer system, the candidate orientations for the acetabular cup for which each of the predicted distances is greater than a distance threshold;

operating, with the computer system, a second mathematical model with the selected candidate orientations for the acetabular cup, the patient-specific pelvic tilt measurements, the type and size data for the hip prosthesis, and a planned version for the femoral prosthesis as inputs to the second mathematical model to generate, for each selected candidate orientation for the acetabular cup, predicted amounts of femoral prosthesis rotation until impingement of the femoral prosthesis and the acetabular cup in each of the plurality of different functional positions of the patient;

identifying, with the computer system, the selected candidate orientations for the acetabular cup for which each of the predicted amounts of femoral prosthesis rotation is greater than a rotation threshold as a set of target orientations for the acetabular cup predicted to not result in either edge loading of the acetabular cup by the femoral prosthesis or impingement of the femoral prosthesis and the acetabular cup when the femoral prosthesis is oriented at the planned version;

providing, with the computer system, a user interface that presents the set of target orientations for the acetabular cup to an orthopaedic surgeon;

receiving, with the computer system, via the user interface, an input indicating a planned orientation for the acetabular cup selected by the orthopaedic surgeon from among the set of target orientations presented via the user interface; and providing, with the computer system, via the user interface, guidance to the orthopaedic surgeon to implant the acetabular cup in an acetabulum of the patient at the planned orientation selected by the orthopaedic surgeon.

14. The method of claim 13, further comprising measuring, with the computer system, a pre-operative version of the patient's natural femur from one or more medical images, wherein the measured pre-operative version is used as the planned version for the femoral prosthesis when operating the second mathematical model.

15. The method of claim 13, wherein identifying the selected candidate orientations for the acetabular cup for which each of the predicted amounts of femoral prosthesis rotation is greater than a rotation threshold comprises:

determining a first number of selected candidate orientations for the acetabular cup for which each of the predicted amounts of femoral prosthesis rotation is greater than a first rotation threshold; and in response to the first number being less than a size threshold for the set of target orientations for the acetabular cup, determining a second number of selected candidate orientations for the acetabular cup for which each of the predicted amounts of femoral prosthesis rotation is greater than a second rotation threshold, wherein the second rotation threshold is less than the first rotation threshold.

16. The method of claim 13, wherein the user interface comprises a graphic including an inclination axis, a version axis, and a closed shape surrounding the set of target orientations for the acetabular cup when graphed relative to the inclination and version axes.

17. The method of claim 16, wherein the graphic further includes a marker indicating a centroid of the closed shape.

18. The method of claim 16, wherein the graphic further includes a marker representing the planned orientation for the acetabular cup when graphed relative to the inclination and version axes.

19. The method of claim 13, further comprising:

detecting, with the computer system, during the orthopaedic surgical procedure, an actual orientation of the acetabular cup relative to the acetabulum of the patient; and presenting, via the user interface, during the orthopaedic surgical procedure, a comparison of the actual orientation of the acetabular cup to the set of target orientations for the acetabular cup.

20. The method of claim 19, wherein the user interface comprises a graphic including an inclination axis, a version axis, a closed shape surrounding the set of target orientations for the acetabular cup when graphed relative to the inclination and version axes, and a marker representing the actual orientation of the acetabular cup when graphed relative to the inclination and version axes.

* * * * *